(12) United States Patent
John et al.

(10) Patent No.: US 12,336,986 B2
(45) Date of Patent: *Jun. 24, 2025

(54) TREATMENT AND PREVENTION OF OCULAR NEURODEGENERATIVE DISORDER

(71) Applicant: The Jackson Laboratory, Bar Harbor, ME (US)

(72) Inventors: Simon W. M. John, Bar Harbor, ME (US); Peter Alexander Williams, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 408 days.

This patent is subject to a terminal disclaimer.

(21) Appl. No.: 17/862,668

(22) Filed: Jul. 12, 2022

(65) Prior Publication Data

US 2022/0354838 A1 Nov. 10, 2022

Related U.S. Application Data

(63) Continuation of application No. 15/959,379, filed on Apr. 23, 2018, now Pat. No. 11,389,439, which is a continuation of application No. PCT/US2016/058388, filed on Oct. 24, 2016.

(60) Provisional application No. 62/366,211, filed on Jul. 25, 2016, provisional application No. 62/245,467, filed on Oct. 23, 2015.

(51) Int. Cl.
| | |
|---|---|
| A61K 31/455 | (2006.01) |
| A61K 31/19 | (2006.01) |
| A61K 31/4745 | (2006.01) |
| A61K 31/706 | (2006.01) |
| A61K 38/00 | (2006.01) |
| A61K 48/00 | (2006.01) |
| A61P 27/06 | (2006.01) |

(52) U.S. Cl.
CPC ............ *A61K 31/455* (2013.01); *A61K 31/19* (2013.01); *A61K 31/4745* (2013.01); *A61K 31/706* (2013.01); *A61K 48/00* (2013.01); *A61K 48/005* (2013.01); *A61K 48/0075* (2013.01); *A61P 27/06* (2018.01); *C12Y 207/07001* (2013.01); *A61K 38/00* (2013.01); *C12N 2750/14143* (2013.01)

(58) Field of Classification Search
CPC ...... A61K 31/455; A61K 31/19; A61K 48/00; A61K 31/4745; A61K 31/706; A61K 48/005; A61K 48/0075; A61P 27/06; C12Y 207/07001
USPC ........................................ 514/675, 44 R, 183
See application file for complete search history.

(56) References Cited

U.S. PATENT DOCUMENTS

| | | | |
|---|---|---|---|
| 7,778,326 B1 | 8/2010 | Milbrandt et al. | |
| 11,389,439 B2 * | 7/2022 | John | A61K 48/005 |
| 2005/0261234 A1 | 11/2005 | Dorey et al. | |
| 2006/0002914 A1 * | 1/2006 | Milbrandt | A61P 39/00 424/94.5 |
| 2006/0211744 A1 | 9/2006 | He et al. | |

FOREIGN PATENT DOCUMENTS

| | | |
|---|---|---|
| EP | 1510137 A1 | 3/2005 |
| WO | 2006/079217 A1 | 8/2006 |
| WO | 2008/083118 A1 | 7/2008 |
| WO | 2011123468 A1 | 10/2011 |

OTHER PUBLICATIONS

Osborne (2008) Progress in Brain Research, vol. 173, 339-352.*
Hegde et al. (2010) Mol. Cell. Biol., vol. 343(1-2), 101-105.*
English Translation of Chinese Examination Report dated Aug. 19, 2020 from corresponding Chinese Patent Application No. 2016800759508 filed on Oct. 24, 2016.
Guangyu, Li, et al., "The role of PARP-1 on light-induced apoptosis of cultural retinal ganglion cells." Chinese Ophthalmic Research vol. 26, Issue 11, English Abstract.
Anders et al., "HTSeq-a Python framework to work with high-throughput sequencing data." Bioinformatics (2015); 31(2): 166-169.
Anderson et al., "Mutations in genes encoding melanosomal proteins cause pigmentary glaucoma in DBA/2J mice," Nature Genetics (2002); 30: 81-85.
Chou et al., "Robust Mouse Pattern Electroretinograms Derived Simultaneously From Each Eye Using a Common Snout Electrode." Investigative Ophthalmology & Visual Science (2014); 55(4): 2469-2475.
Graham et al., "Chronic consumption of a western diet induces robust glial activation in aging mice and in a mouse model of Alzheimer's disease." Scientific Reports (2016); 6, Article No. 21568.
Howell et al., "Axons of retinal ganglion cells are insulted in the optic nerve early in DBA/2J glaucoma." The Journal of Cell Biology (2007); 179(7): 1523-1537.
Howell et al., Molecular clustering identifies complement and endothelin induction as early events in a mouse model of glaucoma. Journal of Clinical Investigation (2011); 121(4): 1429-1444.
John et al., "Essential iris atrophy, pigment dispersion, and glaucoma in DBA/2J mice." Investigative Ophthalmology & Visual Science (1998); 39(6). p. 951-962.

(Continued)

*Primary Examiner* — Anne Marie S Wehbe
(74) *Attorney, Agent, or Firm* — McDonnell Boehnen Hulbert & Berghoff LLP

(57) ABSTRACT

The invention relates to the use of a pharmaceutical composition containing nicotinamide (NAM) and/or pyruvate as a neuroprotective medicament or gene therapy in the treatment of neurodegenerative disorders, in particular axon degeneration of neuronal tissue in ocular-related neurodegeneration diseases including glaucoma.

19 Claims, 33 Drawing Sheets

(56) References Cited

OTHER PUBLICATIONS

Kim et al., "TopHat2: accurate alignment of transcriptomes in the presence of insertions, deletions, and gene fusions." Genome Biology (2013); 14, Article R36.
Libby et al., "Inherited glaucoma in DBA/2J mice: Pertinent disease features for studying the neurodegeneration." Visual Neuroscience (2005); 22(5): 637-648.
Libby et al., "Susceptibility to Neurodegeneration in a Glaucoma is Modified by Bax Gene Dosage." PLoS Genetics (2005); 1(1): 0017-0026.
Nakazawa et al., "Tumor Necrosis Factor-a Mediates Oligodendrocyte Death and Delayed Retinal Ganglion Cell Loss in a Mouse Model of Glaucoma." The Journal of Neuroscience (2006); 26(49): 12633-126411.
Nickells et al., "Under Pressure: Cellular and Molecular Responses During Glaucoma, a Common Neurodegeneration with Axonpathy." Annual Review of Neuroscience (2012): 35: 153-179.
Robinson et al., "edgeR: Bioconductor package for differential expression analysis of digital gene expression data." Bioinformatics (2010); 26(1): 139-140.
Saleh et al., "Longitudinal Evaluation of Retinal Ganglion Cell Function and IOP in the DBA/2J Mouse Model of Glaucoma." Investigative Ophthalmology & Visual Science (2007); 48: 4564-4572.
Savinova et al., "Intraocular pressure in genetically distinct mice: an update and strain survey." BMC Genetics (2001); 2(12).
Smith et al., "Systematic Evaluation of the Mouse Eye." Anatomy, Pathology, and Biomethods, CRC Press, Boca Raton (2002).
Hedge, et al. Inhibition of glycolysis in the retina by oxidative stress: prevention by pyruvate. Mol Cell. Biochem.: Jun. 18, 2010: 343(1-2): 101-105.
Li, et al. "The role of PARP-1 on light-induced apoptosis of cultural reginal ganglion." Chinese Ophthalmic Research 2008, Nov. 26(11):805-809.
Osborne, "Pathogenesis of ganglion "cell death" in glaucoma and neuroprotection: focus on ganglion cell axonal mitochondria." Prog Brain Res. 2008;173:339-52.
International Search Report for Application No. PCT/US2016/058388, dated Feb. 17, 2017, 4 pages.
International Preliminary Report on Patentability for Application No. PCT/US2016/058388, dated May 3, 2018, 11 pages.
Fechtner et al., "Fixed combinations of topical glaucoma medications." Current Opinion in Ophthalmology (2004), 15:132-135.
Zhu et al., "Protection of Mouse Retinal Ganglion Cell Axons and Soma from Glaucomatous and Ischemic Injury by Cytoplasmic Overexpression of Nmnat1." IOVN, Jan. 2013, vol. 54, No. 1.
Ehrlich, J. et al., "Goldmann applanation tonometry compared with corneal-compensated intraocular pressure in the evaluation of primary open-angle Glaucoma." BMC Ophthalmology, 2012, 12:52, 1471-2415.

* cited by examiner

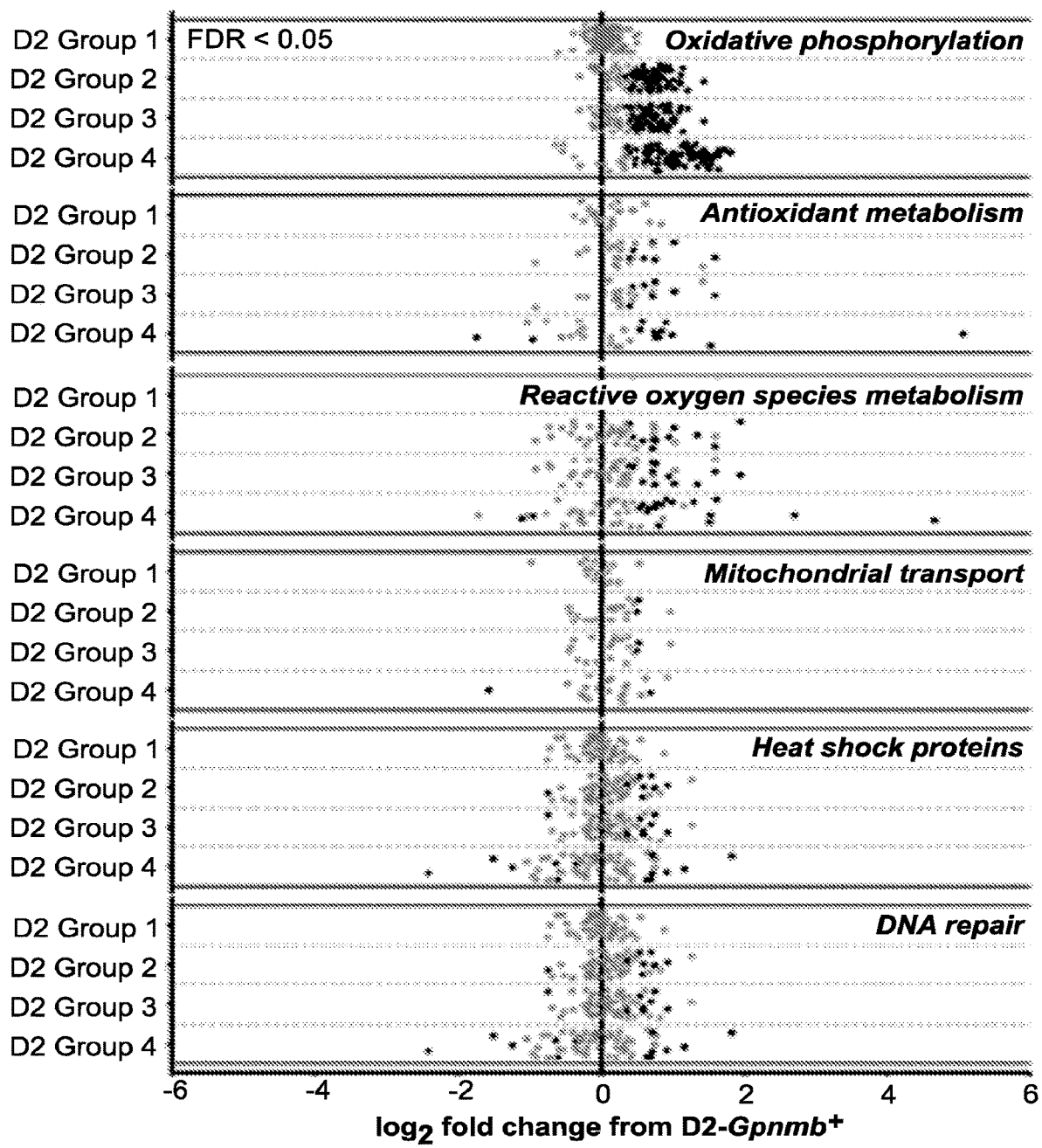

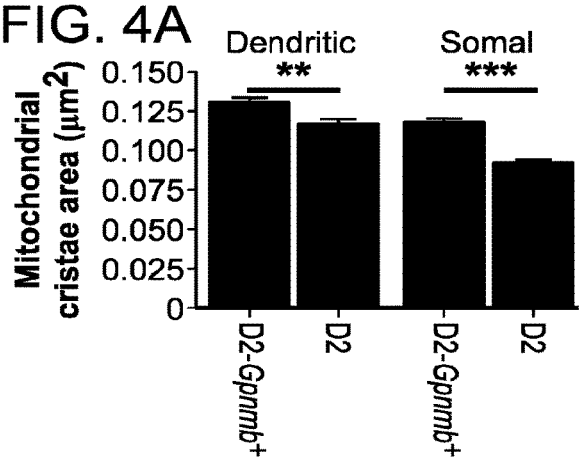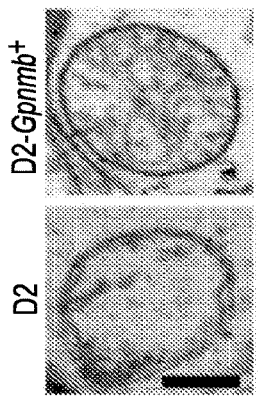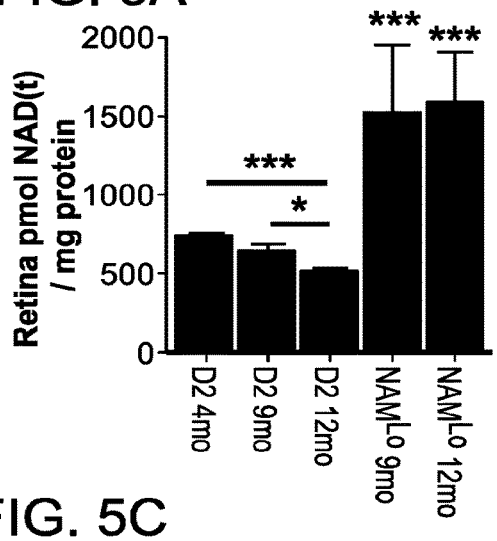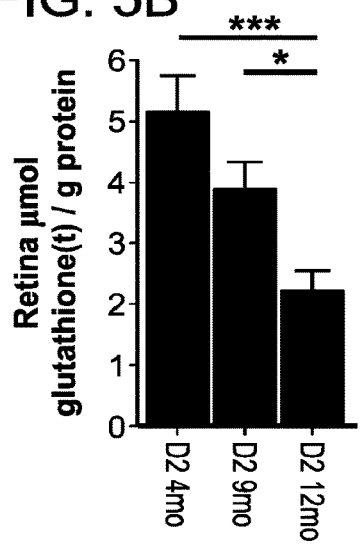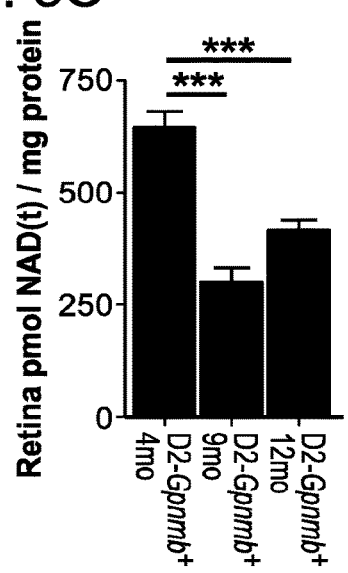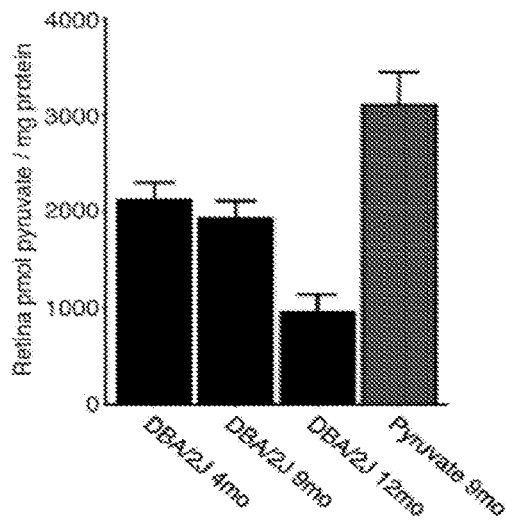

TREATMENT AND PREVENTION OF OCULAR NEURODEGENERATIVE DISORDER

REFERENCE TO RELATED APPLICATION

This application is a continuation application of U.S. patent application Ser. No. 15/959,379, filed on Apr. 23, 2018, which is a continuation application of the International Patent Application No. PCT/US2016/058388, filed on Oct. 24, 2016, and published as WO2017/070647, which claims the benefit of the filing date under 35 U.S.C. § 119 (e) to U.S. Provisional Application No. 62/245,467, filed on Oct. 23, 2015, and 62/366,211, filed on Jul. 25, 2016, the entire contents of each of which are hereby incorporated by reference in their entirety.

STATEMENT REGARDING FEDERALLY SPONSORED RESEARCH

The present invention was made with U.S. government support under Grant No. R01 EY011721, awarded by the National Institute of Health (NIH). The U.S. government has certain rights in the invention.

BACKGROUND OF THE INVENTION

Axon injury is an early event in neurodegenerative diseases. Neurodegenerative diseases are characterized by a dysfunction or loss of viable nerve cells from either the peripheral or the central nervous system. In many cases axon degeneration is shown to precede neural loss, which is a process that is invariably more pronounced at the distal rather than the proximal end of axonal processes. Upstream molecular signals that trigger the neurodegeneration cascades in the neuron remain unknown.

There are reports suggesting the use of nicotinamide adenine dinucleotide (NAD) and its related compounds to reduce axon degeneration. For example, US 2006-0211744 A1 (the '744 application) describes the use of agents, including NAD, NADH, and nicotinamide (NAM), to reduce chronic neural degeneration. Using a cell culture model of transected dorsal root ganglion (DRG) neuron axon, the '744 application discloses that NAD provided a protecting effect to these neuron against axon degeneration. The '744 application further discloses that NAM reduces neural degeneration in mouse model for Experimental Autoimmune Encephalomyelitis (EAE), Amyotrophic Lateral Sclerosis (ALS), and Relapsing Remitting Multiple Sclerosis (RRMS). U.S. Pat. No. 7,776,326 (the '326 patent) discloses a method of treating axonal degradation in neuropathic diseases in mammals by administering agents that increases NAD activity in the injured neurons. Using primary cell cultures of dorsal root ganglion (from spinal nerves) and axotomy (mechanical cut) at a location close to soma, the '326 patentees explicitly concluded that nicotinic acid and NAM did not work to diminish axonal degeneration. In an eye injection study, the '326 patentees again stated that, when injected intravitreally, NAM did not show any difference from the control animals.

Glaucoma is one of the most common neurodegenerative diseases, and represents the leading cause of irreversible blindness, affecting over 70 million people worldwide (Quigley and Broman, *Br J Ophthalmol* 90, 262-267, 2006), especially in the elderly. Glaucoma is a complex, multifactorial disease characterized by the progressive dysfunction and loss of retinal ganglion cells (RGCs) leading to vision loss. High intraocular pressure (IOP) and increasing age represent susceptibility factors for neurodegeneration for glaucoma. Recent advances have hinted to a variety of molecular changes occurring in glaucomatous tissues at the early stages of disease (Howell et al., *Journal of Clinical Investigation* 121, 1429-1444, 2011; Nickells et al., *Annu Rev Neurosvi* 35, 153179, 2012). Early cellular and molecular mechanisms that initiate glaucomatous damage within RGCs are poorly known. It appears that the RGCs are insulted at multiple sites very early in glaucoma including changes affecting their cell bodies, dendrites and synapses in the retina as well as their axons in the optic nerve. The mechanism how high IOP and aging drive neuronal vulnerability and initiate glaucoma in humans is still unclear.

Although there are available strategies to alleviate elevated IOP, there are no effective treatments or preventive measures targeting ocular neural degeneration. Accordingly, there is a continuing need in deciphering the upstream molecular signals that trigger the initial neurodegenerative process as well as identifying new molecular targets, so as to provide therapeutic interventions for reducing RGC damage in the retina and axon degeneration, particularly in the treatment of glaucoma.

SUMMARY OF THE INVENTION

The present invention is primarily predicated on our finding that there is potential effect of nicotinamide (NAM) or pyruvate, or a combination thereof, to protect neuronal cell body, axon, and an associated cell type, thus being beneficial to the treatment of neurodegeneration (e.g., axon degeneration) and ocular neurodegeneration diseases (e.g., glaucoma).

It is an object of the present invention to provide a method of treating or preventing glaucoma, comprises the step of administering to a subject in need of treatment of a pharmaceutical composition comprising a therapeutic effective amount of NAM and/or pyruvate.

It is an object of the present invention to provide a method of lowering intraocular pressure, e.g., in glaucoma, comprises the step of administering to a subject in need of treatment of a pharmaceutical composition comprising a therapeutic effective amount of NAM and/or pyruvate.

It is an aspect of the present invention to provide a method of improving visual function in patients having or suffering from glaucoma, comprises the step of administering to a subject in need of treatment of a pharmaceutical composition comprising a therapeutic effective amount of NAM and/or pyruvate.

The present therapy treatment (medicaments and/or gene therapy), without being hound by a particular theory, is believed to work by lowering the intraocular pressure by two main mechanisms: 1) reducing aqueous humor production, and/or 2) increasing aqueous humor outflow. The present therapy can serve as an effective treatment by lowering the high IOP, thus preserving the axon such as optic nerve, and preventing the subsequent loss of visual function.

The present therapy treatment is useful to treat or prevent neurodegeneration in glaucoma.

The present glaucoma treatment is effective in treating or preventing neural dysfunction and neurodegeneration at the level of retina (e.g., RGCs). Glaucoma can exist at any levels of intraocular pressure (high IOP or normal IOP). The present therapy treatment provides an IOP-independent effect of neuroprotective effect on retinal cells such as the retinal ganglionic cells (RGCs).

In certain embodiments, the present treatment prevents and/or delays the progression of glaucoma (e.g., primary open angle glaucoma or POAG) via reducing the intraocular pressure. Almost all current strategies for treating glaucoma are aimed at lowering or preventing a rise in IOP.

In certain embodiments, the present treatment prevents and/or delays the progression of glaucoma (e.g., primary open angle glaucoma or POAG) via both providing direct neuroprotection and reducing the intraocular pressure. The present therapy provides an unexpected dual benefit in the treatment of glaucoma.

In certain embodiments, the present treatment prevents and/or delays the progression of glaucoma without reducing intraocular pressure. Thus the present therapy method provides an unexpected advantage, in that the medicament and/or gene therapy offers an IOP-independent neuroprotective effect.

The present therapy method provides a treatment for glaucoma, such as primary open angle glaucoma, by protecting optic nerve changes, and characteristic patterns of visual field loss. According to the Preferred Practice Patterns of AAO, two of the three findings (elevated IOP, optic nerve damage, or visual field loss) must be present for the diagnosis of primary open angle glaucoma.

It is an object of the invention to provide a method of treating a neurodegenerative disorder (such as an ocular neurodegenerative disease, e.g., glaucoma) in a subject in need thereof, the method comprising administering to the subject a therapeutically effective amount of a pharmaceutical composition comprising one or more compounds that increase intracellular level of NADt, or that increases intracellular level of $NAD^+$, NADH, GSH, GSSG, PQQ, or pyruvate.

In certain embodiments, the neurodegenerative disorder (such as the ocular neurodegenerative disease, e.g., glaucoma) involves axon degeneration, neuronal dysfunction, somal shrinkage, synapse loss, dendritic atrophy, and/or normal neuronal aging. In certain embodiments, the neurodegenerative disorder (such as the ocular neurodegenerative disease, e.g., glaucoma) involves axon degeneration.

In certain embodiments, the neurodegenerative disorder (such as the ocular neurodegenerative disease, e.g., glaucoma) involves Wallerian degeneration, Wallerian-like degeneration or dying back axon degeneration. For example, the Wallerian degeneration results from neuronal injury. The neuronal injury may result from disease, trauma, a chemotherapeutic agent, or neuronal aging.

In certain embodiments, the neurodegenerative disorder is one or more of Alzheimer's disease, multiple sclerosis, diabetic neuropathy, traumatic brain injury, ischemia, peripheral neuropathy, or an ophthalmic disorder such as glaucoma or an age-related ocular disease (e.g., age-related macular degeneration (AMD), Leber's optic neuropathy, dominant optic atrophy, cataract, diabetic eye disease/diabetic retinopathy, retinal degeneration, dry eye, low vision).

In certain embodiments, the compounds of the present invention comprise a nicotinamide adenine dinucleotide ($NAD^+$) precursor (e.g., nicotinic acid (Na), nicotinamide (NAM), nicotinamide mononucleotide (NMN), nicotinamide riboside (NR), or a combination thereof).

In certain embodiments, the compounds of the present invention include nicotinamide, pyruvate, or pyrroloquinoline quinone (PQQ). The compounds of the present invention are believed to replenish intracellular NADt or improve the mitochondrial electron transport chain.

In certain embodiments, the compounds of the present invention include: (a) NAM; (b) pyruvate; (c) PQQ; (d) NAM and pyruvate; (d) NAM and PQQ.

It is an object of the invention to provide a method of treating a neurodegenerative disorder (such as the ocular neurodegenerative disease, e.g., glaucoma) in a subject in need thereof, the method comprising administering to the subject a gene composition. The gene composition contains a gene that increases the expression of (e.g., Nmnat-1, Nmnat-2, or Nmnat-3).

In certain embodiments, the gene is NMNAT1.

In certain embodiments, the gene is $Wld^S$.

In certain embodiments, the method comprises administering a polynucleotide encoding Nmnat (e.g., Nmnat-1 Nmnat-2, or Nmnat-3) and/or $Wld^S$ to the eye of a subject.

In certain embodiments, the polynucleotide is administered to the subject locally.

In certain embodiments, the polynucleotide is administered to the subject on a viral vector (e.g., an AAV vector, an adenoviral vector, a lentiviral vector, a retroviral vector, etc.).

In certain embodiments, the neurodegenerative disorder is glaucoma or an age-related ocular disease; the subject is a human.

It is an object of the invention to provide a method of treating a neurodegenerative disorder in a subject in need thereof, the method comprising administering to the subject a therapeutically effective amount of one or more compounds that increase intracellular level of NADt, and further comprises administering a polynucleotide encoding and expressing Nampt, Nmnat (e.g., Nmnat-1), and/or $Wld^S$ to the subject.

It is an objective of the invention to provide a method of treating glaucoma in a subject in need thereof, comprising the step of administering to the subject a pharmaceutical composition containing a therapeutically effective amount of nicotinamide (NAM), thereby treating glaucoma.

It is a further related but distinctive objective of the invention to provide a method of preventing glaucoma in a subject in need thereof, comprising the step of administering to the subject a pharmaceutical composition containing a therapeutically effective amount of nicotinamide (NAM), thereby preventing glaucoma.

In certain embodiments, said NAM is present in a therapeutically effective amount to reduce neurodegeneration in a retinal ganglion cell. For example, in certain embodiments, said pharmaceutical composition contains about 0.5-10 grams NAM, about 1-5 grams NAM, or about 2.5 grams NAM for daily consumption.

In certain embodiments, said NAM is present in a therapeutically effective amount to reduce intraocular pressure. For example, in certain embodiments, said pharmaceutical composition contains about 2-25 grams NAM, about 10-20 grams NAM, or about 10 grams NAM for daily consumption.

In certain embodiments, said pharmaceutical composition further comprises pyruvate. Preferably, said NAM and pyruvate are present in therapeutically effective amounts to reduce neurodegeneration in a retinal ganglion cell. For example, in certain embodiments, said pharmaceutical composition independently contains (1) about 0.5-10 grams NAM, about 1-5 grams NAM, or about 2.5 grams NAM for daily consumption; and (2) about 0.5-10 grams pyruvate, about 1-5 grams pyruvate, or about 2.5 grams pyruvate for daily consumption. Preferably, said NAM and pyruvate are present in therapeutically effective amounts to reduce intraocular pressure. For example, in certain embodiments, said pharmaceutical composition independently contains (1) about 2-25 grams NAM, about 10-20 grams NAM, or about 10 grams NAM for daily consumption; and (2) about 2-25 grams pyruvate, about 10-20 grams pyruvate, or about 10 grams pyruvate for daily consumption.

In certain embodiments, said pharmaceutical composition further comprises one or more compounds selected from the group consisting of: nicotinamide mononucleotide (NMN), pyrroloquinoline quinone (PQQ), nicotinamide adenine dinucleotide (NAD), and nicotinamide ribose (NR). In certain embodiments, when PQQ is present, the pharmaceutical composition comprises about ~10 mg-10 g, about 50 mg-1 g, or about 500 mg PQQ for daily consumption.

In certain embodiments, the present method (with or without pyruvate) further comprises the step of administering a gene composition, wherein said gene composition comprises a polynucleotide encoding NMNAT1. In certain embodiments, the polynucleotide is in a viral vector, such as an adeno-associated virus (AAV) vector, an adenoviral vector, a lentiviral vector, or a retroviral vector.

In certain embodiments, said viral vector is AAV. In certain embodiments, said viral vector is AAV2.2. In certain embodiments, said viral vector is a lentiviral vector.

In certain embodiments, said gene composition is administered intravitreally intraocularly. Preferably, said gene composition is administered intravitreally.

In certain embodiments, said subject is a human subject.

In certain embodiments, said subject has an intraocular pressure of about 12-21 mmHg. In certain embodiments, said subject has an intraocular pressure of greater than 21 mmHg.

In certain embodiments, said subject has not developed neurodegeneration symptoms of glaucoma. In certain embodiments, said subject has developed neurodegeneration symptoms of glaucoma.

In certain embodiments, said subject has developed visual dysfunction.

In certain embodiments, the method further comprises administering to the subject an additional therapeutic agent. An exemplary additional therapeutic agent includes an intraocular pressure lowering agent. In certain embodiments, said additional therapeutic agent is a beta blocker, a nonselective adrenergic agonist, a selective α-2 adrenergic agonist, a carbonic anhydrase inhibitor, a prostaglandin analog, a para-sympathomimetic agonist, a carbachol or a combination thereof. In certain embodiments, said additional therapeutic agent is timolol, levobunolol, metipranolol carteolol, betaxolol, epinepherine, apraclonidine, brimonidine, acetazolamide, methazolamide, dorzolamide, brinzolamide, latanoprost, travaprost, bimataprost, pilocarpine, echothiophate iodine, carbachol, or a combination thereof.

It is yet an objective of the invention to provide a method of improving visual function in a subject in need thereof, comprising the step of administering to the subject a pharmaceutical composition containing a therapeutically effective amount of nicotinamide (NAM), thereby improving visual function.

In certain embodiments, said pharmaceutical composition further comprises pyruvate.

In certain embodiments, the method further comprises the step of administering a gene composition, wherein said gene composition comprises a polynucleotide encoding NMNAT1.

It should be understood that all embodiments described herein can be combined with any other embodiment unless explicitly disclaimed.

BRIEF DESCRIPTION OF THE DRAWINGS

FIGS. 4A and 4B show that 9-month old D2 mice have decreased cristae volume in RGC somal and dendritic mitochondria. However, there is no significant difference in total mitochondrial size/volume. Scale bar=350 nm. **=P<0.01, *=P<0.001.

FIG. 5A shows that NAD(t) levels are increased in NAM$^{Lo}$-treated (550 mg/kg/day) D2 mice (n=22/group). *=P<0.05, ***=P<0.001.

FIG. 5B shows that GSH/GSSG levels decrease with age (n=22/group). *P<0.05, ***=P<0.001.

FIG. 5C shows that NAD(t) levels also decrease with age in D2-Gpnmb$^+$ control mice (n=22/group). ***=P<0.001.

FIG. 5D shows a decrease in pyruvate levels with age that is restored by pyruvate treatment. D2 mice were treated with 500 mg/kg/d pyruvate in normal drinking water from 6-month of age.

In FIG. 21F, Red=highest expression, blue=lowest expression. I-V=mitochondrial complexes I-V (tabulated in Table 1), G=D2-Gpnmb$^+$, 1-4=D2 Groups 1-4, N=NAM.

FIG. 24A shows that Nmnat1 overexpression prevents RGC soma loss and loss of anterograde axoplasmic transport (n=10/group), as demonstrated in FIG. 12A. Scale bar is 50 μm in FIG. 24A, and is 100 μm in FIG. 24B.

FIG. 27A shows forward and sideward scatter (see FIG. 27A insert and FIG. 27B) that are gated to identify live cells (FIG. 27B insert). RGCs were identified as gated Thy1.2⁺ (Cd11b⁻, Cd11c⁻, Cd31⁻, Cd34⁻, Cd45.2⁻, GFAP⁻, DAPI⁻) events. Only Cd11b, Cd45, and Thy1.2 plots are shown (FIGS. 27C and 27D. In FIG. 27E, FACS positive RCGs were plated and stained with SNAP-25 and β-tubulin to confirm RGC status. Scale bar=25 µm.

DETAILED DESCRIPTION OF THE INVENTION

Definitions

Figure 1:
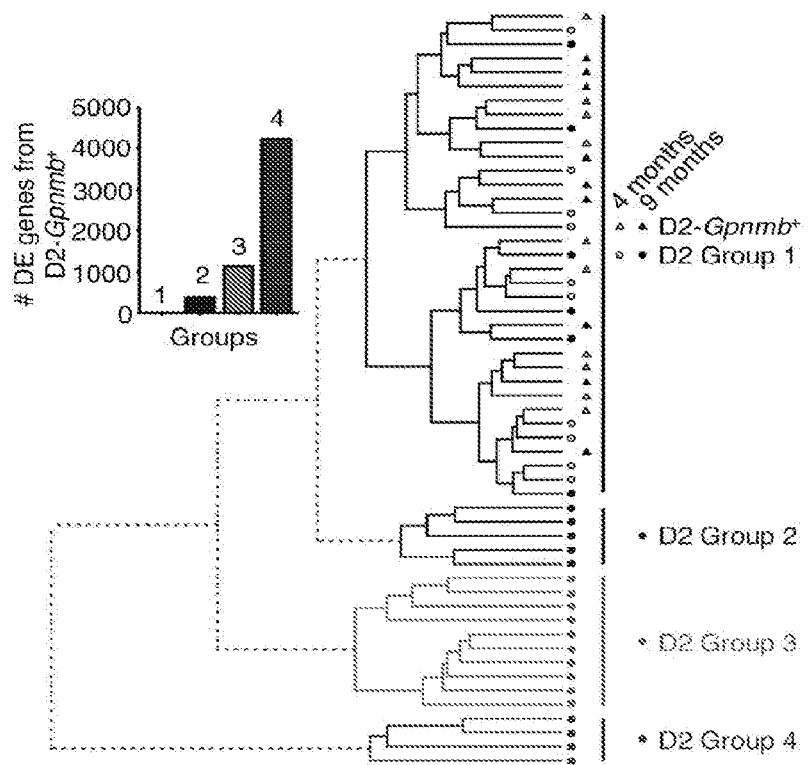
FIG. 1 shows results of Hierarchical Clustering (HC), for defining molecularly determined stages of glaucoma in DBA/2J (D2) mice at initial stages of disease and morphologically indistinguishable from age-matched D2-Gpnmb$^+$ or young controls, HC was based on RNA-sequencing in the retinal ganglion cells (RGCs) isolated from the D2 mice and the controls. HC allows the clustering of the RGC samples into distinct groups with control and young samples being molecularly similar (Spearman's rho). Circles=samples from D2 RGCs, triangles=samples from D2-Gpnmb$^+$ RGCS. Inset: number of differentially expressed (DE) genes (q<0.05) between D2-Gpnmb$^+$ and each group.

The terms used in this application shall have the following meanings.

As used herein, the term "glaucoma" refers to an eye disease that results in damage to the retina and optic nerve and visual dysfunction or vision loss. Glaucoma occurs more commonly among older people. Vision loss from glaucoma is permanent and is irreversible.

As used herein the term "a subject/patient in need of treatment thereof" is generally understood to be a person that suffers from certain neurodegeneration diseases or conditions, especially from ocular neurodegeneration including glaucoma, or just feels to be in need for such treatment.

As used herein, the term "glaucoma" encompasses primary open angle glaucoma, secondary open angle glaucoma, normal tension glaucoma, hypersecretion glaucoma, primary angle-closure glaucoma, secondary angle-closure glaucoma, plateau iris glaucoma, pigmentary glaucoma, combined-mechanism glaucoma, developmental glaucoma, steroid-induced glaucoma, exfoliation glaucoma, amyloid glaucoma, neovascular glaucoma, malignant glaucoma, capsular glaucoma, plateau iris syndrome, and the like.

As used herein, the term "normal intraocular pressure (normal "IOP")" in humans refers to a human subject having an IOP values of 10 mmHg to 21 mmHg. Some individuals, however, may develop optic nerve damage despite a normal IOP (known as normal-tension glaucoma).

As used herein, the term "high intraocular pressure" (high IOP) in humans refers to a human subject having an IOP value greater than or equal to 21 mmHg (or 2.8 kPa). High IOP is known to be a risk factor for glaucoma. Some individuals, however, may have high IOP for years and never develop optic nerve damage.

As used herein, the term "neuroprotective" or "neuroprotection" refers to the ability to protect neurons, their synapses, dendrites, somas, or axons in the ocular nerve (e.g., optic nerve), central or peripheral nervous system from damage (including functional dysfunction) or death, or to delay the onset of neuronal damage or death, or alleviate the severity of the neuronal damage extent of death among a population of neurons.

As used herein, the term "preventing" or "prevention" with respect to, for example, neuronal damage or death in general or ocular neurodegeneration disease (e.g., glaucoma) in particular, refers to the ability of the compounds or agents of the present invention to confer neuroprotection, preferably before such damage, death, or disease occurs. Thus prevention of glaucoma includes avoiding the development of glaucoma, reducing the risk or chance of eventually developing glaucoma, delaying the onset or progression of glaucoma, or reducing the severity of neuronal damage/extent of neuronal death/loss among a population of neurons should glaucoma eventually develop.

As used herein, the term "treating" or "treatment" includes the administration of the compounds or agents of the present invention to a subject to alleviate, arrest, or inhibit development the symptoms or conditions associated with neurodegeneration, such as glaucoma.

As used herein, "improving vision or visual function" refers to the effect of the compounds or agents of the present invention in improving vision or a visual function (such as a visual field test or pattern electroretinography (PERG) amplitude of RGC) in a subject administered with such compounds or agents, as compared to a control subject not administered with such compounds or agents.

As used herein, the term "therapeutically effective amount" means the amount that, when administered to a subject, produces effects for which it is administered. For example, a "therapeutically effective amount," when administered to a subject to inhibit neurodegeneration, reduced IOP elevation, and/or improves RGC function (e.g., prevents the worsening of RGC function).

As used herein, the term "subject" or "patient" are used interchangeably and refer to mammals such as rodent, dog, and human. Accordingly, the term "subject" or "patient" as used herein means any mammalian patient or subject (e.g., human) to which the compounds of the invention can be administered.

As used herein, the term "medicament" or "pharmaceutical composition" refers to a pharmaceutical formulation that is of use in treating, curing or improving a disease or in treating, ameliorating or alleviating the symptoms of a disease.

As used herein, the term "expression vector" refers to a nucleic acid molecule that is capable of effecting expression of a gene/nucleic acid molecule it contains in a cell compatible with such sequences. The expression vectors typically include at least suitable promoter sequences and optionally, transcription termination signals.

The following abbreviations are used:
NAM—nicotinamide
NAMPT—nicotinamide phosphoribosyl transferase
NMN or β-NMN—nicotinamide mononucleotide
NMNAT—nicotinamide mononucleotide adenylyl transferase
NAD—nicotinamide adenine dinucleotide
NaMN—nicotinic acid mononucleotide
NR—nicotinamide riboside

Overview

The present invention is primarily based on the use of a state-of-the-art molecular technology (RNA-sequencing; RNA-seq) on retinal ganglion cells (RGCs), which led to the discovery that mitochondrial abnormalities are an early driver of neuronal dysfunction, occurring at a time that is prior to detectable neural degeneration. Using the DBA/2J (D2) mouse model (a chronic age-related, inherited glaucoma), the present inventors further uncovered the relationship between increasing age, a key risk factor for most glaucoma, and high IOP in driving the neuronal degeneration in RGCs.

The present inventors developed a method of delivering to retina a therapeutic level of nicotinamide adenine dinucleotide (NAD⁺) to supplement the declining level of NAD⁺. The administration of specific pharmaceutical composition of the invention (e.g., NAM and/or pyruvate) represents a novel approach in the treatment of ocular neurodegeneration and glaucoma. The present therapeutic method may be useful in treating other neurodegeneration including decreases where aging neurons are vulnerable to disease-related insults.

In one aspect, the present invention provides a therapeutic use of targeted pharmaceutical compositions to treat or prevent age-dependent neurodegenerations, e.g., to treat or prevent glaucoma.

In certain embodiments, the pharmaceutical composition is effective in treating or preventing glaucoma, preferably primary open angle glaucoma, normal tension glaucoma, and primary angle-closure glaucoma. In certain embodiments, the pharmaceutical preparation of the present invention is particularly effective for treating or preventing primary open angle glaucoma.

In certain embodiments, the method involves administering to a subject in need of treatment/prevention of neurodegenerative disorder (e.g., glaucoma) a therapeutic effective amount of nicotinamide (NAM).

In certain embodiments, the subject is administered with NAM in combination with pyruvate. It is believed that the NAM and/or pyruvate increase intracellular level of NADt (total level of $NAD^+$ and NADH) and thus treats or prevents the neurodegenerative disorder in the subject.

In one aspect, the present invention provides a therapeutic use of gene delivery to increase intracellular nicotinamide adenine dinucleotide to prevent neurodegeneration and thereby treat glaucoma.

In certain embodiments, the present invention provides a method of gene therapy (e.g., driving expression of nicotinamide nucleotide adenylyltransferase 1 (Nmnat1). The expression of Nmnat1 protein was found to be profoundly protective and acts synergistically with NAM (i.e., 84% of eyes having no glaucomatous neurodegeneration).

An advantage of the present invention is to reduce risk factor of dedeveloping glaucoma. The present studies clearly show that NAM, alone or in combination with other agents (such as pyruvate), reduces risk factors for glaucoma. In control D2 mice at 12 months of age, about 60% of nerves have severe glaucoma. This represents a 0.6 risk factor of developing glaucoma. Following low dose NAM administration (550 mg/kg/day in mice), this risk factor is reduced to 0.36 (~2-fold drop in risk factor), or to 0.06 when high dose NAM (2,000 mg/kg/day in mice) is administered (a 10-fold decrease in risk factor).

An advantage of the present invention is the synergistic effect between NAM and administration of gene therapy (e.g., NMNAT1 gene therapy). In comparison to gene therapy that alone reduces the risk factor to 0.29 (~2 fold decrease in risk factor), gene therapy in combination with NAM reduces the risk factor to 0.16 (~4 fold decrease in risk factor). Thus NAM and gene therapy in combination synergistically reduces the risk factor of developing glaucoma following elevated IOP.

The present finding of a protective effect for NAM (alone or in combination with other agents such as pyruvate) is unexpected. The present finding is in sharp contrast to that reported in the '326 patent which states that NAM has no protective effects.

There are at least the following reasons that provides the basis for the different findings. The first reason is that the '326 patentees used an experimental system that bears little relevance to in vivo effect, especially in ocular-associated diseases such as glaucoma. In their experiments, the '326 patentees isolated the dorsal root ganglia (DRG) neurons and induced neural damage by cutting their neuritis. This artificial culture-induced neural injury where the mechanical cut occurred very close to the DRG neuron cell body hardly resembles the neurodegeneration in vivo. It is recognized that initial axon damage in glaucoma occurs at a much greater distance from the soma than the DRG neuritis. The second reason is that the '326 patentee culture system did not use retinal ganglion cells (RGCs), which are highly relevant neuron in glaucomatous neurodegeneration. The third reason is that the '326 patentees used an artificial cell system instead of an intact neural tissue (that is composed of various cell types that communicate with and support each other).

Lastly, the '326 patentees mentioned an in vivo complete optic nerve transection model, in which the nerve (including its surrounding sheathe) is mechanically cut. This suddenly damages the nerve and substantially alters the local environment in which the axons reside which, within 14 days, causes the death of >90% of retinal ganglion cells (see www.ncbi.nlm.nih.gov/pubmed/21610673). Although the insult is in the correct place on the nerve, there are not cases of glaucoma. Overall, the approach adopted by the '326 patentees is a very artificial and rapid method of destroying retinal ganglion cells that does not recapitulate human glaucoma. Of interest is that, in their optic nerve transection experiments, the '326 patentees intravitreally inject compounds (including NAM) to drive the production of NAD in the eye, and the '326 patentees explicitly concluded that NAM is not protective against axon degeneration in RGCs in this model.

All of this is of particularly relevance. Our culture experiments are more relevant to glaucoma as we used intact retinal tissue that included retinal ganglion cells in the their normal relationship to other retinal cell types, and the retinal ganglion cell axons were cut at the same location as damage occurs in glaucoma. It is believed that the damage in glaucoma occurs in true axons in the optic nerve head where the RGC axons exit the eye and becomes the optic nerve.

In contrast, the data presented in this application clearly shows the neuroprotective effect of NAM in glaucoma. The present use of the NAM, alone or in combination with other agents (e.g., pyruvate), affords a neuroprotective effect in ocular-associated diseases such as glaucoma. In the present application, the neuroprotective effects are evidenced by at least one of the following parameters: (i) prevention of soma loss (RBPMS staining); (ii) prevention of retinal thinning and nerve fiber layer loss (Nissl staining); (iii) prevention of optic nerve degeneration and axon loss (PPD staining); (iv) prevention of loss of anterograde axoplasmic transport (Ct-B staining); (v) prevention of loss of visual function (PERG); (vi) prevention, of abnormal mitochondrial cristae (EM); (vii) reduction of fat droplets (Oil Red O staining); and (viii) reduction of PARP activation (PARP staining).

The present inventors further discovered that the use of NAM, alone or in combination with other agents (e.g., pyruvate), affects intracellular events to provide a neuroprotective effects as evidenced by: (i) reduction of HIF-1α activation (HIF-1α staining); (ii) reduction of synapse loss (SNAP-25 staining); (iii) restoration of nuclear to mitochondrial transcript abundance (RNA-seq); and (iv) prevention of age-related molecular/gene changes (RNA-seq).

Another advantage of the present invention is the combined use of NAM and gene therapy in delivering NAD. The gene therapy approach is believed to last for at least 3-5 years as evidenced by many clinical studies have indicated. The gene therapy affords a synergistic neuroprotective effect with NAM and/or pyruvate in glaucoma as well as lowering IOP.

With the inventions generally described above, the following sections provide more detailed descriptions for further aspects of the invention.

DBA/2J Mouse Model

The present inventors chose to use of DBA/2J (D2) mouse model because this mouse strain develops an inherited age-related glaucoma that highly mimics human glaucoma. D2 mice are one of the most studied models of glaucoma with many established similarities to human glaucoma, including induction of the same disease mediating molecules (for example complement component molecules), the same location of a key glaucoma insult in the optic nerve head, and the same topographical pattern of RGC death as occurs in human glaucoma. The D2 mice have iris disease and high intraocular pressure starting at about 6-8 months of age. By 9 months of age, high ocular pressure has been ongoing in the eyes of the majority of the D2 mice. The D2 mice subsequently have a progressive vision loss, optic nerve damage, and inner retina dysfunction. At 12 months of age, when designed experiments typically end, ~70% of the D2 mice eyes have a severe disease based on histological examination of the retina and optic nerve. glaucoma. Topical administration of compounds (e.g., memantine, timolol, or Latanoprost) lowers IOP in D2 mice and reduces the risk of developing neurodegeneration as they do in human glaucoma. Control D2-Gpnmb$^+$ is an age- and strain-matched mice that do not develop glaucoma.

Ocular Pressure in Glaucoma

Intraocular pressure (IOP) can be determined using, for example, Goldmann applanation tonometry (Haag Streit, Bern, Switzerland). In humans, normal IOP is 12-21 mmHg. IOP that exceeds 21 mmHg is considered high. Elevated IOP is a major risk factor in glaucoma. Of those with POAG (primary open angle glaucoma, the most common glaucoma accounting for >90% of cases), 25 mmHg is the median untreated baseline IOP.

The Baltimore eye study (www.ncbi.nlm.nih.gov/pub/12049574) reported that high risk=IOP>25.75 mmHg; moderate risk=IOP 23.75-25.75 mmHg; and low risk=IOP <23.75 mmHg. Lowering IOP by 20% to a level below 24 mmHg decreases risk of progression from 9.5% to 4.4% at 5 years. The chance of blindness in 1 eye is 27% after 10 years post diagnosis, and 38.1% after 20 years. The chance of blindness in both eyes is 6% and 13.5% respectably.

In human glaucoma patients, such as primary open agent glaucoma (POAG) patients, glaucoma is asynchronous and age-related (most commonly occurring at >40 years old). Untreated glaucoma takes on, average, 14 years to progress from early to late stage disease when IOP is 21-25 mmHg. This rate of progression rapidly increases as IOP increases (~3 years to progress from early to late stage disease when IOP>30 mmHg).

In human patients, treatments that lower IOP (surgical or pharmacological) reduce the risk of developing neurodegeneration. The rates of disease progression and percentage chance of going blind are likely misrepresented due to patients not being diagnosed. It is generally believed that high IOP does not always indicate glaucoma (~30% blind after 10 years, ~40% after 20). Lowering IOP does not cure glaucoma, but does reduce the risk factor by 58%. Despite the conventional IOP lowering preventions, there is still a risk of vision loss, and even blindness. There are limited available neuroprotective strategies in glaucoma. Vision loss in glaucoma is irreversible. In fact, glaucoma is the leading case of irreversible blindness in the world.

Retinal Ganglion Cells (RGCs)

Retinal ganglion cells (RGCs) are the output neuron of the retina. They receive visual information from the photoreceptors (i.e., rods and cones) via intermediate neurons (i.e., bipolar cells and amacrine cells). This visual information starts as the photons in light, and culminates in an electric potential at retinal ganglion cell synapses. RGCs have long axons that leave the cell body and traverse across the retina to the optic disc (i.e., blind spot) where they exit out of the eye (optic nerve head). Just beyond the optic nerve head (myelin transition zone), retinal ganglion cell axons become myelinated and form the optic nerve (i.e. the optic nerve is a bundle of retinal ganglion cell axons, in the mouse this is ~50,000 depending on the strain). Axons in the optic nerve eventually reach terminal visual centers in the brain that then relay these signals on or process this information themselves. Two important visual centers that retinal ganglion cell axons terminate in are the lateral geniculate nucleus (LGN) and the superior colliculus (sup. col./SC).

Retinal ganglion cells are specifically affected (i.e., cell loss) in glaucoma. Damage to the RGCs likely occurs at the axon at the site of optic nerve head. It is speculated that because of the stress induced on the eye by abnormally high IOP, the optic nerve head is a "weak spot" in the eye where mechanical insults to the retinal ganglion cell axon may occur. The axon is not the only point of insult in the retinal ganglion cell, as pressure throughout the eye also must affect the soma and dendrites as well. The exact underlying mechanism of how RGCs damage is not totally clear.

In the DBA/2J (D2) mice, the present inventors showed that at time-points where IOP is high, there is no detectable axon loss in the optic nerve no ocular neurodegeneration). Surprisingly, the present inventors discovered that there are early mitochondrial and molecular changes, dendrite atrophy, and synaptic loss. This finding suggests that the effects of IOP manifest in other compartments of the retinal ganglion cell, not just the axon in the optic nerve.

Neurodegeneration Treatment

In certain embodiments, the agent comprises a nicotinamide adenine dinucleotide (NAD$^+$) precursor (e.g., nicotinic acid, nicotinamide (NAM), nicotinamide mononucleotide (NMN), nicotinamide riboside (NR), or a combination thereof), a Krebs Cycle intermediate or precursor thereof (e.g., pyruvate), or a combination thereof.

In certain embodiments, the agent comprises a nicotinamide adenine dinucleotide (NAD$^+$) precursor, e.g., nicotinic acid, nicotinamide (NAM), nicotinamide mononucleotide, nicotinamide riboside, or a combination thereof. In certain embodiments, the NAD$^+$ precursor is nicotinamide or nicotinamide riboside.

Nicotinic acid (also known as niacin, nicotinate, vitamin B3, and vitamin PP) is a vitamin. Its corresponding amide is called nicotinamide or niacinamide. These vitamins are not directly interconvertable; however, both nicotinate and nicotinamide are precursors in the synthesis of redox. pairs NAD$^+$/NADH (nicotinamide adenine dinucleotide) and NAD$^+$/NADH (nicotinamide adenine dinucleotide phosphate). The nicotinate and nicotinamide metabolic pathway can be referred to herein as the NAD$^+$ synthesis pathway.

NAD$^+$ is synthesized through two metabolic pathways: a salvage pathway and a de novo pathway. In the salvage pathway, NAD$^+$ can be synthesized from external sources of precursor compounds (e.g., nicotinic acid, nicotinamide, nicotinamide riboside, etc.). In the de novo pathway, NAD$^+$ can be synthesized from quinolinate produced during the metabolism of amino acids (e.g., tryptophan, aspartate, etc.).

NAD$^+$ precursor of the invention includes nicotinic: acid, nicotinamide, nicotinamide riboside, etc., as well as salts thereof, and analogs thereof. In certain embodiments, administering the NAD$^+$ precursor of the invention leads to increased intracellular level of NADt.

In certain embodiments, the agent comprises a Krebs Cycle intermediate or precursor thereof, or a combination thereof. For example, the Krebs cycle intermediate or precursor is Oxaloacetate, Acetyl CoA, Citrate, CoA-SH, cis-Aconitate, D-Isocitrate, $NAD^+$, Oxalosuccinate, NADH, α-Ketoglutarate, Succinyl-CoA, GDP, ubiquinone, Succinate, Fumarate, L-Malate, pyruvate, a monosaccharide (such as glucose, galactose, fructose), a disaccharide (such as sucrose, maltose, lactose), or a combination thereof.

Thus the invention provides pharmaceutical compositions that include nicotinic acid and/or nicotinamide riboside and/or nicotinamide and/or nicotinic acid metabolites. The nicotinic acid and/or nicotinamide riboside and/or nicotinamide and/or nicotinic acid metabolites can be used in free form. The term "free," as used herein in reference to a component, indicates that the component is not incorporated into a larger molecular complex. In some embodiments, the nicotinic acid can be comprised in niacin. The nicotinic acid and/or nicotinamide riboside and/or nicotinamide and/or nicotinic acid metabolites can be in a salt for.

In some embodiments, any of the compositions described herein can include salts, derivatives, metabolites, catabolites, anabolites, precursors, and analogs thereof. For example, the metabolites can include nicotinyl CoA, nicotinuric acid, nicotinate mononucleotide, nicotinate adenine dinucleotide, or nicotinamide adenine dinucleotide. In some embodiments, the compositions comprise nicotinamide. In some embodiments, the compositions can be substantially free of nicotinic acid metabolites.

In certain embodiments, a salt is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, and trifluoroacetate salt.

NAM/nicotinic acid analogs may also be used in the subject invention. Suitable analogues of nicotinic acid include, for example, isonicotinamide and N-methyl-nicotinamide.

In certain embodiments, keto-, ethyl-, benzyl-, or other non-salt embodiments of NAM can also be used in the instant invention.

The toxicity of NAM/nicotinamide/NAD/NR/pyruvate is low, and relatively large amounts may be administered without toxic effect.

In mice, the present compounds (e.g., NAM/nicotinamide/NAD/NR/pyruvate) can be administered with a daily dosage of about 200-1,000 mg/kg/day to provide a neuroprotective effect. Preferably, the daily dosage is about 40-600 mg/kg/day. More preferably, the daily dosage is about 550 mg/kg/day. At these dosages, the present compounds afford a neuroprotective effect.

In mice, the present compounds (e.g., NAM/nicotinamide/NAD/NR/pyruvate) can be administered at a dose of about 1,000-5,000 mg/kg/day to provide an IOP lowering effect. Preferably, the daily dosage is about 1,500-3,000 mg/kg/day. More preferably, the daily dosage is about 2,000 mg/kg/day. At these dosages, the present compounds afford an IOP lowering effect.

With regard to PQQ, it is tolerated at least at 2,000 mg/kg/day in mice. The neuroprotective effect provided by PQQ is about 20-2,000 mg/kg/day, about 100-1,000 mg/kg/day, or about 500 mg/kg/day in mice.

To convert doses of pharmaceutical composition expressed in terms of mg/kg from one species (e.g., mouse) to an equivalent surface area dose expressed as mg/kg in another species (e.g., human), the follow table provides the approximate factors for conversion, based on the assumptions and constants in Freireich et al., *Quantitative comparison of toxicity of anticancer agents in mouse, rat, dog, monkey and man, Cancer Chemother Rep.* 50(4):219-244, 1966 (incorporated herein by reference).

| Equivalent Surface Area Dosage Conversion Factors | | | | | |
|---|---|---|---|---|---|
| | | To | | | |
| | | Mouse (20 gram) | Rat (150 gram) | Monkey (3 kg) | Dog (8 kg) | Human (60 kg) |
| From | Mouse | 1 | ½ | ¼ | ⅙ | 1/12 |
| | Rat | 2 | | ½ | ¼ | 1/7 |
| | Monkey | 4 | 2 | 1 | ⅗ | ⅓ |
| | Dog | 6 | 4 | 1⅔ | 1 | ½ |
| | Human | 12 | 7 | 3 | 2 | 1 |

Thus, a dose of 550 mg/kg in mouse is equivalent (assuming equivalency on the basis of $mg/m^2$) to 550 mg/kg×¼=137.5 mg/kg in monkey, and 550 mg/kg×1/12=45.8 mg/kg in a 60 kg human (or 2.85 g).

The somewhat simplified conversion factors in the table above are based on the body weight to surface area ratio [km] for the respective species. If more precise conversions are desired, the dosage conversion can also be based on the km factors of the respective species listed below.

| Representative Surface Area to Weight Ratios [km] for Various Species | | | |
|---|---|---|---|
| Species | Body Weight (kg) | Surface Area ($m^2$) | km factor |
| Mouse | 0.02 | 0.0066 | 3.0 |
| Rat | 0.15 | 0.025 | 5.9 |
| Monkey | 3.0 | 0.24 | 12 |
| Dog* | 8.0 | 0.40 | 20 |
| Human (Child) | 20 | 0.8 | 25 |
| Human (Adult) | 60 | 1.6 | 37 |

*depending on specific dog breeds, the km factor may be different. For example, in some terriers and other breeds prone to glaucoma, the km factor of about 10 may be used.

Thus, a dose of 550 mg/kg in mouse is equivalent to 550 mg/kg×3.0/37=44.6 mg/kg in a 60 kg adult human (or 2.68 g), and 550 mg/kg×3.0/25=66 mg/kg in a 20 kg human child (or 1.32 g).

The above table can also be used to express a mg/kg dose in any given species as the equivalent mg/sq.m. dose, by multiplying the dose by the appropriate km factor. For example, in adult humans, 100 mg/kg is equivalent to 100 mg/kg×37 kg/sq.m.=3700 mg/sq.m.

In humans (18 60 kg individuals), the present compounds (e.g., NAM/nicotinamide/NAD/NR/pyruvate) can be administered at a daily dosage of 0.5-10 grams to provide a neuroprotective effect. Preferably, the daily dosage is about 1-5 grams/day. Preferably, the daily dosage is about 2-4 grams/day. More preferably, the daily dosage is about 2.5 grams/day. At these dosages, the present compounds afford a neuroprotective effect.

In humans (~60 kg individuals), the present compounds (e.g., NAM/nicotinamide/NAD/NR/pyruvate) can be administered at a daily dosage of about 5-25 grams/day to provide an IOP lowering effect. Preferably, the daily dosage is about 10-20 grams/day. Preferably, the daily dosage is about 8-15 grams/day. More preferably, the daily dosage is about 10 grams/day. At these dosages, the present compounds afford an IOP lowering effect.

In humans (~60 kg individuals), PQQ can be administered at a daily dosage of about 2-160 mg/kg/day, or about 10-100 mg/kg/day, or about 50 mg/kg/day to afford a neuroprotective effect. In certain embodiments, PQQ can be administered at a daily dosage of ~10 mg-10 g a day, about 50 mg-1 g a day, or about 500 mg a day.

Ideally, typical dosing may be once, twice or three times a day. Total daily dose may be administered once, or administered as two or three separate doses (e.g., with each dose being ½ or ⅓ of the daily total). For multiple dosing, each dose can be the same amount or different amounts. The pharmaceutical composition may be administered in the morning or evening. The pharmaceutical composition may be taken with or without meals.

Therapeutic Agent to Treat Neurodegeneration Disorder

In one aspect, the present invention provides a method of treating or preventing a neurodegenerative disorder in a subject in need thereof, the method comprising administering to the subject a therapeutically effective amount of an agent that increases intracellular level of NADt, or that increases intracellular level of $NAD^+$, NADH, GSH, GSSG, pyruvate, or PQQ.

In another aspect, the present invention provides a pharmaceutical composition comprising a therapeutically effective amount of NAM, nicotinamide mononucleotide (NMN or β-NMN), NAD, pyruvate, PQQ or glutathione.

The agent used in the pharmaceutical composition is a neuroprotective agent to treat or prevent such neurodegenerative disorder, such as glaucoma.

Many different types of insults or neurodegenerative diseases or conditions can lead to neuronal damage or death, for example: metabolic stress caused by hypoxia, hypoglycemia, diabetes, loss of ionic homeostasis, physical injury of neurons, exposure to toxic agents and numerous diseases affecting the nervous system including inherited or non-inherited neurodegenerative disorders. In certain embodiments, the neurodegenerative disorder involves axon degeneration. In certain embodiments, the neurodegenerative disorder involves Wallerian degeneration or Wallerian-like degeneration. For example, the Wallerian degeneration may result from neuronal injury, such as injuries resulting from disease, trauma, or a chemotherapeutic agent.

It will be appreciated that this is only an illustrative list. The presence of an agent that is neuroprotective will enable a neuron to remain viable upon exposure to insults or disease conditions which may cause a loss of functional integrity in an unprotected neuron. Such agents may also prevent the neuron from undergoing damage in response to insults by making the neuron more resilient.

Pharmaceutical Composition

A pharmaceutical formulation comprises a pharmacologically active ingredient in a form not harmful to the subject it is being administered to and additional constituents designed to stabilize the active ingredient and affect its absorption into the circulation or target tissue.

The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, PA, 1995.

Suitable pharmaceutical acceptable carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water.

Administration of the pharmaceutical composition according to the invention may be through various routes, for example oral, parenteral (including subcutaneous, intramuscular, intradermal), intravitreal, intraocular (e.g., in the form of eye drops) and the like. In one preferred embodiment, the pharmaceutical composition is for oral administration (including administration of the pharmaceutical composition as part of a drink). In one preferred embodiment, the pharmaceutical composition is for intraocular administration.

Parenteral administration may be performed by subcutaneous, intramuscular, intraperitoneal or intravenous injection by means of a syringe, optionally a pen-like syringe. Alternatively, parenteral administration can he performed by means of an infusion pump. As a still further option, the formulation of the invention can also be adapted to transdermal administration, e.g., by needle-free injection or from a patch, optionally an iontophoretic patch, or transmucosal, e.g., buccal, administration.

The pharmaceutical composition of the invention may be administered in suitable dosage forms, for example, as solutions, suspensions, emulsions, tablets, coated tablets, capsules, hard gelatine capsules and soft gelatine capsules, drops, eye drops, ophthalmic ointments, ophthalmic rinses, injection solution, and the like.

The pharmaceutical composition of the invention may further be compounded in, or attached to, for example through covalent, hydrophobic and electrostatic interactions, a drug carrier, drug delivery system and advanced drug delivery system in order to further enhance stability of the composition, increase bioavailability, increase solubility, decrease adverse effects, achieve chronotherapy well known to those skilled in the art, and increase patient compliance or any combination thereof.

Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate, polymers, polylactic and poly glycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, 1.2 phase and dispersions thereof, well known to those skilled in the art of phase behavior in lipid-water systems, polymeric micelles, multiple emulsions, self emulsifying, self-microemulsifying, cyclodextrins and derivatives thereof, and dendrimers.

The pharmaceutical composition of the current invention may be useful in the composition of controlled, sustained, protracting, retarded, and slow release drug delivery systems. More specifically, but not limited to, the pharmaceutical composition may be useful in the composition of parenteral controlled release and sustained release systems (both systems leading to a many-fold reduction in number of administrations), well known to those skilled in the art. Even more preferably, are controlled release and sustained release systems administered subcutaneously. Without limiting the scope of the invention, examples of useful controlled release system and compositions are hydrogels, oleaginous gels, liquid crystals, polymeric micelles, microspheres and nanoparticles.

Neurodegeneration Diseases

The pharmaceutical compositions of the invention are predicted to be of utility in the treatment of neurodegenerative disorders involving axon degeneration, such as Wallerian degeneration. Examples of disorders where such degeneration may be of importance include diabetic neuropathy, motor neuron disease, multiple sclerosis, peripheral neuropathy, stroke and other ischaemic disorders, traumatic brain injury and the like. This list is for illustrative purposes only and is not limiting or exhaustive.

In certain embodiments, the neurodegenerative disorder is one or more of diabetic neuropathy, traumatic brain injury, ischemia, peripheral neuropathy, or an ophthalmic disorder such as glaucoma. In certain embodiments, the neurodegenerative disorder is glaucoma.

In one embodiment the pharmaceutical composition is intended for use as a neuroprotective medicament in the treatment or prevention of a neurodegenerative disorder resulting from neuronal injury. In a further embodiment the modulator is intended for use as a neuroprotective medicament in the treatment of a neurodegenerative disorder involving axon degeneration (e.g., Wallerian degeneration) resulting from neuronal injury. The term "injury" as used herein refers to damage inflicted on the neuron, whether in the cell body or in axonal or dendritic processes. This can be a physical injury in the conventional sense, i.e., traumatic injury to the brain, spinal cord or peripheral nerves caused by an external force applied to a subject. Other damaging external factors are for example environmental toxins such as mercury and other heavy metals, arsenic, pesticides and solvents. Alternatively, injury can result from an insult to the neuron originating from within the subject, for example: reduced oxygen and energy supply as in ischemic stroke and diabetic neuropathy, autoimmune attack as in multiple sclerosis or oxidative stress and free-radical generation as is believed to be important in amyotrophic lateral sclerosis, injury is also used here to refer to any defect in the mechanism of axonal transport.

In another embodiment, the subject pharmaceutical composition is intended for use as a neuroprotective medicament wherein the neurodegenerative disorder is caused by a neuronal injury resulting from a disease.

In one embodiment, the neuronal injury results from aging.

In one embodiment, the neuronal injury results from trauma. In one embodiment, the disorder is a neuronal injury induced by a chemotherapeutic agent. Certain drugs used in cancer chemotherapy such as Taxol, Velcade and vincristine, cause peripheral neuropathy which limits the maximum doses at which they can be used. Recent studies suggest that neurons suffering from Taxol or vincristine toxicity undergo Wallerian-like changes in their morphology and in the underlying molecular events. Inhibiting Wallerian degeneration could be particularly effective in this condition as neurons are only temporarily exposed to the neurotoxic agent. Simultaneous administration of Taxol or vincristine with an agent inhibiting Wallerian degeneration could therefore allow the drug to be used at substantially higher doses than is currently possible, thus further combating the cancer.

Age is a common risk factor for most glaucoma, the present therapeutic methods offers protection against age-related declines in NAD and protect patients from developing glaucoma (i.e., preventing neurodegeneration). The present provides a combined therapy of administering NAM and/or pyruvate (to replenish NAD levels) as well as gene delivery of NMNAT1 gene. Given the surprising potency of NAM and/or pyruvate and gene therapy, the combined therapy is an attractive approach for treating and preventing glaucoma.

Gene Therapy to Treat Neurodegeneration

Gene therapy is an attractive method for overcoming compliance issues and improving efficacy. The present invention provides a method of gene therapy to treat neurodegeneration. Axon degeneration is an area of unmet therapeutic need. Neurodegeneration causes symptoms in motor neuron disease, glaucoma, Alzheimer's disease, and multiple sclerosis. In diabetes, it causes neuropathic pain and distal sensory loss, which is a leading cause of limb amputation. It is also a dose-limiting side effect in cancer chemotherapy. Progressive axon degeneration due to stretch injury is the major pathology in traumatic brain injury, and failure to protect white matter limits the treatment for stroke. Around half of the human population will eventually suffer one or more of these disorders, which significantly reduces quality of life.

In certain embodiments, the present invention provides a method of treating neurodegeneration in the eye. The present invention provides a method of replacing copies of dysfunctional genes to the eye. Genes are introduced using viral gene delivery. In certain embodiments, the vectors include adenovirus, adeno-associated virus (AAV). In a preferred embodiment, the AAV is AAV2.2. For purposes of this application, it is intended to encompass other AAV serotypes including AAV1, AAV2, AAV4, AAV5, AAV8, AAV9, and the like. In other embodiments, the vector is a Lentivirus, typically a pseudotype HIV-based vector.

To gene deliver targeting RGCs, viral vectors are introduced to the vitreal chamber. In a preferred embodiment, gene delivery is targeted directly proximal to the inner retina. Intravitreal injections are routinely practiced in ophthalmic surgery and can be performed safely in an office/clinic location.

The present invention provides viral gene delivery to the eye as an attractive prospect as it allows a large number of cells to be transfected life-long, delivering a targeted gene product. To the best of the inventors' knowledge, gene therapy in the eye represents a novel approach of glaucoma treatment. Such gene therapy to increase $NAD^+$ applied to human complex diseases such as glaucoma represents a novel approach of treatment.

In one aspect, the present invention provides a method of delivering a gene to an afflicted eye whereby to enhance expression of NAD. In certain embodiments, the gene therapy composition according to the invention (e.g., a polynucleotide on a viral vector) is administered intravitreally or intraocularly. In one preferred embodiment, the gene therapy is for intravitreal administration. It will be appreciated that the preferred route will depend on the general condition and age of the subject to be treated, the nature of the condition to be treated and the active ingredient chosen.

In one aspect, the present invention provides a gene therapy to deliver a gene to an eye to increase the expression of Nmnat.

In certain embodiments, the gene that increases protein expression of Nmnat includes Nmnat-1, Nmnat-2, or Nmnat-3. In certain embodiments, the gene is Nmnat-1 (e.g., human NMNAT1).

NMNAT

Nicotinamide nucleotide adenylyltransferase 1 (Nmnat1 [mouse], NMNAT1 [human]) encodes an enzyme which catalyzes a key step in the biosynthesis of nicotinamide adenine dinucleotide (NAD). The encoded enzyme is one of several nicotinamide nucleotide adenylyltransferases, and is specifically localized to the cell nucleus. Alternative splicing of this gene results in multiple (at least three) transcript variants.

The NCBI reference sequences (RefSeq) for human NMNAT1 isoform (1) includes: NM_022787.3 (nucleotide) and NP_073624.2 (protein), the nucleotide sequence of which is known as transcription variant (1) that encodes the longer NMNAT1 isoform (I); and NM_001297778.1 (nucleotide) and NP_001284707.1 (protein), the nucleotide sequence of which is known as transcript variant (2) that differs in the 5' UTR region when compared to variant 1. Variants 1 and 2 encode the same isoform (1), and can all be used in the methods of the invention. All sequences are incorporated by reference.

The related nicotinamide nucleotide adenylyltransferase 2 (nmnat2), unlike the other human family members localized to the nucleus and ubiquitously expressed, this enzyme is cytoplasmic, and is predominantly expressed in the brain. Alternative splicing of this gene results in two transcript variants.

The NCBI reference sequences (RefSeq) for human NMNAT2 isoform (1) includes: NM_015039.3 (nucleotide) and NP_055854.1 (protein), the nucleotide sequence of which may be used in the method of the invention. All sequences are incorporated by reference.

The related nicotinamide nucleotide adenylyltransferase 3 (nmnat3) encodes a protein localized to mitochondria, and may also play a neuroprotective role as a molecular chaperone. Alternatively spliced transcript variants (at least 6) encoding multiple isoforms (at least 5) have been observed for this gene.

The NCBI reference sequences (RefSeq) for human NMNAT3 isoform (3) includes: NM_001320510.1 (nucleotide) and NP_001307439.1 (protein), the nucleotide sequence of which is transcription variant 3 that encodes the longest isoform (3), and may be used in the method of the invention. All sequences are incorporated by reference.

NMNAT2 is emerging as an important NAD producing enzyme in axons and protects from axon degeneration. Ongoing stress negatively impacts Nmnat2 expression in RGCs (q<0.05 in D2 glaucoma Group 4, the final stage detected before glaucomatous degeneration). This decline may be important in the transition to axon degeneration in glaucoma. NMNAT2 expression is decreased in brains with Alzheimer's disease and has a highly variable depression in aged postmortem human brains, which may contribute to the variable vulnerability to these conditions.

Numerous related nmnat sequences in different species of animals (such as house mouse Mus musculus) are readily available from public databases, such as NCBI RefSeq, GenBank, etc. All sequences are incorporated herein by reference.

It is believed that gene therapy employing NAMPT will lead to axon cell toxicity, albeit elevating the $NAD^+$ levels in the cells. NAMPT functions to convert NAM to NMN, which is then converted to $NAD^+$. Intracellular $NAD^+$ is a key molecule associated with axon degeneration. When NAD levels are low, axons rapidly degenerate. It is also established that following axonal injury in sciatic nerve axons, NMN accumulates rapidly. In this model axon degeneration, NMN levels rise within 12 hrs, followed by neural injury occurs at 36-hr following injury. Blocking the NMN producing enzyme NAMPT using FK866 potentially inhibits this axon degeneration, hinting that NMN is toxic to neurons. Axon degeneration appears to be NMN-dependent, and inhibiting the increase of NMN using FK866 protects against axon degeneration. In a zebrafish model of axon degeneration (two-photon-laser axotomy), FK866 potently delayed axon degeneration. In a cell culture model of neurite degeneration (superia cervical ganglion; SCG), rapidly clearing NMN (by overexpression of the bacterial enzyme NMN deamidase which converts NMN to NAMN) robustly protects from axon degeneration.

Accordingly, the present invention represents an unexpected finding that gene therapy employing NMNAT, unlike that of NAMPT, is effective in protecting ocular neurodegeneration.

Thus we chose Nmnat1 over Nampt, as Nampt overexpression would drive the production of NMN, which, without proper clearance, is toxic to neurons.

$Wld^S$

Axonal degeneration is a common component of neurodegenerative disease. There are two models that attempt to explain this greater degree of distal axonal degeneration. The first is "dying back" in which degeneration spreads retrogradely from the nerve terminals. The second is Wallerian degeneration, where degeneration spreads from the site of a lesion in either direction according to the lesion type, ultimately resulting in loss of the axon distal to the lesion site, and leaving the proximal portion intact. Although strictly speaking, Wallerian degeneration only occurs in response to physical injury of the axon, similar mechanisms operate in diseases where no such injury has occurred. The latter is referred to as "Wallerian-like" degeneration. Both types of degeneration will hereinafter be jointly referred to as "Wallerian degeneration."

The recently discovered $Wld^S$ mouse has led to progress in the understanding of these two processes. In these animals, Wallerian degeneration occurs at a rate roughly ten times slower than in wild-type animals. Studies have shown that this mutation also delays pathologies believed to involve "dying back" of axonal terminals. The $Wld^S$ gene therefore provides a mechanistic link between the two models of axonal degeneration.

Despite the identification and characterization of the $Wld^S$ gene, progress towards understanding of the molecular trigger for Wallerian degeneration has been limited. Knowledge of this trigger could have a profound impact on the understanding of the early stages of "dying-back" neurodegenerative diseases.

Mice with the $Wld^S$ gene have delayed Wallerian degeneration. The $Wld^S$ mutation is an autosomal-dominant mutation occurring in the mouse chromosome 4. The gene mutation is a naturally occurring 85-kb tandem triplication, resulting in a mutated region containing two associated genes: nicotinamide mononucleotide adenylyl transferase 1 (Nmnat-1) and ubiquitination factor e4b (Ube4b), and a linker region encoding 18 amino acids. The protein created localizes within the nucleus and is undetectable in axons.

The mutation appears to cause no harm to the mouse. The only known effect is that the Wallerian degeneration is delayed by up to three weeks on average after injury of a nerve. Recent studies suggest that the mutation protects axons by a poorly understood mechanism. While not wishing to be bound by any particular theory, it is likely that the $Wld^S$ mutation leads to overexpression and/or improved localization of the Nmnat (e.g., Nmnat-1) protein and increased NAD synthesis.

In certain embodiments, the method comprises administering a polynucleotide encoding Nmnat (e.g.,Nmnat-1, -2, or -3) or $Wld^S$ to the subject.

In certain embodiments, the polynucleotide encodes $Wld^s$ or a human sequence equivalent thereof.

In certain embodiments, the method comprises administering NAM or a precursor, and a polynucleotide encoding Wld$^S$ to the subject.

In certain embodiments, the polynucleotide is administered to the subject locally. For example, to treat glaucoma, the agent may be locally delivered to the affected eye(s), Vectors In certain embodiments, the polynucleotide is administered to the subject on a viral vector. Exemplary suitable viral vector includes, but not limited to, an AAV vector, an adenoviral vector, a Lentiviral vector, a retroviral vector, and the like. Preferably, the viral vector is a AAV vector or a Lentiviral vector.

For instance, the polynucleotide may be introduced into the subject as exogenous genetic materials that may modulate the expression of one or more target genes of interest. Such kind of gene therapy can be used, for example, in a method directed at repairing damaged or diseased tissue, such as neuronal tissue. In brief, any suitable vectors, including an adenoviral, a lentiviral, or retroviral gene delivery vehicle (see below), may be used to deliver genetic information, like DNA and/or RNA to the subject. A skilled person can replace or repair particular genes targeted in gene therapy. For example, a normal gene may be inserted into a nonspecific location within the genome of a diseased cell to replace a nonfunctional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off of a particular gene. In certain embodiments, the target cells (such as neuronal stem cells) are ex vivo treated by a gene therapy approach and are subsequently transferred to the mammal, preferably a human being in need of treatment.

Any art recognized methods for genetic manipulation may be used, including transfection and infection (e.g., by a viral vector) by various types of nucleic acid constructs.

For example, heterologous nucleic acids (e.g., DNA) can be introduced into the subject by way of physical treatment (e.g., electroporation, sonoporation, optical transfection, protoplast fusion, impalefection, hydrodynamic delivery, nanoparticles, magnetofection), using chemical materials or biological vectors (viruses). Chemical-based transfection can be based on calcium phosphate, cyclodextrin, polymers (e.g., cationic polymers such as DEAE-dextran or polyethylenimine), highly branched organic compounds such as dendrimers, liposomes (such as cationic liposomes, lipofection such as lipofection using Lipofectamine, etc.), or nanoparticles (with or without chemical or viral functionalization).

A nucleic acid construct comprises a nucleic acid molecule of interest, and is generally capable of directing the expression of the nucleic acid molecule of interest in the cells into which it has been introduced.

In certain embodiments, the nucleic acid construct is an expression vector wherein a nucleic acid molecule encoding a gene product, such as a polypeptide or a nucleic acid that antagonizes the expression of a polypeptide (e.g., an siRNA, miRNA, shRNA, antisense sequence, aptamer, ribozyme, antagomir, RNA sponge, etc.) is operably linked to a promoter capable of directing expression of the nucleic acid molecule in the target cells.

A DNA construct prepared for introduction into a particular cell typically includes a replication system recognized by the cell, an intended DNA segment encoding a desired polypeptide, and transcriptional and translational initiation and termination regulatory sequences operably linked to the polypeptide-encoding segment. A DNA segment is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a pre-protein that participates in the secretion of a polypeptide. Generally, a DNA sequence that is operably linked are contiguous, and, in the case of a signal sequence, both contiguous and in reading phase. However, enhancers need not be contiguous with a coding sequence whose transcription they control. Linking is accomplished by ligation at convenient restriction sites or at adapters or linkers inserted in lieu thereof.

The selection of an appropriate promoter sequence generally depends upon the host cell selected for the expression of a DNA segment. Examples of suitable promoter sequences include eukaryotic promoters well known in the art (see, e.g., Sambrook and Russell, *Molecular Cloning: A Laboratory Manual*, Third Edition, 2001). A transcriptional regulatory sequence typically includes a heterologous enhancer or promoter that is recognized by the cell. Suitable promoters include the CMV promoter. An expression vector includes the replication system and transcriptional and translational regulatory sequences together with the insertion site for the polypeptide encoding segment can be employed. Examples of workable combinations of cell lines and expression vectors are described in Sambrook and Russell (2001, supra) and in Metzger et al. (1988) *Nature*, 334: 31-36.

Some aspects of the invention concern the use of a nucleic acid construct or expression vector comprising a nucleotide sequence as defined above, wherein the vector is a vector that is suitable for gene therapy. Vectors that are suitable for gene therapy are known in the art, such as those described in Anderson (*Nature*, 392: 25-30, 1998); Walther and Stein (*Drugs*, 60: 249-71, 2000); Kay et al. (*Nat. Med.*, 7: 33-40, 2001); Russell (*J. Gen. Virol.*, 81:2573-604, 2000); Amado and Chen (*Science* 285:674-6, 1999); Federico (*Curr. Opin. Biotechnol.*, 10:448-53, 1999); Vigna and Naldini (*J. Gene Med.*, 2:308-16, 2000); Marin et al. (*Mol. Med Today*, 3:396-403, 1997); Peng and Russell (*Curr. Opin. Biotechnol.*, 10:454-7, 1999); Sommerfelt (*J. Gen. Virol.*, 80:3049-64, 1999); Reiser (*Gene Ther.*, 7: 910-3, 2000); and references cited therein (all incorporated by reference). Examples include integrative and non-integrative vectors such as those based on retroviruses, adenoviruses (AdV), adeno-associated viruses (AAV), lentiviruses, pox viruses, alphaviruses, and herpes viruses.

A particularly suitable gene therapy vector includes an Adenoviral (Ad) and Adeno-associated virus (AAV) vector, These vectors infect a wide number of dividing and non-dividing cell types. In addition, adenoviral vectors are capable of high levels of transgene expression. However, because of the episomal nature of the adenoviral and AAV vectors after cell entry, these viral vectors are most suited for therapeutic applications requiring only transient expression of the transgene (Russell, *J. Gen. Virol.*, 81:2573-2604, 2000; Goncalves, *Virol* 2(1):43, 2005) as indicated above. Preferred adenoviral vectors are modified to reduce the host response as reviewed by Russell (2000, supra). Safety and efficacy of AAV gene transfer has been extensively studied in humans with encouraging results in the liver, muscle, CNS, and retina (Manno et al., *Nat. Medicine*, 2006; Stroes et al., *ATVB*, 2008; Kaplitt, Feigin, *Lancet*, 2009; Maguire, Simonelli et al. *NEJM*, 2008; Bainbridge et al., *NEJM*, 2008).

AAV2 is the best characterized serotype for gene transfer studies both in humans and experimental models. AAV2 presents natural tropism towards skeletal muscles, neurons, vascular smooth muscle cells and hepatocytes. Other examples of adeno-associated virus-based non-integrative vectors include AAV1, AAV3, AAV4, AAV5, AAV6, AAV7, AAV8, AAV9, AAV10, AAV11 and pseudotyped AAV. The use of non-human serotypes, like AAV8 and AAV9, might be useful to overcome these immunological responses in subjects, and clinical trials have just commenced (ClinicalTrials dot gov Identifier: NCT00979238). For gene transfer into a liver cell, an adenovirus serotype 5 or an AAV serotype 2, 7 or 8 have been shown to be effective vectors and therefore a preferred Ad or AAV serotype (Gao, *Molecular Therapy*, 13:77-87, 2006).

An exemplary retroviral vector for application in the present invention is a lentiviral based expression construct. Lentiviral vectors have the unique ability to infect non-dividing cells (Amado and Chen, *Science* 285:674-676, 1999). Methods for the construction and use of lentiviral based expression constructs are described in U.S. Pat. Nos. 6,165,782, 6,207,455, 6,218,181, 6,277,633, and 6,323,031, and in Federico (*Curr. Opin. Biotechnol.* 10:448-53, 1999) and Vigna et at (*J. Gene Med.* 2:308-16, 2000).

Generally, gene therapy vectors will be as the expression vectors described above in the sense that they comprise a nucleotide sequence encoding a gene product (e.g., a polypeptide) of the invention to be expressed, whereby a nucleotide sequence is operably linked to the appropriate regulatory sequences as indicated above. Such regulatory sequence will at least comprise a promoter sequence. Suitable promoters for expression of a nucleotide sequence encoding a polypeptide from gene therapy vectors include, e.g., cytomegalovirus (CMV) intermediate early promoter, viral long terminal repeat promoters (LTRs), such as those from murine Moloney leukaemia virus (MMLV) roes sarcoma virus, or HTLV-1, the simian virus 40 (SV 40) early promoter and the herpes simplex virus thymidine kinase promoter. Additional suitable promoters are described below.

Several inducible promoter systems have been described that may be induced by the administration of small organic or inorganic compounds. Such inducible promoters include those controlled by heavy metals, such as the metallothionine promoter (Brinster et al., *Nature*, 296:39-42, 1982; Mayo et al., *Cell*, 29:99-108, 1982), RU-486 (a progesterone antagonist) (Wang et al., *Proc. Natl. Acad Sci. USA*, 91:8180-8184, 1994), steroids (Mader and White, *Proc. Natl. Acad. Sci. USA*, 90:5603-5607, 1993), tetracycline (Gossen and Bujard, *Proc. Natl. Acad. Sci. USA*, 89:5547-5551, 1992; U.S. Pat. No. 5,464,758; Furth et al., *Proc. Natl. Acad. Sci. USA*, 91:9302-9306, 1994; Howe et al., *J. Biol. Chem.*, 270:14168-14174, 1995; Resnitzky et al., *Mol. Cell. Biol.*, 14:1669-1679, 1994; Shocked et al., *Proc. Natl. Acad. Sci. USA*, 92:6522-6526, 1995) and the tTAER system that is based on the multi-chimeric transactivator composed of a tetR polypeptide, as activation domain of VP 16, and a ligand binding domain of an estrogen receptor (Yee et al., 2002, U.S. Pat. No. 6,432,705).

Suitable promoters for nucleotide sequences encoding small RNAs for knock down of specific genes by RNA interference (see below) include, in addition to the above mentioned polymerase II promoters, polymerase III promoters. The RNA polymerase III (pol III) is responsible for the synthesis of a large variety of small nuclear and cytoplasmic non-coding RNAs including 5S, U6, adenovirus VA1, Vault, telomerase RNA, and tRNAs. The promoter structures of a large number of genes encoding these RNAs have been determined and it has been found that RNA pol III promoters fall into three types of structures (for a review see Geiduschek and Tocchini-Valentini, *Annu. Rev. Biochem.*, 57: 873-914, 1988; Willis, *Eur. J. Biochem.*, 212:1-11, 1993; Hernandez, *J. Biol. Chem.*, 276:26733-36, 2001). Particularly suitable for expression of siRNAs are the type 3 of the RNA pol III promoters, whereby transcription is driven by cis-acting elements found only in the 5'-flanking region, i.e., upstream of the transcription start site. Upstream sequence elements include a traditional TATA box (Mattaj el al., *Cell*, 55:435-442, 1988), proximal sequence element and a distal sequence element (DSE; Gupta and Reddy, *Nucleic Acids Res.*, 19:2073-2075, 1991). Examples of genes under the control of the type 3 pol III promoter are U6 small nuclear RNA (U6 snRNA), 7SK, Y, MRP, HI and telomerase RNA genes (see, e.g., Myslinski et al., *Nucl. Acids Res.*, 21:2502-09, 2001).

A gene therapy vector may optionally comprise a second or one or more further nucleotide sequence coding for a second or further polypeptide. A second or further polypeptide may be a (selectable) marker polypeptide that allows for the identification, selection and/or screening for cells containing the expression construct. Suitable marker proteins for this purpose are, e.g., the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russell, *Molecular Cloning: A Laboratory Manual*, Third Edition, Cold Spring Harbor Laboratory, Cold Spring Harbor Laboratory Press, New York, 2001.

Alternatively, a second or further nucleotide sequence may encode a polypeptide that provides for fail-safe mechanism that allows a subject from the transgenic cells to be cured, if deemed necessary. Such a nucleotide sequence, often referred to as a suicide gene, encodes a polypeptide that is capable of converting a prodrug into a toxic substance that is capable of killing the transgenic cells in which the polypeptide is expressed. Suitable examples of such suicide genes include, e.g., the *E. coil* cytosine deaminase gene or one of the thymidine kinase genes from Herpes Simplex Virus, Cytomegalovirus and Varicella-Zoster virus, in which case ganciclovir may be used as prodrug to kill the IL-10 transgenic cells in the subject (see, e.g., Clair et al., *Antimicrob. Agents Chemother.*, 31:844-849, 1987).

Administration Routes for Gene Therapy in the Eye

In one aspect, the present invention provides a method of gene therapy to treat ocular degeneration diseases. One skilled in the art would recognize the routes for gene therapy in the eye that involves intravitreal administration or intraocular administration.

Intraocular administration is delivering a gene composition anywhere into eyeball.

In a preferred embodiment, the gene composition is injected intravitreally. Intravitreal administration is delivering a gene composition directly into the vitreous compartment of the eye, i.e., the fluid that makes up the posterior part of the eye, directly adjacent to the retina. In certain embodiments, vitreous is removed to make space for drug during injection.

Intravitreal injections typically take place in the doctor's office, but can also take place in the Operation Rooms in a hospital. Patients generally undergo topical anesthesia (usually eye-drops or soaked-sponge/cotton swabs), with commonplace drugs such as proparacaine, lidocaine, and the like.

In certain embodiments, the gene composition is injected subretinally (i.e., under the retina).

For injection, needle size of 27-32 gauge may be used. In a preferred embodiment, the needle size is 30-gauge. Needle injection is becoming a popular technique to inject agents into the eye and does not pose any risks. Injection can be deep or superficial. Injections may he straight (i.e. at 90 degrees to the surface of the eye), oblique (45-60 degrees), or double-pane (in oblique, out straight).

Gene Therapy in the Eye

The present invention provides a gene therapy using a gene composition to elevate NAD$^+$ in the RGCs. The eye is an ideal organ to utilize gene therapy, because it is small in size (i.e. less cells to transfect), easily accessible, partially/mostly immune privileged (i.e. small/little chance of eliciting an immune response), and the fellow eye serves as a contra-lateral control and a backup.

Several eye-based gene therapy clinical trials have been underway for blinding disorders, For example, gene therapy of RPE65 gene via AAV2 vector to treat Leber's Congenital Amaurosis is in Phase III clinical trial (NCT00481546, NCT00516477, NCT00643747 and NCT00999609); gene therapy of MERTK gene using AAV2 vector to treat Retinitis Pigmentosa is in Phase I (NCT014822195); gene therapy of ABCA4 gene using EIAV lentivirus vector to treat Stargardt's is presently in Phase II (NCT01367444); gene therapy of gene REP-1 gene using AAV2 vector to treat Chorioderemia is presently in Phase II (NCT02553135). The clinical studies in several clinics demonstrate that gene delivery to eye appears to be safely tolerated.

Combined Therapy—An Additional Therapeutic Agent

In certain embodiments, the present invention provides a method of combined therapy treatment of neurodegeneration by administering to a human in need thereof a compound that enhances the intracellular level of NAD$^+$ in a nerve cell (e.g., RGC) and an additional therapeutic agent.

In certain embodiments, the additional therapeutic agent of the invention for treating glaucoma includes, but not limited to an agent that lowers IOP. Exemplary additional therapeutic agent includes, but not limited to a beta blocker (such as Timolol maleate, Timolol hemihydrate, Levobunolol HCL, Metipranolol Carteolol, Betaxolol and the like), a non-selective adrenergic agonist (such as Epinepherine, Dipivefrin HCL), a selective α-2 adrenergic agonists (such as Apraclonidine HCL, Brimonidine tartrate, and Brimonidine tartrate in Purite), or a Carbonic Anhydrase Inhibitor (CAI, such as acetazolamide (oral), acetazolamide (parenteral), methazolamide (oral), dorzolamide (topical), and brinzolamide (topical)).

In certain embodiments, the additional therapeutic agent includes a prostaglandin analog (such as Latanoprost, Travaprost, and Bimataprost (prostamide)), parasympathomimetic agonist (including direct cholinergic agonist such as pilocarpine HCL; and indirect cholinergic agents such as echothiophate iodide, demercarium iodide, and physostigmine isofluorophate), and carbachol (a mixed direct agonist/acetylcholine releasing agent).

In certain embodiment, the additional therapeutic agent comprises a fixed-combination medication that offers the potential advantage of increased convenience, compliance, efficacy, and cost. The fixed-combination may comprise a topical beta-blocker combined with a prostaglandin analogue, an alpha-adrenoceptor agonist, or a topical carbonic anhydrase inhibitor. Exemplary fixed combination include: (1) dorzolamide and timolol, such as Dorzolamide hydrochloride 2% and timolol maleate ophthalmic solution 0.5% (e.g., Cosopt, now available as generic), (2) brimonidine with timolol or brinzolamide, such as brimonidine tartrate 0.2%, timolol maleate ophthalmic solution 0.5% (e.g., Combigan) and brimonidine tartrat 0.2% and brinzolamide 1% (e.g., Simbrinza), or (3) latanoprost and timolol.

In certain embodiment, the additional therapeutic agent comprises a hyperosmotic agent such as oral glycerine, oral isosorbide, and intravenous mannitol that can rapidly lower IOP by decreasing vitreous volume. They do not cross the blood-ocular barrier and therefore exert oncotic pressure that dehydrates the vitreous. The hyperosmotic agent is typically used in acute situations to temporarily reduce high IOP until more definitive treatments can be rendered.

The invention is illustrated by the following non-limiting examples.

EXAMPLES

Example 1 Identification of Glaucoma Susceptible Genes/Pathways (A) Selection of Mouse Model Mimicking Neurodegeneration in Humans We chose the DBA/2J D2 (D2) mouse model to examine the pathogenesis of neurodegeneration in humans. The D2 mouse is a widely used model of glaucoma, which recapitulates the hallmark features of human glaucoma. In D2 mice mutant alleles of two genes (Gpnmb$^{R250X}$, Tyrp1$^b$) cause a progressive iris disease. This iris disease has two main components: and iris stromal atrophy (highly resembles essential iris atrophy in humans) and iris pigment dispersion phenotypes (highly resemble pigment dispersion syndrome in humans). Both essential iris atrophy and pigment dispersion syndrome induce IOP) elevation and glaucoma in humans. Iris disease in D2 eyes results in age-related elevated intraocular pressure (IOP) in the majority of eyes by 8-9 months of age. Optic nerve degeneration is almost complete by 12 months of age (typically >70% nerves have severe damage).

In this study, the D2 mice were verified that they undergo ocular neurodegeneration following age-related IOP increases. Specifically, we used D2 mice at 3 ages; namely, 4-, 9-, and 12-months of age.
- (i) 4-month old D2 mice were verified to exhibit normal intraocular pressure (IOP) (i.e., 10-13 mmHg) and no glaucoma (i.e., these mice were at an age preceding the development of IOP and pre-glaucoma; no detectable neurodegeneration). At this age, D2 mice are indistinguishable from control mice.
- (ii) 9-month old D2 mice were verified to exhibit high IOP (i.e., >21 mmHg) but no neurodegeneration. Although conventional glaucoma is absent at this developmental stage (i.e., pre-neurodegeneration), eyes in the 9-month old D2 mice undergo molecular changes defined as having "early glaucoma" herein.
- (iii) 12-month old D2 mice were verified to exhibit variable high IOP (i.e., 14 to >21 mmHg) and neurodegeneration becomes apparent (i.e., glaucoma; >60% eyes have severe neurodegeneration).
- (iv) Control 02-Gpnmb$^+$ mice were used in this study, because these mice exhibit neither high IOP nor neurodegeneration with aging. These mice are identical to D2 mice except for a correction of the iris disease causing Gpnmb$^{R250X}$ mutation.

(B) Isolation of Retinal Ganglion Cells (RGC) from Retinas of D2 Mice

We harvested retina from eyes obtained from (i) 4-month old DBA/2J D2 mice. (ii) 9-month old DBA/2J D2 mice, and (iii) age-, sex-, and strain-matched 02-Gpnmb$^+$ wildtype controls.

Retinal samples were first stained with an antibody cocktail. Retinal ganglion cells (RGCs) were identified as Thy1.2$^+$ cells (and negative for Cd11b$^-$, Cd11c$^-$, Cd31$^-$, Cd34$^-$, Cd45.2$^-$, GFAP$^-$, DAPI$^-$). FACS positive RCGs were plated and stained with SNAP-25 and β-tubulin (specific markers of RGCs) to confirm the RGC status.

Using fluorescence-activated cell sorting (FAC sorting), we then isolated RGCs from the freshly harvested retinas in these three groups of mice. See FIGS. 27A-27E.

(C) RNA Sequencing

To identify susceptible genes/pathways leading; to glaucoma, we performed RNA-sequencing (RNA-se) from RNA of RGCs obtained above in (B) to elucidate very early molecular changes within the RGCs that precede neurodegeneration. Amplified dscDNA libraries (double-stranded copy DNA) generated from RNA and read at a depth of 35 million reads per sample. Data analysis was performed at a false discovery rate (FDR, q) of q<0.05. Samples from all groups (B) were successfully amplified and sequenced.

We performed additional metabolic profiling of neural retinas from 4-, 9-, and 12-months old D2 and D2-Gpnmb$^+$ eyes. Metabolic profiling was performed using targeted assays following the manufacturers recommendations. The following metabolites were profiled: NAD+/NADH (i.e. total NAD, NAD(t)), GSH/GSSG (i.e. total glutathione, glutathione(t)), and pyruvate.

(D) Hierarchical Clustering (HC)

In this study, we sequenced the RNA from the isolated RGCs at a depth of 35 million reads per sample. Unsupervised hierarchical clustering (MC) was used to define molecularly determined stages of glaucoma among samples that are at initial stages of disease and morphologically indistinguishable from age-matched D2-Gpnmb$^+$ or young controls.

Figure 2A:
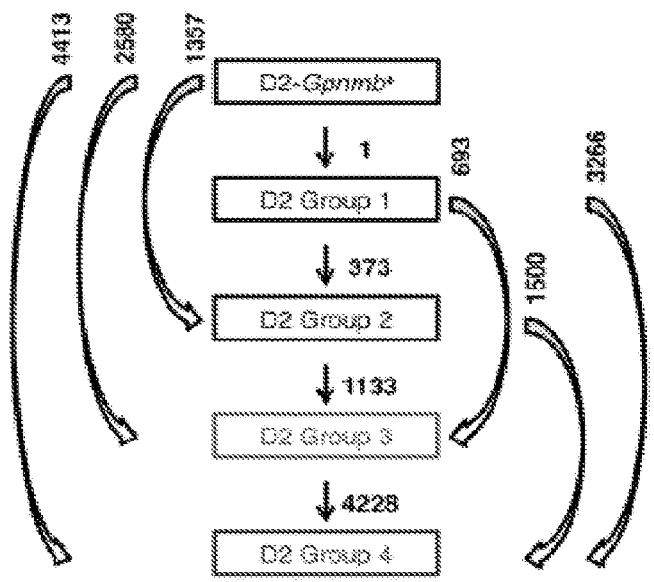
FIG. 2A shows the number of differentially expressed (DE) genes among the 4 D2 mice groups (Group 1, Group 2, Group 3, and Group 4) and the D2-Gpnmb$^+$ control group.
Figure 2B:
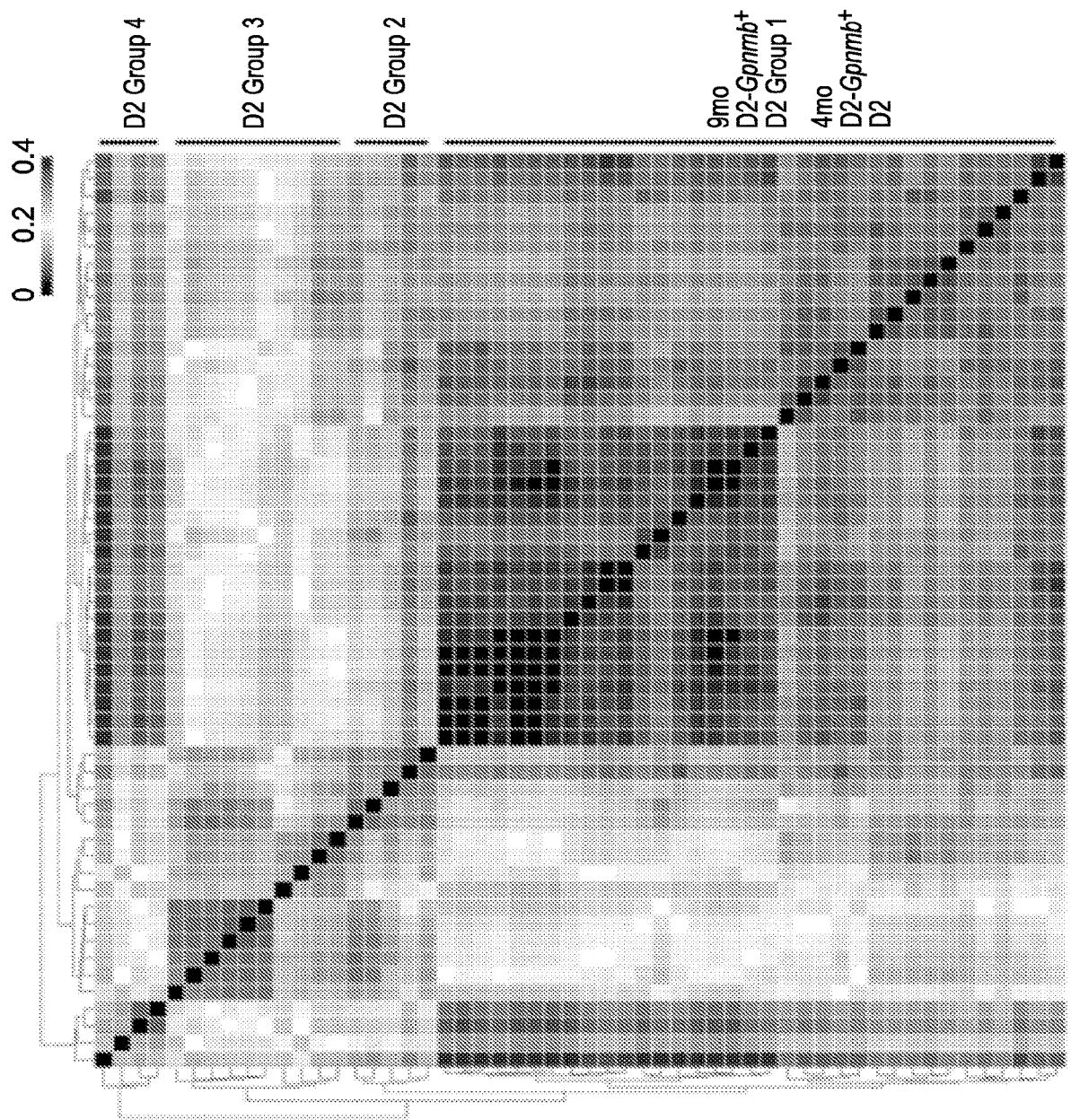
FIG. 2B shows heatmap correlations of all samples (Spearman's rho, blue=highest correlation, red=lowest correlation). Dendrogram from FIG. 1 is shown in grey.

HC identified 4 distinct groups of 9-month old D2 samples (i.e., Group 1, Group 2, Group 3 and Group 4). Group 1 clustered with all of the control samples and represents D2 RGCs with no detectable glaucoma at a molecular level. All samples in Groups 2 to 4 were at early stages of disease, increasing group number were observed reflecting an increasing distance from controls (greater disease progression at a transcriptomic level) (FIGS. 1, 2A, and 2B).

Figure 3A:
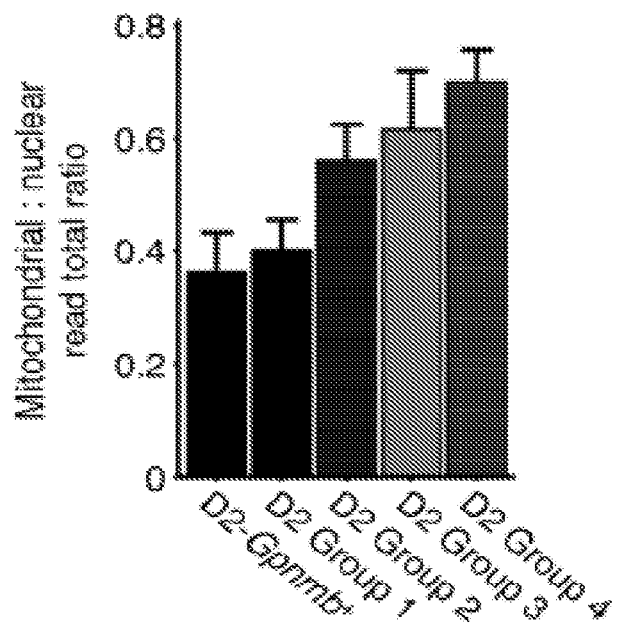
FIG. 3A shows that the mitochondrial:nuclear read total ratio increases with increasing HC distance from controls (9-month old mice). The result is consistent with the notion that mitochondrial dysfunction is an early driver of RGC damage in glaucoma.

As disease progressed, there was an increase in transcript abundance that was most pronounced for mitochondrial reads (FIG. 3A). Imbalances in the relative proportions of mitochondrial molecules encoded by nuclear and mitochondrial genomes negatively impact mitochondrial function. In D2 Groups 2 to 4, differential expression of genes encoding mitochondrial proteins, and significant enrichment of differentially expressed genes (compared to age- and sex-matched D2-Gpnmb$^+$ control RGCS) in the mitochondrial dysfunction and oxidative phosphorylation pathways further point to mitochondrial abnormalities within RGCs (FIGS. 3A-3J, and 3K, and Tables 1-3 below).

Total read abundance across the transcriptome (i.e. all transcribed genes) was split into those reads derived from the nuclear transcriptome (i.e. encoded in the nucleus) or the mitochondrial transcriptome (i.e. encoded at the mitochondrion). Read abundance increased in both transcriptomes in D2 RGCs but was most abundant in the mitochondria-derived reads, indicating an imbalance that would favor mitochondrial dysfunction (FIG. 3A).

Figure 3B:
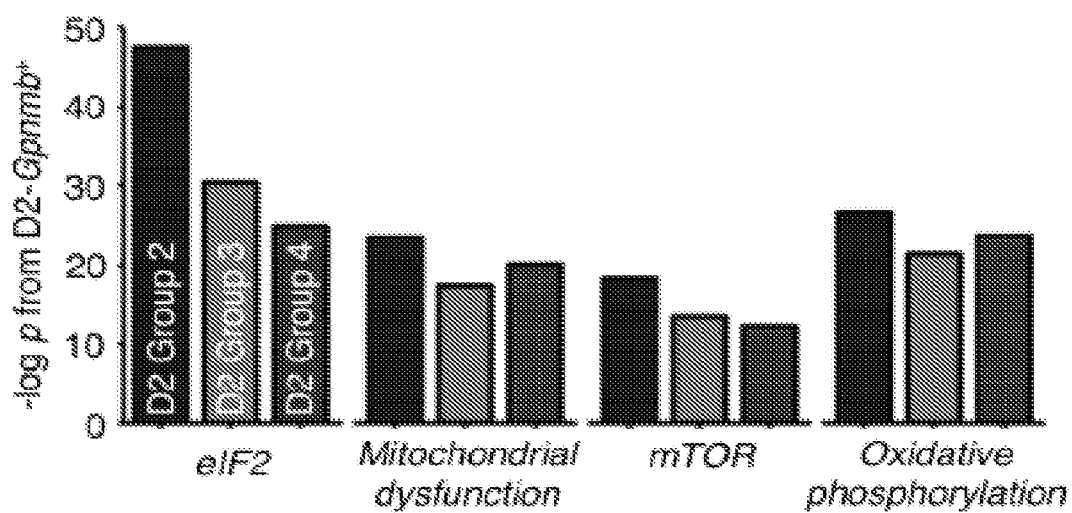
FIG. 3B shows several top significantly enriched pathways based on Ingenuity Pathway Analysis (IPA), using RNA-seq data obtained from RGCs of pre-disease D2 mice (three clusters of 9-month old D2 mice—Group 2, Group 3, and Group 4) and age- and sex-matched wild-type controls (D2-Gpnmb$^+$). The larger the -log p value the greater the enrichment. Two of the top 3 enriched pathways are mitochondrial dysfunction and oxidative phosphorylation. See also Table 3 for additional significantly enriched pathways. Note that there are no differentially expressed pathways in D2 Group 1.

Top enriched pathways (IPA) that appear in D2 Groups 2, 3, and 4. There are no enriched pathways in D2 Group 1 as there is only 1 differentially expressed (DE) gene. This D2 Group 1 represents eyes that have not undergone glaucomatous insults (FIG. 3B).

Figure 3C:
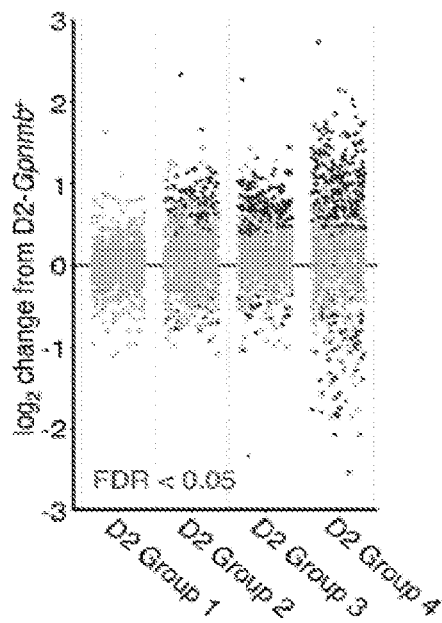
FIG. 3C shows that transcript expression primarily increases for nuclear encoded mitochondrial proteins with increasing HC distance of the D2 groups from controls (all 9-month old mice). The result is again consistent with the notion that mitochondrial dysfunction is an early driver of RGC damage in glaucoma. Dots represent individual genes, grey or lighter dots=not differentially expressed, red or darker dots=differentially expressed at q<0.05, Genes were taken from mouse MitoCarta2.0 (Calvo et al., *Nucleic Acids Res* 44, D1251-1257, 2016).

We prepared a plot of all mitochondrial proteins encoded by nuclear (and not mitochondrial) genes. DE genes are shown in red. Non-DE genes are shown in grey. The increasing abundance of nuclear derived transcripts encoding mitochondrial proteins further indicates an imbalance in mitochondrial turnover or function (FIG. 3C).

Figure 3D:
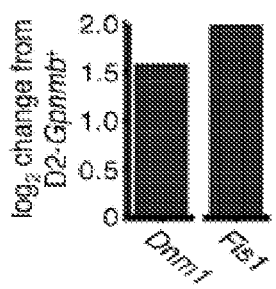
FIG. 3D shows that RNA-sequencing identifies increased mitochondrial fission gene transcripts early in glaucoma (9-month old mice). The result is consistent with the notion that mitochondrial dysfunction is an early driver of RGC damage in glaucoma.

An increase in expression of mitochondrial fission genes (Dnm1 and Fis1) indicates a pro-fission event in mitochondria early in glaucoma. Increase fission is associated with increased mitochondrial turnover and disease. Mutations that affect mitochondrial fusion/fission dynamics typically are lethal or cause neurological conditions (including, but not limited to, dominant optic atrophy, Charcot-Marie-Tooth disease) (FIG. 3D).

Figure 3E:
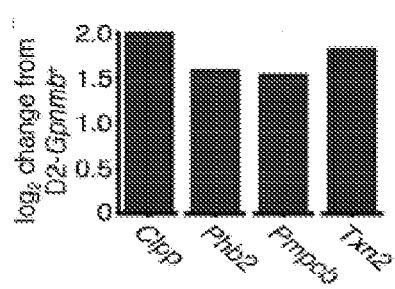
FIG. 3E shows an early mitochondrial unfolded protein response compared to controls. Data shown is for D2 Group 4 (9-month old mice). The result is consistent with the notion that mitochondrial dysfunction is an early driver of RGC damage in glaucoma.

There was an increased in expression of genes involved in the mitochondrial unfolded protein response. This is a stress response within cells that typically often precedes apoptosis (programmed cell death) (FIG. 3E).

Individual plots of genes in mitochondria-relevant pathways was prepared. DE genes are shown in red, non-DE genes are shown in grey. Note the upregulation of mitochondrial genes across the pathways, especially in oxidative phosphorylation and reactive oxygen species metabolism, which points to an energy crisis within the cell (FIG. 3F).

Figure 3G:
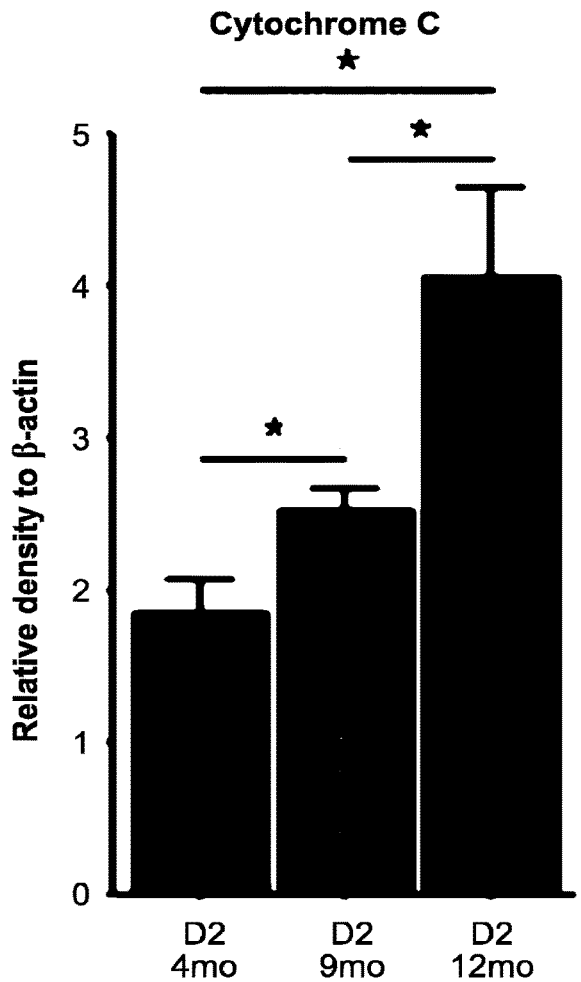
FIGS. 3G and 3H are bar graphs summarizing data from Western blot protein validation (FIGS. 3I and 3J, respectively) of differentially expressed genes (n=4/age group). There were general protein increases in both cytochrome c (FIG. 3G) and eIF2α (FIG. 3H) that correlated with transcript abundances as assessed by RNA-sequencing. The vertical axis in both bar graphs is relative density to β-actin. *=P<0.05, **=P<0.01.
Figure 3H:
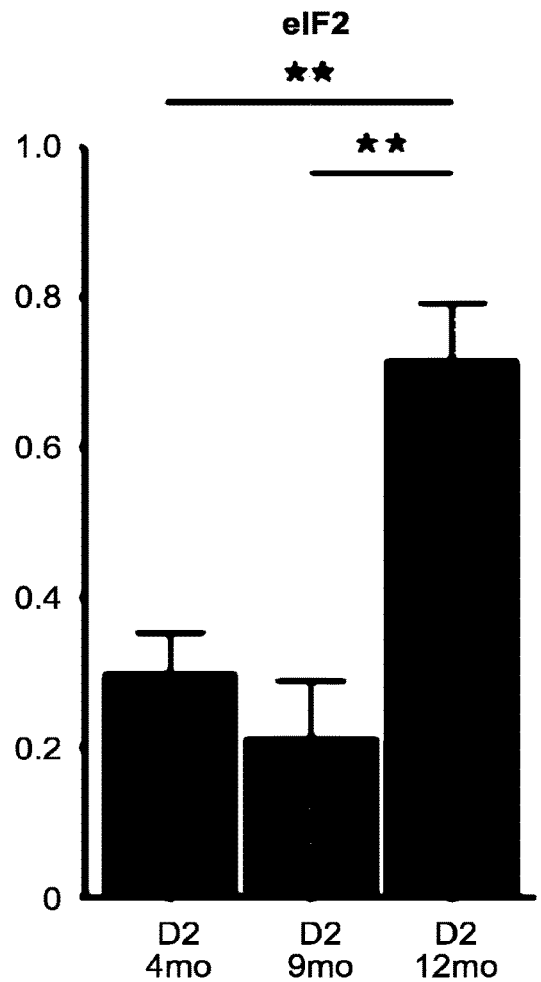
Figure 3I:
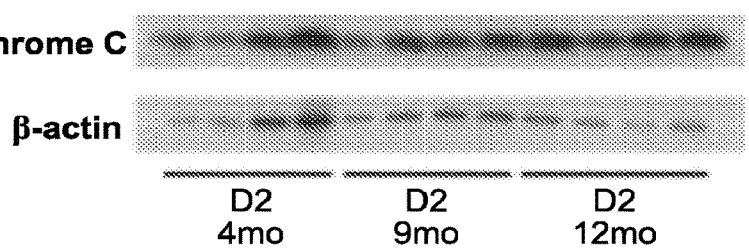
FIG. 3F represents results of individual gene expression plots showing metabolic and oxidative events in early glaucoma (9-month old mice). Dots represent individual genes, grey or lighter dots=not differentially expressed, red or darker dots=differentially expressed at q<0.05. Again, oxidative phosphorylation genes are among the ones showing the highest levels of differential expression, and differential expression appears to be progressively higher in D2 groups having increasing HC distance from the control (Group 4>Groups 3 and 2).
FIG. 3K shows that oxidative phosphorylation genes are differentially expressed across all groups, with increasingly higher expressions in the D2 groups having increasing HC distance from the control (Group 4>Group 3>Group 2>Group 1), Red=highest expression, blue=lowest expression, I-V=mitochondrial complexes I-V (tabulated in Table 1), G=D2-Gpnmb$^+$, 1-4 D2 Groups 1-4.

The protein analysis (Western blot) of the mitochondrial pro-apoptotic molecule cytochrome C from the retina shows that cytochrome C was upregulated at both the gene and the protein levels during early glaucoma (9 month) and was significantly upregulated by 12 month (FIGS. 3G and 3I).

Figure 3J:
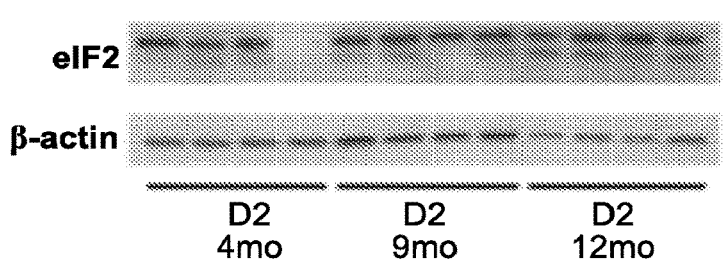
Figure 3K:
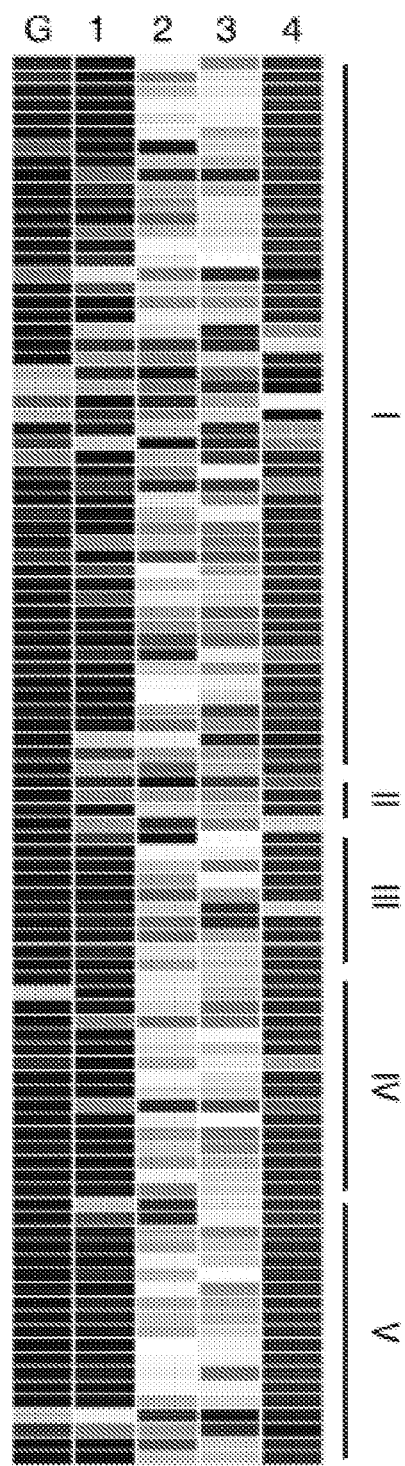

Protein analysis also confirms that there was an eIF2 upregulation within the retina (FIGS. 3H and 3J).

TABLE 1

Mitochondrial complex genes list from FIGS. 1, 3A-3E, 3K 4A, and 4B

| Complex | Gene | Complex | Gene |
|---|---|---|---|
| I | ENSMUSG00000064341 | I | ENSMUSG00000064345 |
| I | ENSMUSG00000064360 | I | ENSMUSG00000064363 |
| I | ENSMUSG00000064367 | I | ENSMUSG00000064368 |
| I | ENSMUSG00000065947 | I | Ndufa1 |
| I | Ndufa10 | I | Ndufa11 |
| I | Ndufa12 | I | Ndufa13 |
| I | Ndufa2 | I | Ndufa3 |
| I | Ndufa4 | I | Ndufa412 |

TABLE 1-continued

Mitochondrial complex genes list from FIGS. 1, 3A-3E, 3K 4A, and 4B

| Complex | Gene | Complex | Gene |
|---|---|---|---|
| I | Ndufa5 | I | Ndufa6 |
| I | Ndufa7 | I | Ndufa8 |
| I | Ndufa9 | I | Ndufab1 |
| I | Ndufaf1 | I | Ndufaf2 |
| I | Ndufaf3 | I | Ndufaf4 |
| I | Ndufaf5 | I | Ndufaf6 |
| I | Ndufaf7 | I | Ndufb10 |
| I | Ndufb11 | I | Ndufb2 |
| I | Ndufb3 | I | Ndufb4 |
| I | Ndufb5 | I | Ndufb6 |
| I | Ndufb7 | I | Ndufb8 |
| I | Ndufb9 | I | Ndufc1 |
| I | Ndufc2 | I | Ndufs1 |
| I | Ndufs2 | I | Ndufs3 |
| I | Ndufs4 | I | Ndufs6 |
| I | Ndufs7 | I | Ndufs8 |
| I | Ndufv1 | I | Ndufv2 |
| I | Ndufv3 | | |
| II | Sdha | II | Sdhb |
| II | Sdhc | II | Sdhd |
| III | Cyc1 | III | ENSMUSG00000064370 |
| III | Uqcr10 | III | Uqcr11 |
| III | Uqcrb | III | Uqcrc1 |
| III | Uqcrc2 | III | Uqcrfs1 |
| III | Uqcrh | III | Uqcrq |
| IV | Cox4i1 | IV | Cox4i2 |
| IV | Cox5a | IV | Cox5b |
| IV | Cox6a1 | IV | Cox6b1 |
| IV | Cox6b2 | IV | Cox6c |
| IV | Cox7a2 | IV | Cox7a21 |
| IV | Cox7b | IV | Cox7c |
| IV | Cox8a | IV | ENSMUSG00000064351 |
| IV | ENSMUSG00000064354 | IV | ENSMUSG00000064358 |
| V | Atp5a1 | V | Atp5b |
| V | Atp5c1 | V | Atp5d |
| V | Atp5e | V | Atp5f1 |
| V | Atp5g1 | V | Atp5g2 |
| V | Atp5g3 | V | Atp5h |
| V | Atp5j | V | Atp5j2 |
| V | Atp5k | V | Atp5l |
| V | Atp5o | V | Atp5s |
| V | Atp5s1 | V | ENSMUSG00000064356 |
| V | ENSMUSG00000064357 | | |

TABLE 2

Genes included in Pathway Terms for FIGS. 1, 3A-3E, 3K, 4A, 4B, 5A, 11-14, 20A, 20B

| Pathway | Gene List |
|---|---|
| Fatty acid metabolism | Abcd2, Pex2, Cyp4f18, Slc27a2, Acot5, Slc27a5, Acox1, Acaa1a, Acot2, Acot4, Slc27a4, Elovl2, Acsbg1, AcotS, Pex5, Hsd17b4, Pla2g4f, Edn1, Edn2, Mif, Ptgis, Cd74, Ptgds, Pnpla8, Ptges2, Tbxas1, Ptges3, Ptges, Ptgs1, Hpgds, Fam213b, Ptgs2, Phyh, Pex13, Hacl1, Hao1, Acsl5, Cpt1a, Slc27a6, Slc27a1, Slc27a3, Acot1, Acsl4, Acsbg2, Acsl6, Acsl1, Acsl3, Acsm5, Fa2h, Ppara, Ghr, Prkar2b, Acaa2, Pla2g15, Agpat6, Acsf2, Snca, Them4, Amacr, Cryl1, Acsf3, Alkbh7, Cyb5a, Stat5b, Lypla1, Acnat2, Acox2, Aacs, Ankrd23, Cpt2, Baat, Abhd5, Cyp4a10, Crot, Acnat1, Angptl3, Mecr, Acsm4, Lypla2, Acot11, C3, Gpam, Sgpl1, Tnxb, Th, Apoa2, Crat, Aasdh, Cyp4a12a, Echdc2, Acsm2, Acaa1b, Stat5a, Crem, Ucp3, Ndufs6, Them5, Acot12, Scd1, Scd4, Ch25h, Lipc, Prkag1, Fads3, Prkag3, Acaca, Brca1, Ndufab1, Mlycd, Mcat, Prkaa2, Hnf1a, Acsm1, Sc5d, H2-Ke6, Agmo, Hsd17b12, Lpl, Mgll, Acsm3, Prkab2, Abcd3, Msmo1, Prkaa1, Fasn, Pla2g1b, Olah, Cbr4, Prkag2, Pccb, Acly, Nr1h3, Fads6, Acacb, Degs1, Prkab1, Abcd1, Hadhb, Slc25a17, Cpt1c, Eci1, Lep, Acox3, Bdh2, Cpt1b, Adipoq, Decr1, Ppard, Eci3, Echs1, Ech1, Acadm, Pex7, Hadha, Ehhadh, Hadh, Sesn2, Fads1, 4833423E24Rik, Fads2, Elovl5, Elovl3, Decr2, Lta4h, Ltc4s, Cyp4f13, Alox5, Ncf1, Hpgd, Pdpn, Ptgr1, Ptgr2, Tnfrsf1a, Pdpn, Lpin1, Lpin2, Eci2, Faah, Acot7, Lpin3, Dld, Lias, Lipt2, Cyp4v3, Adh7, Elovl7, Elovl4, |

TABLE 2-continued

Genes included in Pathway Terms for FIGS. 1, 3A-3E, 3K, 4A, 4B, 5A, 11-14, 20A, 20B

| Pathway | Gene List |
|---|---|
| | Elovl1, Elovl6, Alox15, Sstr4, Cyp1b1, Cyp2j5, Cyp4f14, Cyp2c54, Cyp2d12, Cyp2d11, Cyp2d34, Cyp2d22, Cyp2d9, Cyp2d40, Cyp2d10, Mapk3, Cyp2j13, Aloxe3, Alox8, Cyp2j9, Cyp2j11, Alox12b, Alox12e, Cyp2j8, Cyp2ab1, Alox12, Cyp2j6, Cyp2j12, Daglb, Dagla, Cyp2c55, Cyp2c50, Rnpepl1, Prg3, Cotl1, Ggt5, Fcer1a, Syk, 2010111101Rik, Ggt1, Mgst2, Pla2g5, Rnpep, Alox5ap, Pla2g3, Cyp2c69, Cyp2g1, Cyp2c44, Cyp2b23, Cyp2f2, Cyp2c70, Cyp2c66, Cyp2a22, Cyp2b19, Cyp2a12, Cyp2b13, Cyp2e1, Cyp2c38, Cyp2b10, Cyp2c40, Cyp2c39, Cyp2t4, Cyp2b9, Cyp2c67, Cyp2c29, Cyp2c37, Cyp2c68, Cyp2s1, Cyp2c65, Gcdh, Hao2, Mapk14, Adipor2, Cygb, Pparg, Adipor1, Por, Acss1, Acss2, Ces1f, Ces1d, Tecr, Hacd3, Hacd2, Pecr, Hacd1, Hacd4, Acad10, Acads, Acad9, Acadvl, Etfdh, Acad8, Acad12, Ivd, Acoxl, Etfa, Acadl, Acadsb, Acad11, Cyp4a31, Cyp4a32, Lipe, Asah2, Myo5a, Plp1, Qk, Tyrp1, Thnsl2, Aldh5a1, Oxsm, Scd3, Scd2 |
| Glucose metabolism | Akt1, Ppp1r3b, Mtor, Ppp1r3e, Ppp1ca, Ppp1r3d, Ppp1r3f, Ppp1cb, Inpp5k, Gnmt, Nr3c1, Nln, Lep, Pdk2, Fbp1, Slc35b4, Acadm, Rora, Mlycd, Lcmt1, Igfbp3, Fam132a, Igfbp5, Adipoq, Pdk1, Sirt1, Ncoa2, C1qtnf1, Pdk3, Pdk4, Igfbp4, Tff3, Nkx1-1, Adipor1, Rorc, Irs2, Irs1, Mup4, Pmaip1, Rgn, Mup9, Akt2, Mup20, Mup12, Mup19, Mup16, Foxa2, Ranbp2, Park2, Cox11, Gckr, Midn, Bad, Dusp12, Pfkfb1, Nr1d1, Foxo1, Tcf7l2, Supt20, Kat2b, Gcg, Wdr5, Kat2a, Pgam1, Tigar, Enpp1, Grb10, Pask, Clk2, Sik1, Serpina12, C1qtnf3, Lepr, Il6, Gck, Smek1, Ppara, Arpp19, Stk11, Smek2, Ptpn2, Pth, C1qtnf2, Dyrk2, Insr, Igf2, Ins2, Ppp1r3g, Igf1, Epm2aip1, Adra1b, Pomc, Khk, Gcgr, Phlda2, Ogt, Sesn2, Trp53, Actn3 |
| Oxidative phosphorylation | Ndufb11, Atp6v1h, Cox6b1, Atp6v1b1, Atp6v0b, Atp4a, Atp4b, Atp5a1, Atp5b, Atp5c1, Atp5f1, Atp5g1, Atp5j, Atp5k, Atp6v1a, Atp6v1b2, Atp6v0d1, Atp6v1e1, Atp6v0e, Atp6v0a1, Atp6v0c, Cox17, Cox4i1, Cox5a, Cox5b, Cox6a1, Cox6a2, Cox6c, Cox7a1, Cox7a2, Cox7c, Cox8a, Cox8b, Atp6v0a4, Atp6, Atp8, Cox1, Cox2, Cox3, Cytb, Nd1, Nd2, Nd3, Nd4, Nd4l, Nd5, Nd6, Ndufa2, Ndufa4, Ndufs4, Ndufv1, Atp12a, Cox7a2l, Atp6v0a2, Uqcrq, Uqcrc1, Ndufs8, Cox15, Ndufs2, Ndufs1, Atp5g3, Ndufb6, Gm4943, Atp6v0d2, Tcirg1, Atp5l, Atp5o, Cox6b2, Atp6v1g3, Ndufs6, Ndufa4l2, Ndufa1, Atp6ap1, Atp5j2, Ndufs5, Atp5d, Ndufb5, Sdhc, Ndufa3, Ndufa9, Cox7b, Atp6v1f, Uqcr10, Ndufb9, Atp6v1g2, Atp6v1g1, Atp6v1c1, Ndufc1, Ndufa12, Ndufa7, Cyc1, Ndufb3, Uqcrh, Uqcr11, Uqcrfs1, Ndufb7, Sdhd, Sdha, Uqcrc2, Atp5e, Ndufa6, Ndufa13, Ndufb8, Ndufa10, Uqcrb, Sdhb, Ppa1, Atp5g2, Ndufb4, Ndufc2, Ndufb2, Ndufa5, Ndufb10, Ndufs3, Ndufa8, Atp6v1c2, Cox11, Ndufa11, Ndufab1, Cox10, Atp5h, Ndufv2, Atp6v1d, Ppa2, Atp6v1e2, Ndufs7, Cox8c, Atp6v0e2, Lhpp, Cox7b2, Ndufv3, Cox4i2, ENSMUSG00000064341, ENSMUSG00000064345; ENSMGSG00000064360, ENSMUSG00000064363, ENSMUSG00000065947, ENSMUSG00000064367, ENSMUSG00000064368, ENSMUSG00000064370, ENSMUSG00000064351, ENSMUSG00000064354, ENSMUSG00000064358, ENSMUSG00000064357, ENSMUSG00000064356 |
| Antioxidant metabolism | Gpx1, Gpx2, Gpx3, Gpx4, Gpx5, Gpx6, Gpx7, Gstk1, Gstp1, Ehd2, Prdx1, Prdx2, Prdx3, Prdx4, Prdx5, Prdx6, Apc, Cat, Ctsb, Duox1, Epx, Lpo, Mpo, Ptgs1, Ptgs2, Rag2, Serpinb1b, Tpo, Alb, Gsr, Sod1, Sod3, Srxn1, Txnrd1, Txnrd2, Txnrd3 |
| ROS metabolism | Sod1, Sod2, Sod3, Ccs, Cyba, Ncf1, Ncf2, Nos2, Nox1, Nox4, Noxa1, Noxo1, Recql4, Scd1, Ucp2, Aox1, Fmo2, Il19, Il22, Als2, Apoe, Cat, Ccl5, Ctsb, Duox1, Epx, Ercc2, Ercc6, Fth1, Gclc, Gclm, Gpx1, Gpx2, Gpx3, Gpx4, Gpx5, Gpx6, Gpx7, Gsr, Gss, Hmox1, Hspa1a, Idh1, Krt1, Mpo, Nqo1, Park7, Prdx1, Prdx2, Prdx6, Prnp, Psmb5, Sod1, Sqstm1, Tpo, Txn1, Txnip, Txnrd1, Txnrd2, Ucp3, Xpa |
| DNA damage and repair | Brca2, Ddb2, Dclre1a, Ercc1, Ercc2, Fancc, Lig1, Nthl1, Ogg1, Pcna, Pole, Rpa1, Trp53, Xpa, Xpc, Apex1, Fen1, Lig1, Mbd4, Mpg, Nthl1, Ogg1, Parp1, Parp2, Pcna, Pole, Trp53, Ung, Xrcc1, Wrn, Abl1, Exo1, Mlh1, Mlh3, Msh2, Msh3, Pcna, Pms2, Atm, Blm, Brca1, Brca2, Chek1, H2afx, Hus1, Lig1, Mdc1, Mlh1, Mre11a, Nbn, Prkdc, Rad50, Rad51, Rad52, Rpa1, Trp53bp1, Xrcc2, Xrcc6, Atrx, Brip1, Chek2, Fanca, Fancd2, Fancg, Gadd45a, Gadd45g, Mgmt, Polh, Poli, Pttg1, Rad1, Rad17, Rad18, Rad21, Rad51c, Rad51b, Rad9a, Rev1, Rnf8, Smc1a, Smc3, Sumo1, Topbp1, Xrcc3 |
| Mitochondrial transport | Aip, Bak1, Bcl2, Bcl2l1, Bnip3, Cpt1b, Cpt2, Dnajc19, Timm10b, Grpel1, Hsp90aa1, Hspd1, Immp2l, Mfn2, Mipep, Mtx2, Stard3, Trp53, Tspo, Ucp1, Ucp2, Ucp3 |

(E) Top Enriched Pathways Based on IPA Analysis

Table 3 lists the 10 most enriched pathways based on IPA analysis. FIG. 1 of U.S. Ser. No. 62/366,211, filed on Jul. 25, 2016, provides the results of our preliminary analysis of the top enriched pathways between D2 mice and D2-Gpnmb+ control (the disclosure of which is incorporated by reference).

TABLE 3

Ten most enriched pathways (IPA analysis)

| Rank | Pathway | Comparison | -log p value |
|---|---|---|---|
| 1 | EIF2 signaling | D2 Group 2 vs. D2-Gpnmb+ | 47.6 |
| 2 | Oxidative phosphorylation | D2 Group 2 vs. D2-Gpnmb+ | 26.6 |
| 3 | Mitochondrial dysfunction | D2 Group 2 vs. D2-Gpnmb+ | 23.5 |
| 4 | Regulation of eIF4 and p70S6K signaling | D2 Group 2 vs. D2-Gpnmb+ | 19.7 |
| 5 | mTOR signaling | D2 Group 2 vs. D2-Gpnmb+ | 18.3 |
| 6 | Phototransduction pathway | D2 Group 2 vs. D2-Gpnmb+ | 8.8 |
| 7 | Fcγ receptor-mediated phagocytosis in macrophages and monocytes | D2 Group 2 vs. D2-Gpnmb+ | 6.3 |
| 8 | IL-8 signaling | D2 Group 2 vs. D2-Gpnmb+ | 5.1 |
| 9 | GABA receptor signaling | D2 Group 2 vs. D2-Gpnmb+ | 4.9 |
| 10 | Huntington's disease signaling | D2 Group 2 vs. D2-Gpnmb+ | 4.7 |
| 1 | EIF2 signaling | D2 Group 3 vs. D2-Gpnmb+ | 30.4 |
| 2 | Oxidative phosphorylation | D2 Group 3 vs. D2-Gpnmb+ | 21.4 |
| 3 | Mitochondrial dysfunction | D2 Group 3 vs. D2-Gpnmb+ | 17.4 |
| 4 | mTOR signaling | D2 Group 3 vs. D2-Gpnmb+ | 13.5 |
| 5 | Phototransduction pathway | D2 Group 3 vs. D2-Gpnmb+ | 11.8 |
| 6 | Regulation of eIF4 and p70S6K signaling | D2 Group 3 vs. D2-Gpnmb+ | 11.6 |
| 7 | Glutamate receptor signaling | D2 Group 3 vs. D2-Gpnmb+ | 5.6 |
| 8 | Protein kinase A signaling | D2 Group 3 vs. D2-Gpnmb+ | 5.5 |
| 9 | Synaptic long term potentiation | D2 Group 3 vs. D2-Gpnmb+ | 5.5 |
| 10 | Cardiac β-adrenergic signaling | D2 Group 3 vs. D2-Gpnmb+ | 5.3 |
| 1 | EIF2 signaling | D2 Group 4 vs. D2-Gpnmb+ | 24.9 |
| 2 | Mitochondrial dysfunction | D2 Group 4 vs. D2-Gpnmb+ | 23.7 |
| 3 | Oxidative phosphorylation | D2 Group 4 vs. D2-Gpnmb+ | 20.9 |
| 4 | Axonal guidance signaling | D2 Group 4 vs. D2-Gpnmb+ | 14.0 |
| 5 | Regulation of eIF4 and p70S6K signaling | D2 Group 4 vs. D2-Gpnmb+ | 13.2 |
| 6 | mTOR signaling | D2 Group 4 vs. D2-Gpnmb+ | 12.3 |
| 7 | CREB signaling in neurons | D2 Group 4 vs. D2-Gpnmb+ | 11.0 |
| 8 | Signaling by Rho family GTPases | D2 Group 4 vs. D2-Gpnmb+ | 9.35 |
| 9 | Huntington's disease signaling | D2 Group 4 vs. D2-Gpnmb+ | 9.1 |
| 10 | Breast cancer regulation by Stathmin1 | D2 Group 4 vs. D2-Gpnmb+ | 9.0 |

Pathway analysis identified enrichment of eIF2 and mTOR signaling transcripts (FIGS. 3B and 3F), with eIF2 signaling being the most enriched pathway in Group 2 (the first distinguishable stage from controls).

There was significant up-regulation of mitochondrial fission genes (Dnm1 and Fis1) (FIG. 3D) and significant changes to the mitochondrial unfolded protein response (UPRmt) (FIG. 3E), further indicating mitochondrial dysfunction.

(F) Morphology Reveals Mitochondrial Abnormalities

In this study, we evaluated morphological alternation by performing electron microscopy (EM) on the retina in these mice. EM currently gives us the greatest resolution available to study the morphology of intracellular organelles (such as mitochondria). EM revealed dysfunctional mitochondria with reduced mitochondrial cristae volume in the dendrites of D2 RGCs, but not in those of control RGCs (FIGS. 4A and 4B). These mitochondrial EM findings coincide with synapse loss in 9-month old D2 retinas, with early decreases in pattern electroretinogram amplitude (PERG, a sensitive measure of RGC activity in both human patients and animals) (FIG. 14), and an increase in retinal cytochrome c levels (FIG. 3G).

These data presented clearly demonstrate that mitochondrial perturbations are among the very first changes occurring within RGCs in vivo in an inherited age-related glaucoma. The present finding is consistent with the reported in vitro study where cultured cells, when subjected to pressure, undergo mitochondrial abnormalities. The in vitro study, however, fails to establish (while the present finding establishes) how early the mitochondrial abnormalities occur in glaucoma in vivo.

In summary, the present RNA-seq study revealed transcriptional processing and mitochondrial dysfunction in the RGCs of glaucoma-prone eyes with undetectable neurodegenerative phenotype. Mitochondrial dysfunction was confirmed through targeted metabolic assays and EM, showing abnormal mitochondria early in glaucoma along with an early energy crisis.

Example 2 Metabolic Profiling

To determine whether mitochondrial dysfunction/energy crisis was present in D2 mice (as compared to the control D2-Gpnmb+ mice), during the pre- and the earliest stages of disease (i.e., at 4 months (pre-glaucoma), at 9 months of age when high IOP is present without any neurodegeneration, and at 12 months when neurodegeneration is present/severe in the majority of eyes), we performed metabolomic profiling of neural retinas.

We performed additional metabolic profiling of neural retinas from 4-, 9-, and 12-month D2 and D2-Gpnmb+ eyes. Metabolic profiling was performed using targeted assays following the manufacturers recommendations. The following metabolites were profiled: NAD+/NADH (i.e. total NAD, NAD(t)), GSH/GSSG (i.e. total glutathione, glutathione(t)), and pyruvate. There were significant age-related decreases in all profiled metabolites. These metabolic profile changes occur prior to any detectable neurodegenerative phenotype and also occur in age-matched, no glaucoma, control D2-Gpnmb+ retinas (FIG. 5A-D).

As these are key molecules in cellular metabolism and protection from cellular stress, these age-dependent declines are expected to sensitize retinal neurons to disease related stresses and mitochondrial dysfunction.

Figure 6A:
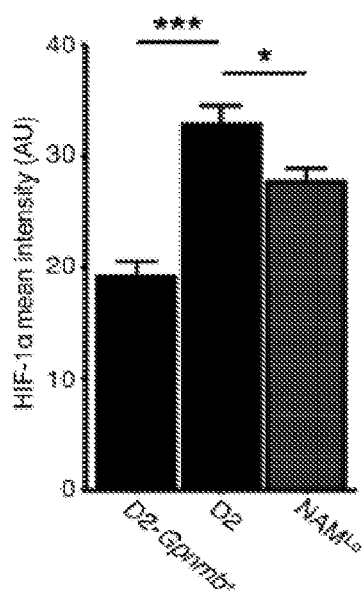
FIGS. 6A and 6B show that NAM treatment (550 mg/kg/day) lessens upregulation in early glaucoma as assessed by immunostaining (n=6/group). *=P<0.05, ***=P<0.001. The result demonstrates that NAM treatment prevents early damaging changes in D2 glaucoma.
Figure 6B:
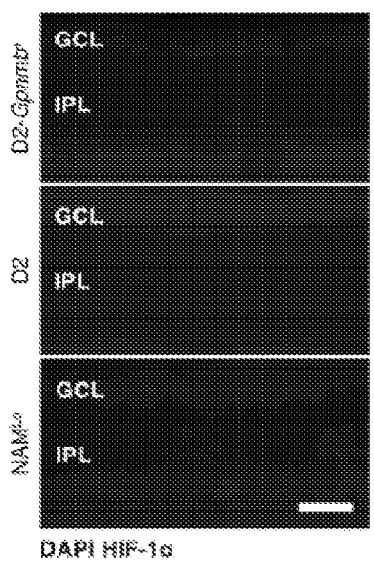

Our data show that HIF-1α (a key metabolic regulator during perturbed redox states) was induced in the ganglion cell layer early in glaucoma (by RNA-seq and by immunostaining: FIGS. 6A and 6B). This further suggests that RGCs undergo perturbed metabolism (and subsequent excess generation of reactive oxygen species) early in glaucoma.

To study the link between elevated IOP, mitochondrial dysfunction, metabolite depletion (especially NAD) and cellular stress, we examined the roles of DNA damage and PARPs (poly-ADP-ribose polymerase) in early glaucoma. PARPs respond to DNA-damage and are major consumers of NAD within cells.

Figure 7A:
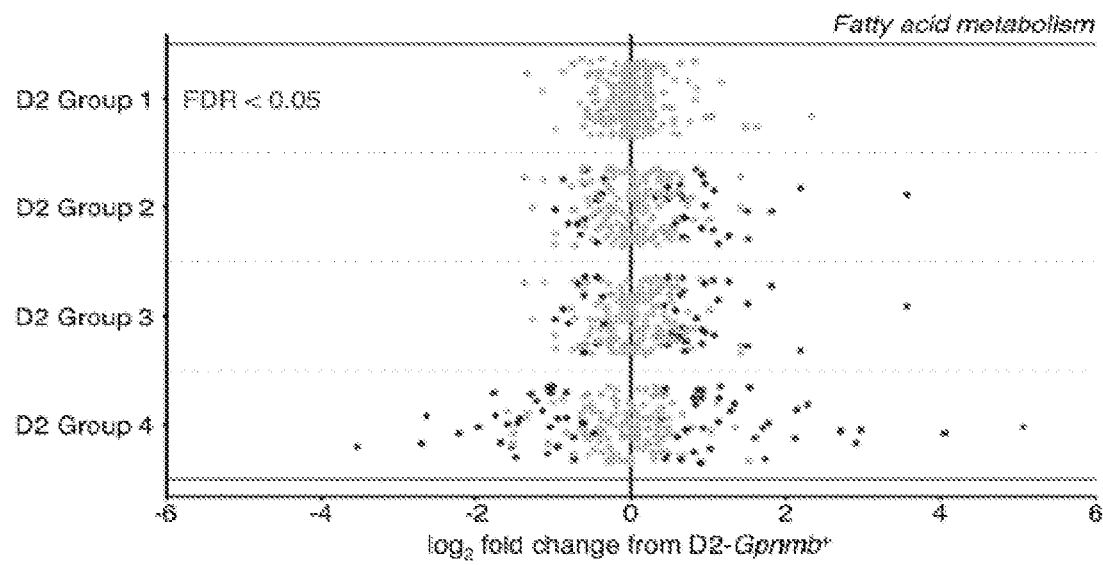
FIG. 7A shows that RNA-sequencing identifies changes to cellular metabolism—specifically, fatty acid metabolism gene changes in D2 glaucoma. Dots represent individual genes, grey or lighter dots=not differentially expressed, red or darker dots=differentially expressed at q<0.05.
Figure 7B:
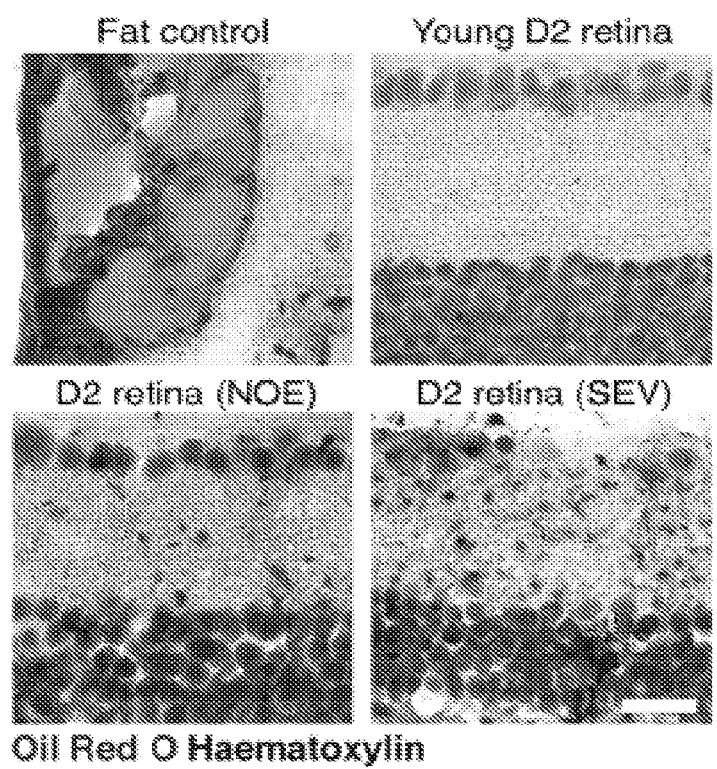
FIG. 7B shows inner-retina extracellular lipid droplet formation in IOP-insulted, aged D2 eyes as stained using Oil Red O. Staining was present in D2 eyes which had both no (NOE) or severe (SEV) optic nerve degeneration. Extraocular fat was used as a positive control (n=6/group), Scale bar=25 μm.

The RNA-seq dataset suggests that RGCs go through a period of mitochondrial stress and metabolite depletion, potentially moving towards fatty acid metabolism (corresponding with an increase in lipid deposits in the retina during early glaucoma, FIGS. 7A and 7B).

Figure 8A:
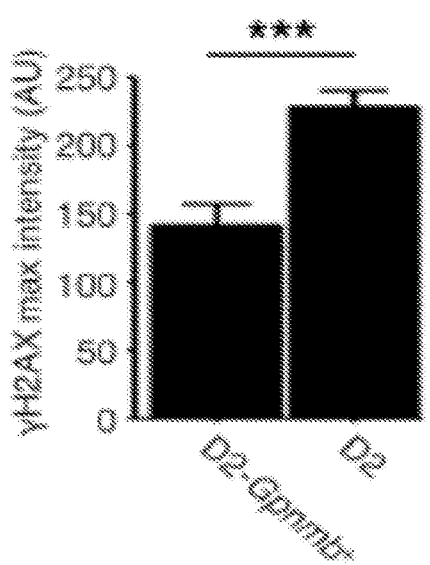
FIGS. 8A and 8B show increased levels of DNA damage as assessed by γH2AX staining (n=6/group). The result is represented as bar graph of γH2AX staining max intensity (AU). ***=P<0.001.
Figure 8B:
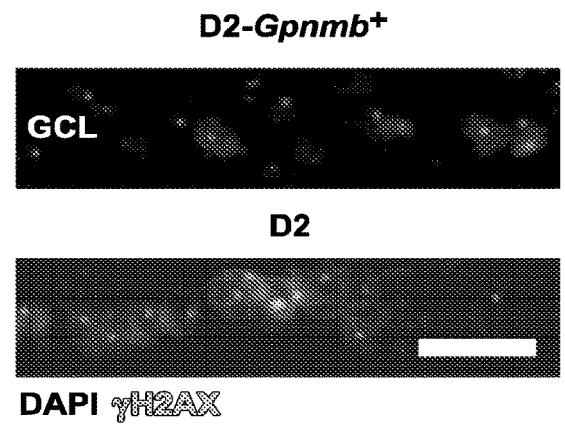

One consequence of fatty acid β-oxidation is the increased generation of free radicals/reactive oxygen species (ROS). Thus, we further assessed retinas for signs of ROS-induced DNA damage (by RNA-seq, FIG. 3F; and γ-H2AX immunostaining, 3 sensitive marker of dsDNA breaks). γ-H2AX$^+$ nuclei were found to be present throughout the ganglion cell layer of D2 retinas but not controls, indicating that DNA damage increases very early in glaucoma (FIGS. 8A and 8B).

Figure 9A:
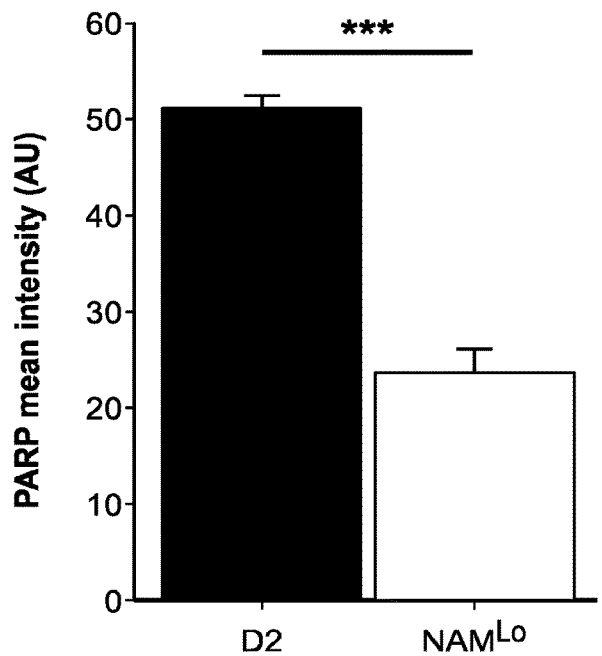
FIGS. 9A and 9B show that NAM prevents PARP activation in glaucoma. PARP is a major constumer of NAD$^+$, and may contribute to NAD(t) decreases in RGCs with age. After administration of NAM (550 mg/kg/day), PARP expression (pan-PARP immunostaining) is reduced in NAM-treated retinas (n=6/group). ***=P<0.001. Scale bar 15 μm.
Figure 9B:
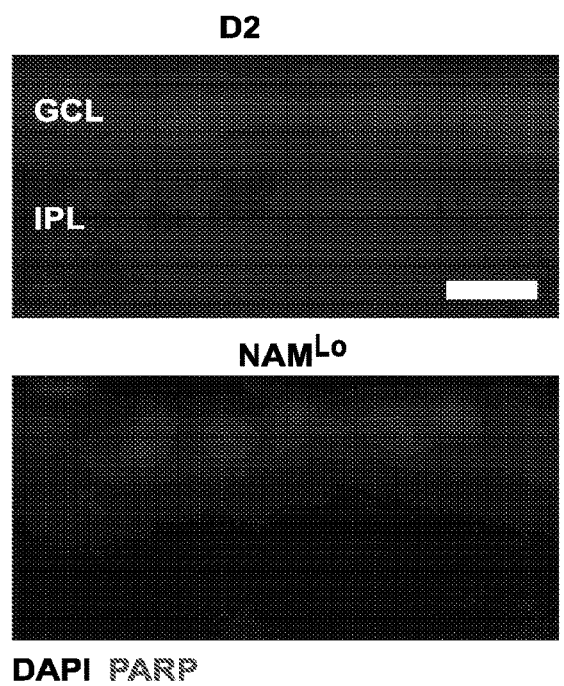

PARP activity was found to be induced in RGCs with age (FIGS. 9A and 9B), providing a link between DNA damage, and increased metabolic stress within RGCs. Our finding is consistent with the hypothesis that PARPs are induced by DNA damage, and they are major NAD$^+$ consuming enzymes, and inhibit glycolysis through PAR inhibition of hexokinase.

The D2 mouse model clearly support the paradigm that age is major risk factor for glaucoma and a variety of other neurodegenerative diseases. Our metabolic profile data suggest how increasing age may increase neuronal vulnerability to damage through depletion of essential neuronal metabolites.

Altogether, data presented herein support a new model where age-dependent declines of NAD and glutathione in the retina sensitize RGCs to glaucoma and possibly other age-related diseases. RGCs are particularly vulnerable to harmfully high IOP and glaucoma. Thus, age-dependent metabolite decline, as well as PARP activation within RGCs, conspire to disrupt cellular metabolism and increase susceptibility to ongoing IOP-induced stresses, leading to critical damage of RGCs.

In D2 mice, glaucomatous neurodegeneration is age related, chronic and asynchronous. During development of D2 glaucoma, RGCs experience an early loss of connectivity, as well as metabolic, and molecular changes, all of which occur prior to gross soma loss, axon loss, and degeneration of the optic nerve. These early changes are expected to decrease the reliability of cellular metabolism and increase the probability of cellular failure with age when RGCs are under ongoing IOP-induced stress.

In summary, based on RNA-sequencing and metabolic assays, we discovered that neurons in the retina go through a metabolic crisis prior to degenerating. This suggests a key role for metabolic molecules that may alter or supplement the way mitochondria function. Correcting these dysfunctional processes is likely to have benefits beyond glaucoma and relate to more general age-related changes.

The data present so far shows that declining NAD is central to age-related neuronal vulnerability to glaucoma.

Example 3 NAM Protects Neuronal Cell Loss in Axotomy Culture

In this series of study, we examined if increasing the NAD levels can protect insulted eyes from neurodegenerative changes. Axotomy (i.e. the severing of the axon) mimics the acute severe insults seen in some glaucoma, and is an important model to test these more severe insults.

The study is based on the hypothesis that by decreasing the probability of metabolic/energetic failure, it would render the RGCs more resilient to the external stresses.

Figure 22A:
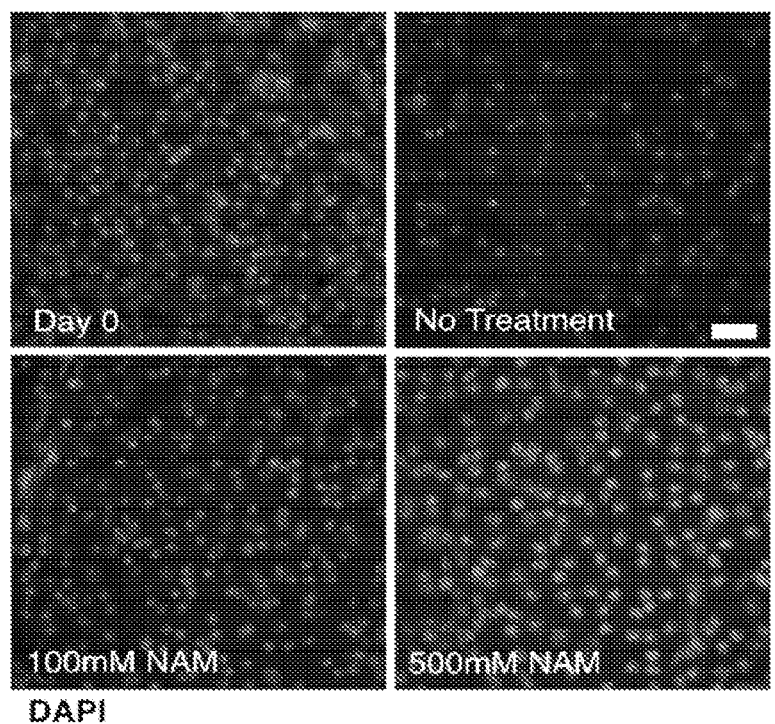
FIGS. 22A and 22B show that NAM is protective against neurodegenerative treatments that model glaucomatous insults. NAM showed an attractive dose-response effect in protecting ganglion cell layer cells (GCL cells) from death (FIG. 22A) and pre-apoptotic nuclear shrinkage (FIG. 22B). In an axotomy culture model of retinal ganglion cell damage, addition of nicotinamide (NAM) protects against cell shrinkage (sign of cell apoptosis and dysfunction) in a dose-dependent manner (5 days post-axotomy). Mean nuclear diameter of DAPI-labeled nuclei from D2 mice retinas exposed to different concentrations of NAM for 5 days was measured (including Day 0 control (normal retina), No treatment (5 days post-axotomy), 100 mM and 500 mM NAM (5 days post-axotomy). NAM treated retinas were indistinguishable from uninjured, baseline controls (Day 0). There were also significant protective effects treating retinas with β-NAD & β-NMN (n=8 retinas/group). ***=P<0.001. Scale bar=20 μm.
Figure 22B:
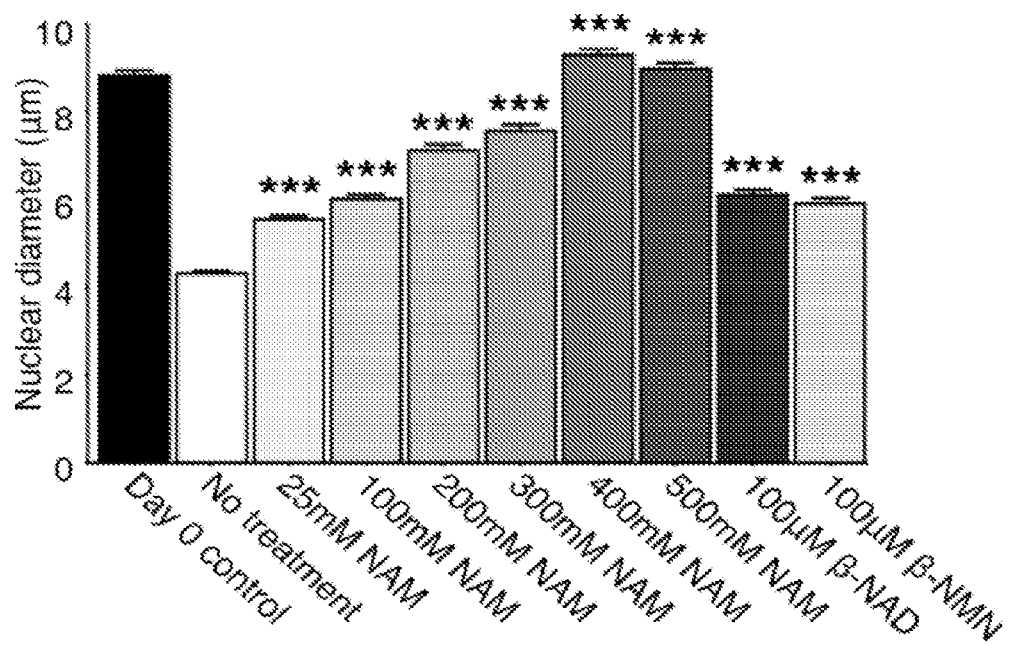

A plethora of drugs with actions at the mitochondria were tested in axotomy culture, in order to identify drug candidates that potentially antagonize the mitochondrial dysfunction/energy crisis observed in the D2 mice. The screen identified nicotinamide (NAM) as giving the most robust protection against nuclear shrinkage, a hallmark feature of nuclear remodeling pre-apoptosis. FIGS. 22A and 22B.

The above in vitro finding is consistent that the in vivo results in Example 3.

Example 4 NAM Alleviates Glaucoma in D2 Mice

We conducted an in vivo experiment using a large cohort of D2 mice.

In this experiment, optic nerves were classified into three damage levels: NO (no glaucoma), MOD (Moderate damage), and SEV (severe damage).

Experimental D2 mice were divided into the following groups and were given:
W=water (standard mouse water)
NAM or NAM$^{Lo}$=550 mg/k/d NAM in drinking water
Early=early start=pre-glaucoma=6-month of age (i.e. prophylactic)
Late=late start=during glaucoma=9-month of age (when mice already have high IOP, i.e. interventional, and more relative to human glaucoma)

NAD levels were increased by administering nicotinamide (NAM; a precursor of NAD) to D2 mice (See. FIGS. 5A, 11-14, 20A, and 20B). Mice were then assessed at 12-month for optic nerve damage, soma loss, visual function, and axonal transport.

Figure 5E:
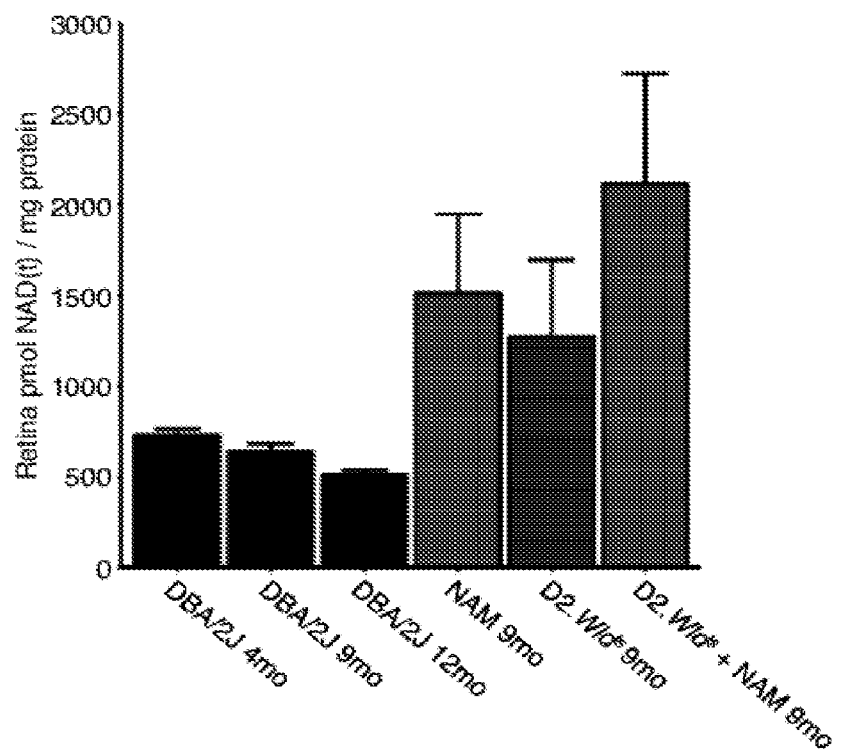
FIG. 5E shows a decrease in total NAD (NAD(t)) (i.e., NAD$^+$+NADH) in D2 retinas with age that is restored by NAM treatment (550 mg/kg/day) or the addition of the Wld$^S$ allele. Combination of Wld$^S$ and NAM affords additional benefit.

NAM administration in drinking water (550 mg/kg/d, NAM$^{Lo}$ prevented the decline of NAD levels through to 12-month (a standard end stage for assessing neurodegeneration in this glaucoma model) (FIGS. 5A and 5E).

(A) NAM Protects Mice from All Detectable Signs of Glaucoma

Supporting the neuronal vulnerability hypothesis, NAM did not alter IOP (FIGS. 10A-10D), but it robustly protected from glaucoma, i.e. NAM is a neuroprotective agent. Importantly, NAM was protective both prophylactically (starting at 6-month, early start; prior to IOP elevation in the vast majority of eyes in the colony), and as an intervention (starting at 9-month, late start; when the majority of eyes have had continuing IOP elevation). This signifies that NAM is able to both prevent neuronal injury from occurring as well as limiting neuronal injury to already insulted neurons (FIGS. 11A and 11B). This is important for human disease where treatment would only start once a disease has become symptomatic and thus detectable.

These data support that NAM can be used prophylactically to treat human glaucoma. Either in subjects at risk of glaucoma, for example, due to family history, ocular trauma, known gene mutation, or when IOP is seen to be higher but no glaucomatous damage is present.

(B) NAM Robustly Prevents Retinal Ganglion Cell Dysfunction and Degeneration

Figure 15:
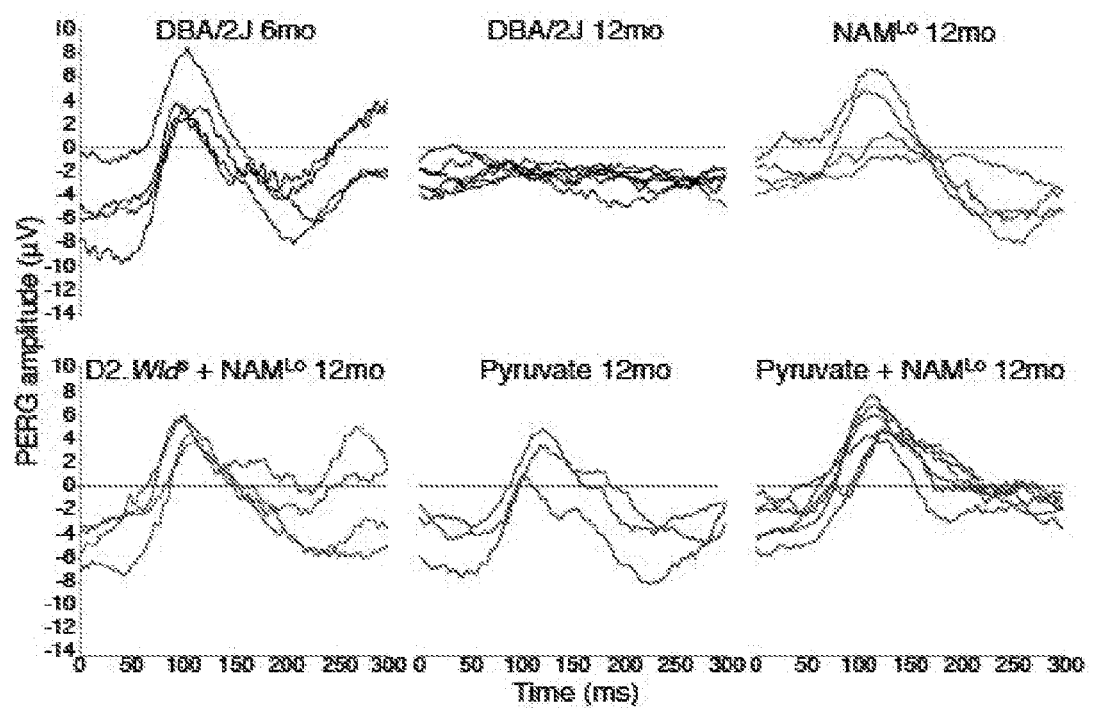
FIG. 15 shows that NAM$^{Lo}$ (550 mg/kg/day) and pyruvate (500 mg/kg/day) protect PERG even in aged mice. Example traces from 6-month and 12-month D2 and 12-month NAM$^{Lo}$-treated mice (550 mg/kg/day) are shown. Results for 12-month pyruvate-treated mice, and NAM$^{Lo}$-treated Wld$^S$ mice are also shown.

NAM significantly reduced the incidence of optic nerve degeneration (FIGS. 11A and 12A), prevented RGC soma loss and retinal thinning (detectable in the human clinic through commonplace methods—e.g. OCT, fundoscopy) (FIGS. 12A and 13A), restored anterograde axonal transport (as assessed by Ct-β tracing; and important early marker of axon dysfunction and degeneration) (FIG. 12A), and visual function as assessed by pattern electroretinography (PERG) (FIGS. 14 and 15), PERG has been shown to be a very sensitive and early measure of glaucomatous visual dysfunction in both humans and animal models (Saleh et al., *Invest Ophthalmol Vis Sci* 48, 4564-4572, 2007); thus NAM prevents the earliest signs of glaucoma.

(C) NAM Protects Early Synapse Loss And Lipid Droplet Formation In Retina

Figure 16A:
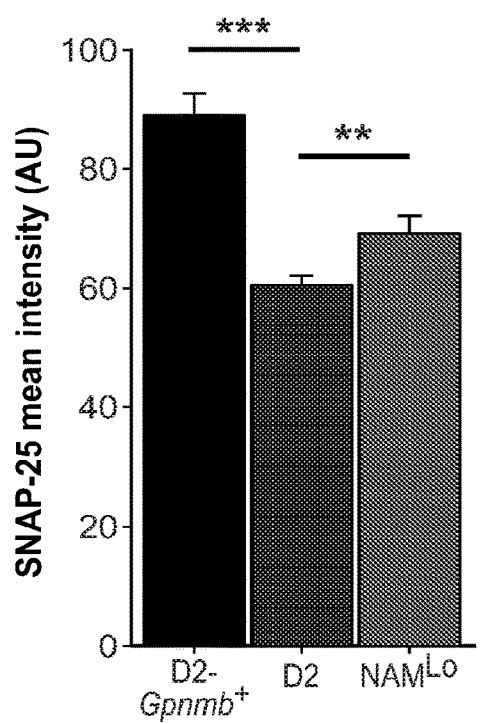
FIGS. 16A and 16B show that NAM$^{Lo}$-treatment (550 mg/kg/day) prevents synapse loss in early glaucoma as assessed by SNAP-25 staining (n=6/group). =P<0.01, *=P<0.001. Scale bar=25 μm.
Figure 16B:
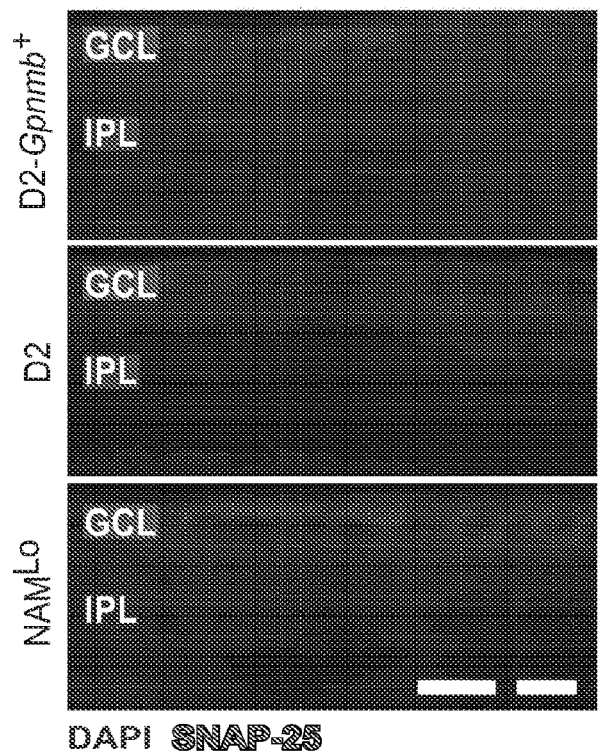
Figure 17A:
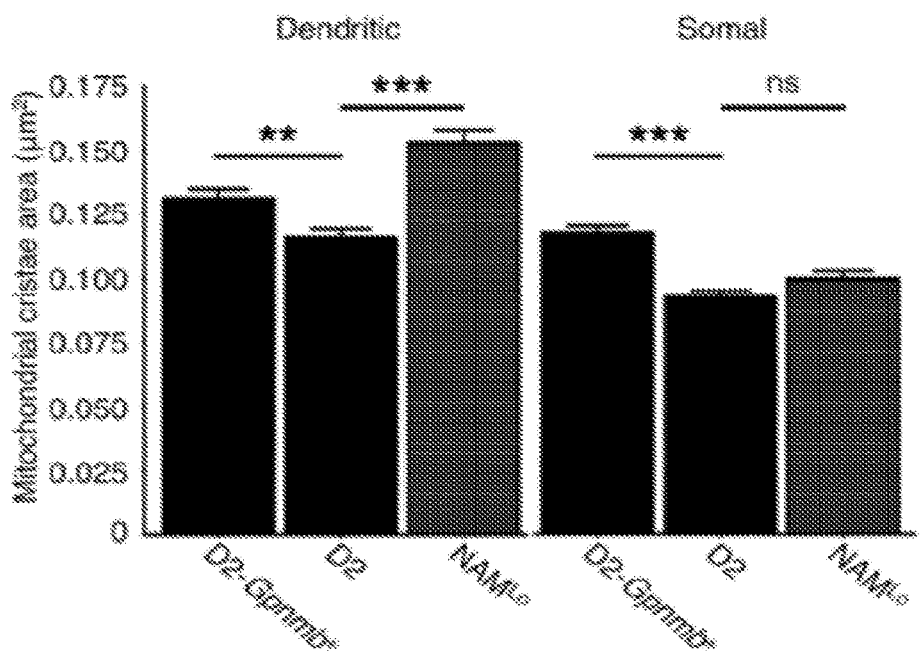
FIGS. 17A and 17B show that NAM (NAM$^{Lo}$=550 mg/kg/day) prevents early mitochondrial dysfunction in dendritic mitochondria as shown in FIGS. 4A and 4B. These data correspond with early changes to PERG and previously reported synapses loss in D2 retinas at 9-month. Thus, elevated IOP induced mitochondrial dysfunction may drive early neurodegenerative changes. =P<0.01, *P<0,001. ns=not statistically significant. Bar scale=350 nm.
Figure 17B:
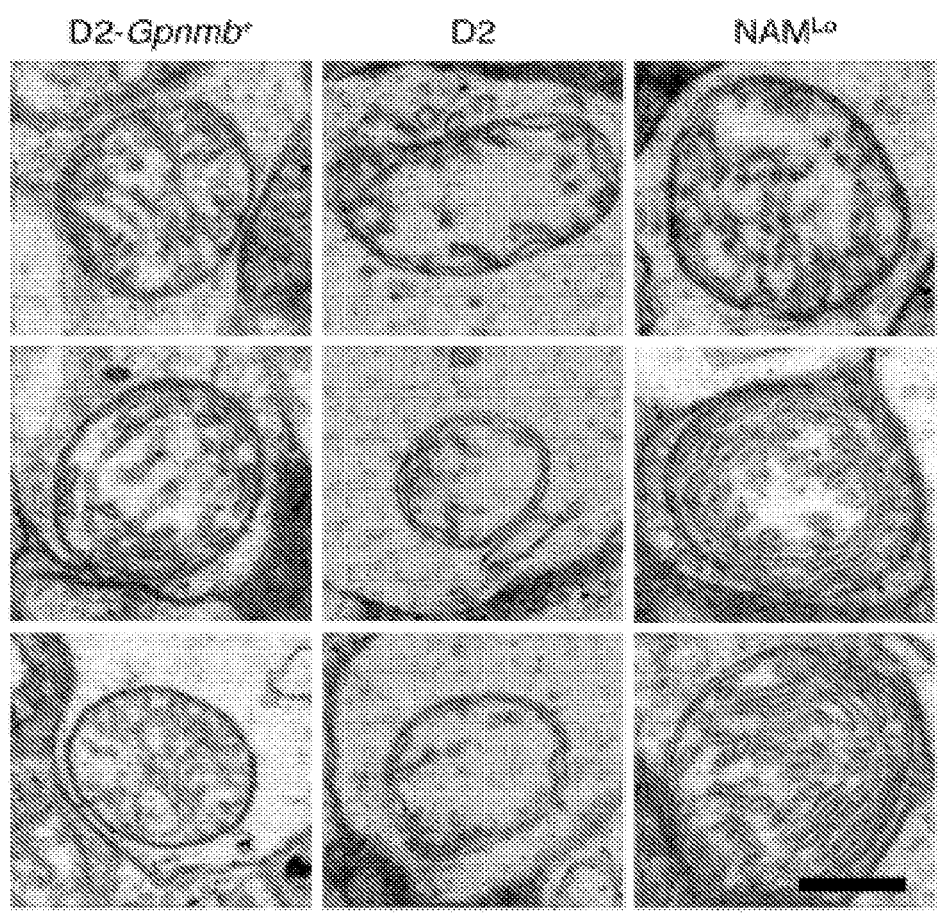

NAM administration also protected against early synapse loss (SNAP-25 immunostaining) that occurs in this model (FIGS. 16A and 16B), and was sufficient to inhibit the formation of dysfunctional mitochondria with abnormal cristae as assessed by EM (FIGS. 17A and 17B).

Figure 18:
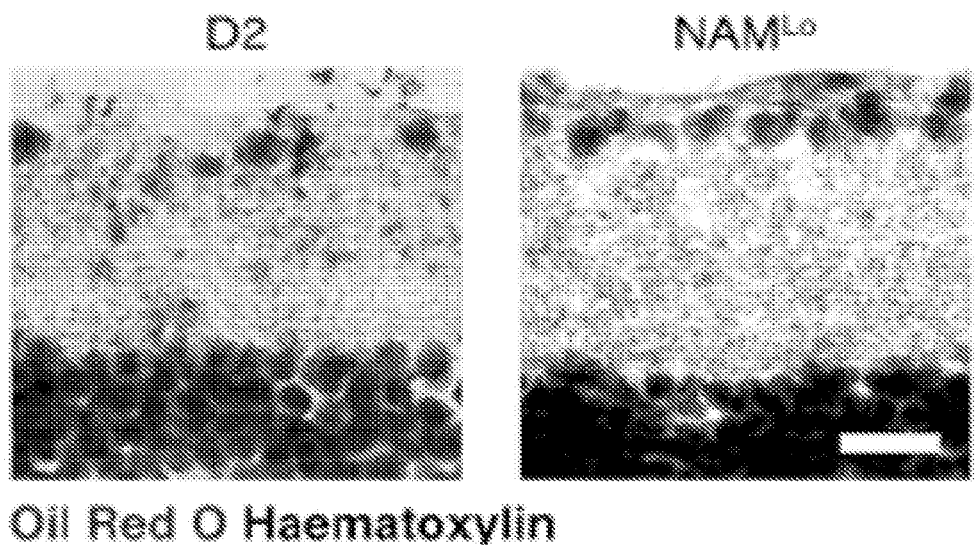
FIG. 18 shows that NAM treatment (550 mg/kg/day) prevents lipid droplet formation in the inner retina (12-month; as in FIG. 7B). Scale bars=25 μm.
Figure 19A:
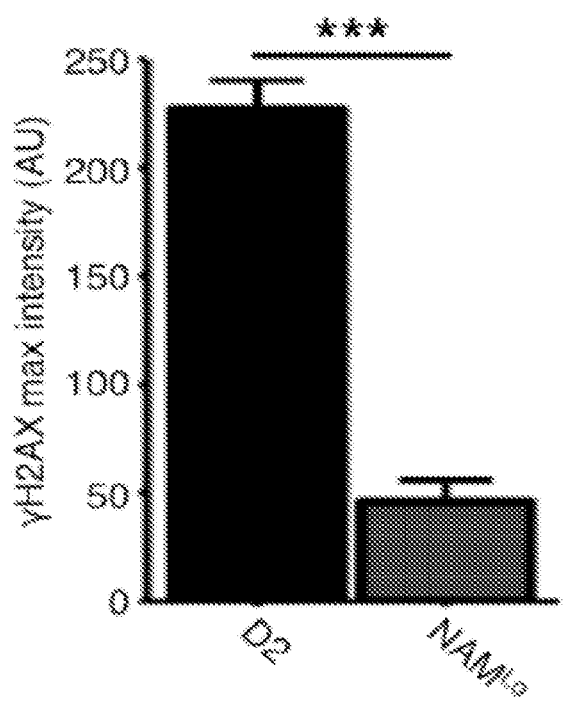
FIGS. 19A and 19B show that NAM treatment (NAM$^{Lo}$=550 mg/kg/day) prevents DNA damage in early glaucoma as assessed by γH2AX staining (n=6/group). ***=P<0.001. Scale bar=25 μm.
Figure 19B:
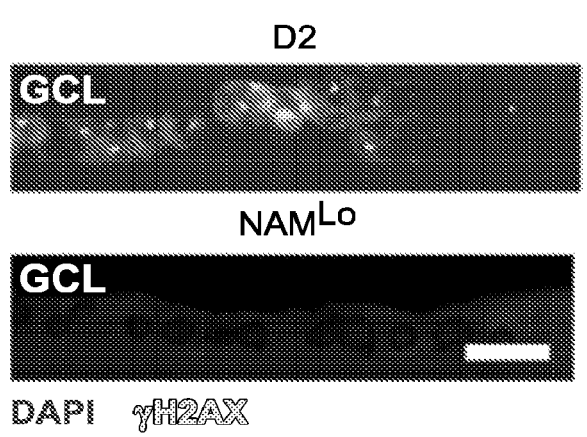
Figure 20A:
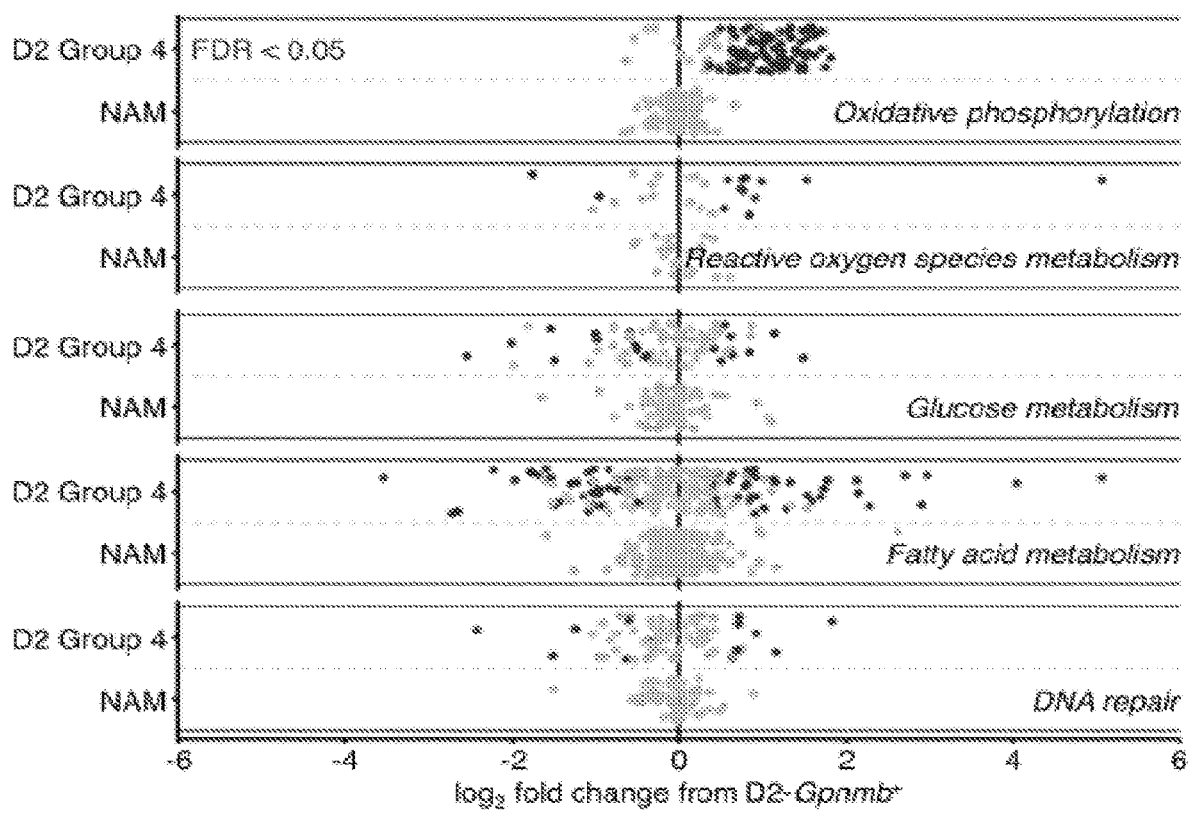
FIG. 20A represents individual gene expression plots showing metabolic and DNA damage pathways are returned to normal in NAM-treated RGCS. Dots represent individual genes, grey or lighter dots=not differentially expressed, red or darker dots=differentially expressed at q<0.05 compared to D2-Gpnmb$^+$ control.
Figure 20B:
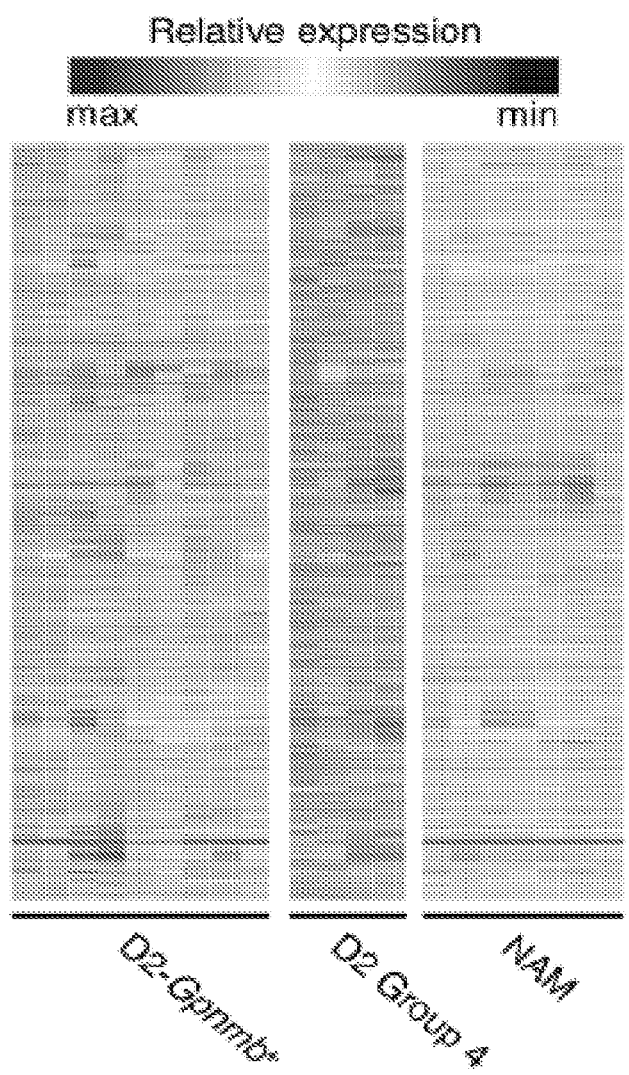
FIG. 20B is a heatmap of gene expression (all expressed genes) showing that NAM-treated RCGs are molecularly similar to controls.
Figure 21A:
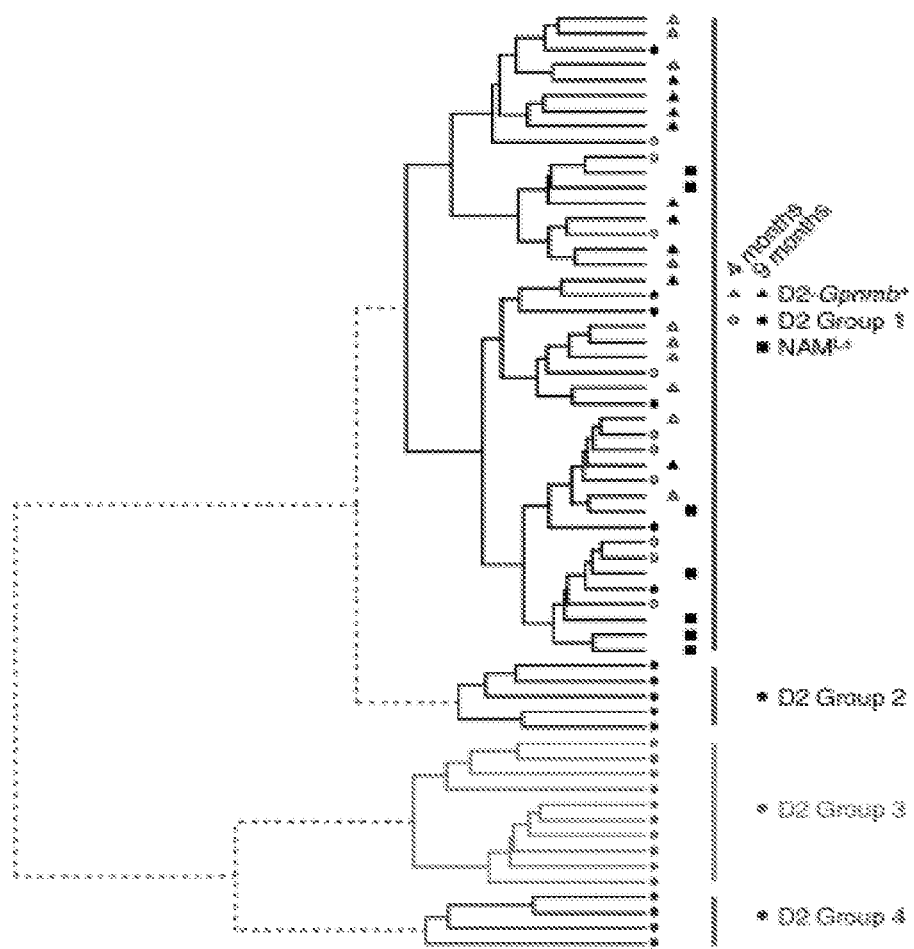
FIG. 21A shows NAM-treated RCGs are molecularly similar to both young and age-matched no glaucoma control RCGs. (Spearman's rho). Circles=samples from D2 RGCs, triangles=samples from D2-Gpnmb$^+$ RGCs, squares=samples from NAM-treated (NAM$^{Lo}$=550 mg/kg/day) RGCs. Thus NAM treatment prevents disease and age-related molecular changes.
Figure 21B:
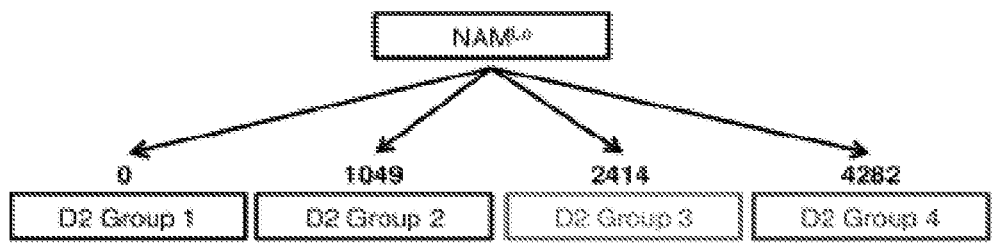
FIG. 21B summarizes the number of differentially expressed genes among the D2 groups (Group 1, Group 2, Group 3, and Group 4) compared to the control D2-Gpnmb$^+$ group.
Figure 21C:
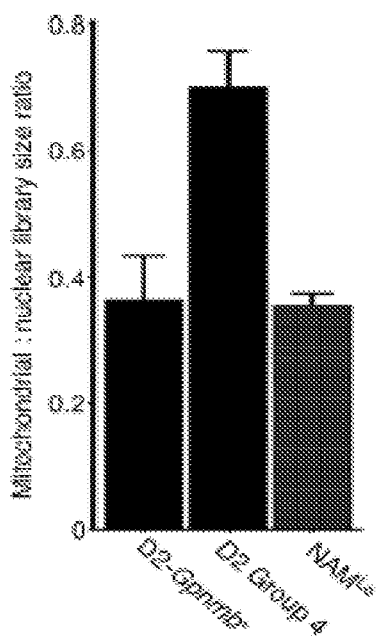
FIGS. 21C and 21F show that NAM-treatment (NAM$^{Lo}$=550 mg/kg/day) prevents transcriptome imbalances and OXPHOS imbalances (mitochondial:nuclear library size ratio) seen in 9-month 132 RGCs.
Figure 21D:
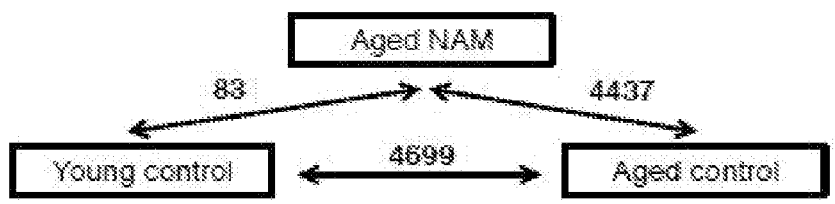
FIG. 21D D2 mice were treated with 550 mg/kg/day nicotinamide in normal drinking water from 6-month of age (Aged NAM). RNA-seq of retinal ganglion cells from NAM-treated mice shows that NAM prevents age- and disease-related gene expression changes. NAM-treated retinal ganglion cells are most similar to young (Young Control) rather than age-matched controls (Aged Control). This indicates that NAM prevents, the age-dependent molecular changes.
Figure 21E:
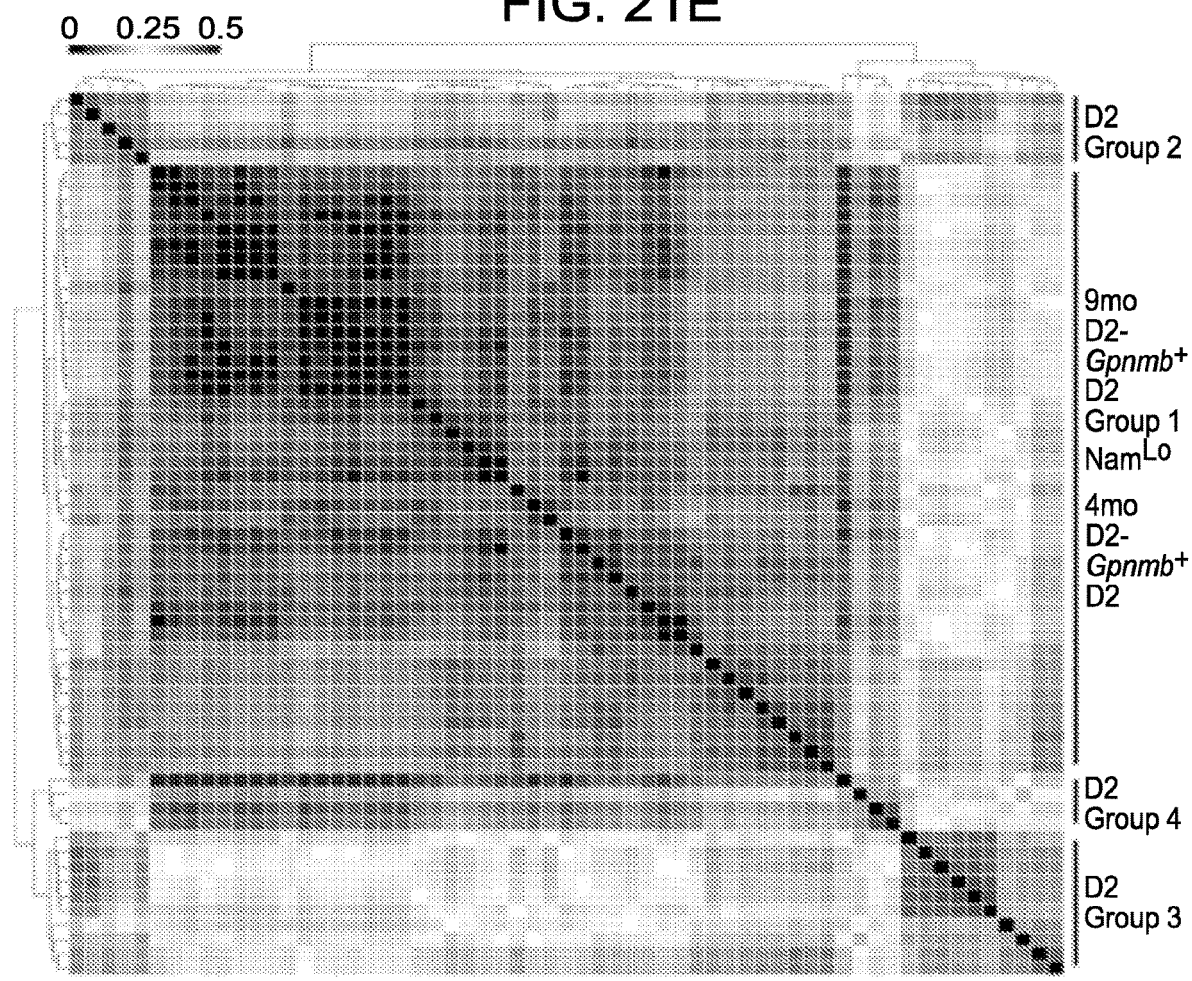
FIG. 21E shows heatmap correlations of all samples (Spearman's rho, blue=highest correlation, red=lowest correlation). Dendrogram from FIG. 21A is shown in grey.
Figure 21F:
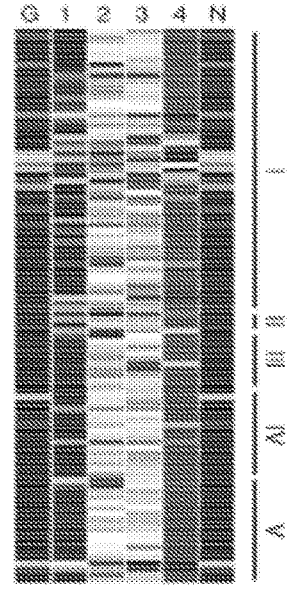

Lipid droplet formation was also prevented in aged D2 retinas (FIG. 18).

(D) NAM Decreases P RP Activation And Prevents Molecular Signs of Glaucoma

NAM also decreased PARP activation, limited levels of DNA damage and transcriptional induction of HIF-1α (FIGS. 9A, 9B, 19A and 19B) reflecting less perturbed cellular metabolism. NAM likely prevents these damaging mechanisms by correcting the upstream effectors—i.e. metabolite depletion and redox buffering within the mitochondrion.

NAM prevented even the earliest molecular signs of glaucoma in the majority of treated eyes as assessed by RNA-seq. NAM treated samples were molecularly similar to controls and clustered among both age-matched and young control samples (FIGS. 20A, 20B, and 21A-21F).

(E) NAM Prevents Age-Related Gene Expression In RGCs

NAM even prevented the vast majority of age-related gene expression changes within RGCs=number of DE genes; 4-month D2-gpNMB+ vs. 9-month D2-Gpnmb+= 4699, 9-month D2-GpnMB+ vs. NAM=4437, 4-month D2Gpnmb+ vs. NAM=83). This remarkable degree of molecular protection highlights the unexpected potency of NAM in decreasing the probability of metabolic disruption and glaucoma in eyes with high IOP. As age is a major risk factor in the pathogenesis of glaucoma, inhibiting damaging age-related changes has the potential to prevent neurodegeneration in many instances of human glaucoma as well as other slowly degenerating neurodegenerative diseases.

In the majority of the treated eyes, NAM administration completely prevents glaucoma, including results based on very sensitive measures of early disease such as PERG. In addition, many ocular and neurodegenerative diseases occur in the elderly due to age-dependent molecular chances that increase susceptibility to damage. NAM treatment prevents age-related molecular changes assessed by gene expression (a very sensitive measure of these changes).

Furthermore, axonal degeneration and somal shrinkage may represent common components in some neurodegenerative diseases. NAM prevents these changes based on the data above at least in glaucoma treatment. Furthermore, the data above shows that NAM prevents axonal degeneration and somal shrinkage in glaucoma.

Example 5 Increasing Dietary NAM Farther Lessens the Degree of IOP Elevation in D2 Mice NAM is believed to be safely tolerated even at high doses. Some studies have suggested an incidence of hepatotoxicity at doses >4 grams NAM per day in humans. However, these resulted from impurities in older preparations. In a more recent survey of 6000 patients on high doses of nicotinamide or niacin, only 3 cases of jaundice were reported. In one of these (on 6 g/day niacin) it resolved after stopping a different but simultaneously administered drug (but not niacin), and in another it resolved even with continuing niacin treatment. Regarding a higher dose of nicotinamide, it has been suggested that abnormal liver enzyme tests do not indicate hepatocellular damage but rather represent changes in liver enzymes expression, which are rapidly reversible when the drug is discontinued. Rare cases of liver toxicity may reflect individual genetic susceptibility or other individual factors. Although the long-term effects of very high doses require further evaluation, experience suggests that risk to benefit ratios of long-term nicotinamide treatment would be highly favorable.

In an attempt to further decrease the probability of glaucoma and protect even more eyes from IOP-induced insults, we used an increased dose of NAM (representing 4 times the original lower dose at 2000 mg/kg/d, $NAM^{Hi}$) administered to D2 mice.

Remarkably, NAM tat this dose) was found to be extremely protective with 93% of treated eyes having no glaucomatous optic nerve damage (FIG. 11A). This represents a ~10 fold decrease in risk factor of developing glaucoma. The degree of protection afforded by administering this single molecule is unprecedented and completely unanticipated.

Figure 10A:
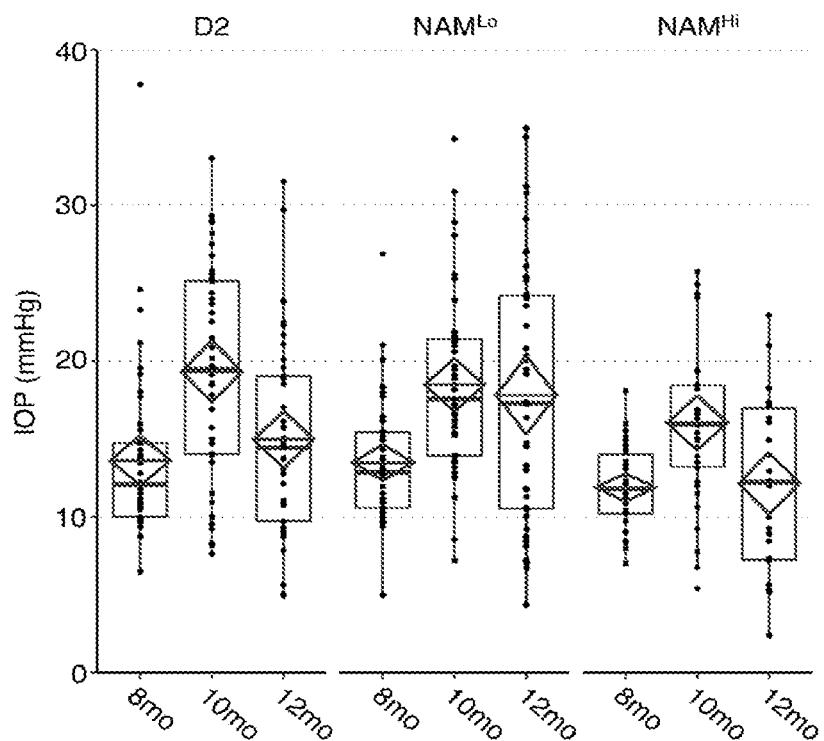
FIGS. 10A & 10C (IOP profiles), and FIGS. 10B & 10D (clinical presentation of IOP elevating iris disease) show that protective strategies do not change clinical disease progression/presentation in treated eyes. Iris disease progressed at a similar rate and reached a severe state in all groups within the same timeframe. NAM$^{Lo}$=550 mg/kg/day. NAM$^{Hi}$=2000 mg/kg/day. Nmnat1=gene therapy by expressing exogenous Nmnat1 (on viral vector).
Figure 10B:
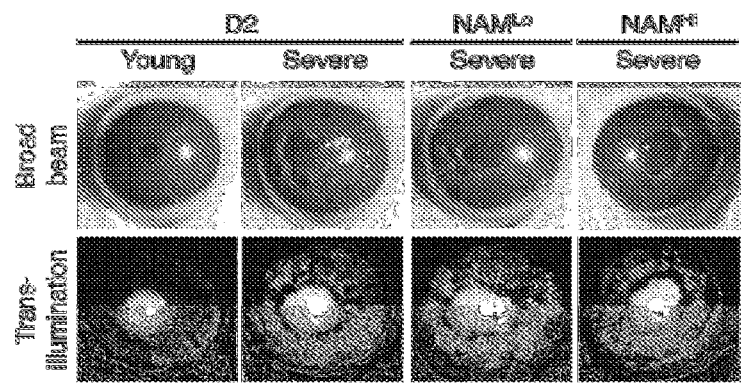
Figure 10C:
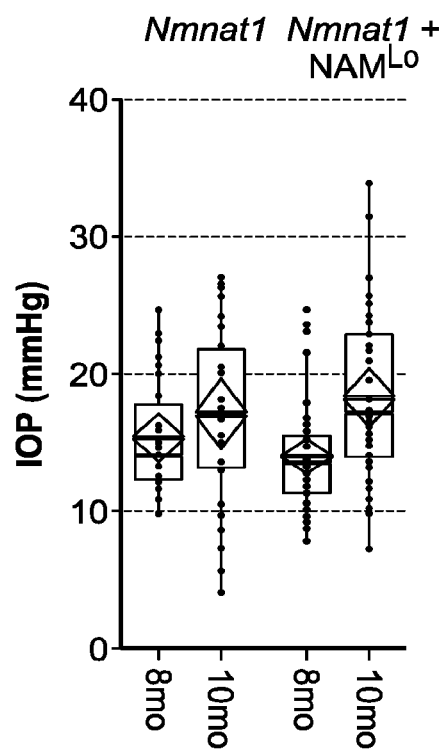
Figure 10D:
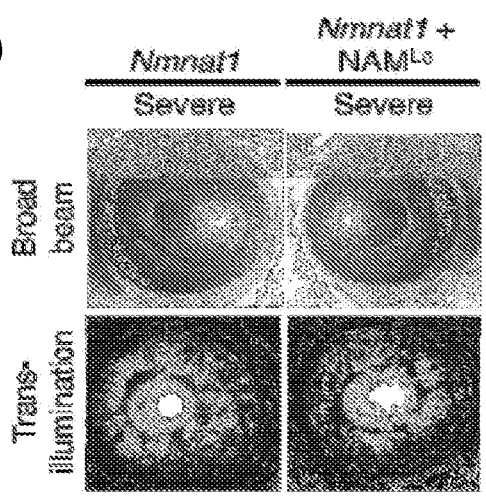
Figure 11A:
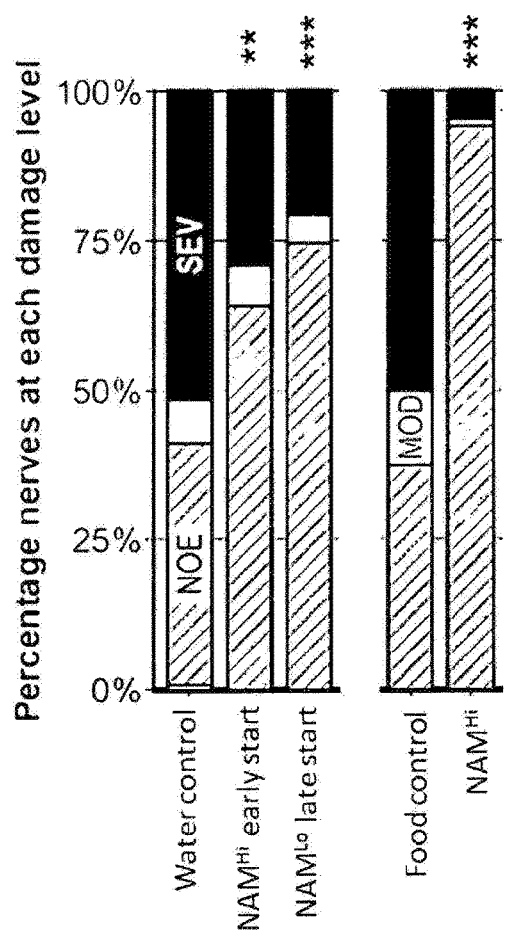
FIG. 11A shows that NAM protects from optic nerve degeneration. Green or lower sections of the bars=no or early, glaucoma (NOE) (a stage with no nerve damage), yellow or middle sections of the bars=moderate damage (MOD), red or top sections of the bars=severe (SEV) damage. Fisher's exact test: =P<0.01, *P<0.001. NAM$^{Lo}$=550 mg/kg/day. NAM$^{Hi}$=2000 mg/kg/day. Early start=treatment starts at 6 months of age (pre-elevated IOP in almost all eyes). Late start treatment starts at 9 months of age (following onset of elevated IOP; at this time-point the majority of eyes have or have had elevated IOP).
Figure 11B:
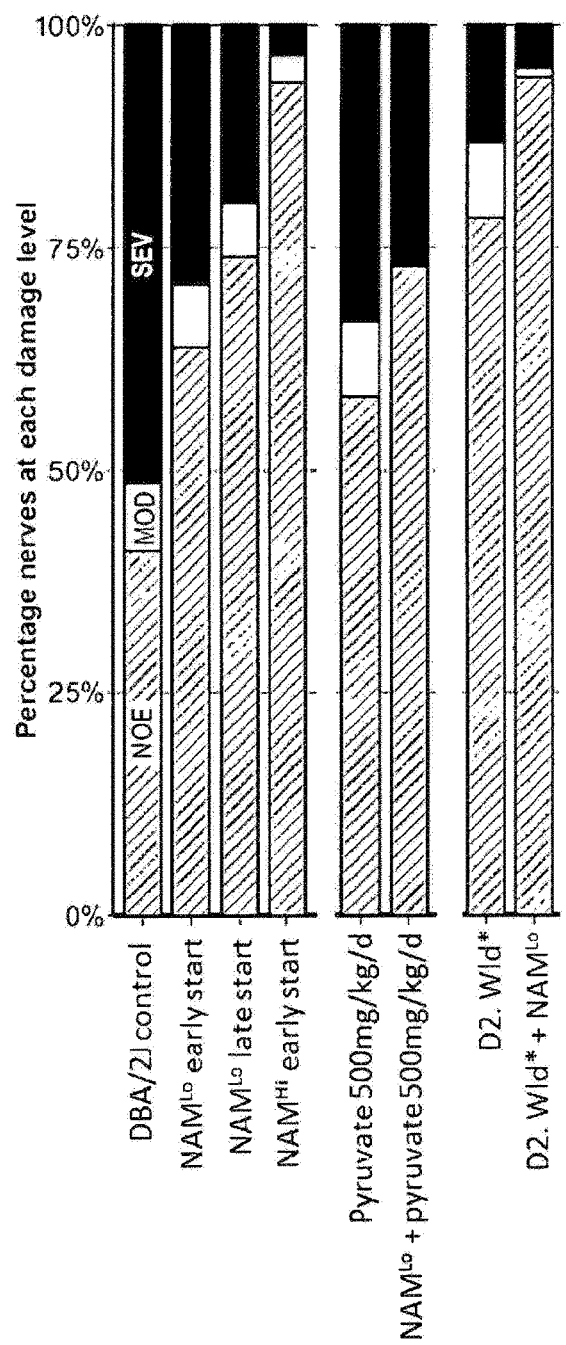
FIG. 11B shows that nicotinamide protects against optic nerve degeneration in D2 glaucoma at 12 months of age. Chart shows percentage of nerves with no detectable glaucoma (NOS; lower sections of the bars), moderate glaucomatous damage (MOD; middle sections of the bars), or severe glaucomatous damage (SEV; top sections of the bars). From left, DBA/2J control—D2 mice on standard drinking water; Nicotinamide (NAM$^{Lo}$) early start—D2 mice on standard drinking water supplemented with 550 mg/kg/day NAM from 6 months of age (pre-disease); Nicotinamide (NAM$^{Lo}$) late start—D2 mice on standard drinking water supplemented with 550 mg/kg/day NAM from 9 months of age (during disease); Nicotinamide (NAM$^{Hi}$) early start—D2 mice on standard drinking water supplemented with 2,000 mg/kg/day NAM from 6 months of age (pre-disease); Pyruvate—D2 mice on standard drinking water supplemented with 500 mg/kg/day pyruvate from 6 months of age (pre-elevated IOP); NAM$^{Lo}$+Pyruvate—D2 mice on standard drinking water supplemented with 550 mg/kg/day NAM+500 mg/kg/day pyruvate from 6 months of age (pre-disease); D2 Wld$^S$—D2 mice carrying the Wld$^S$ transgene (altered NMNAT enzyme that enhances enzymatic activity) on standard drinking water; D2. Wld$^S$+Nicotinamide (NAM$^{Lo}$)—D2 mice carrying the Wld$^S$ transgene (altered NMNAT enzyme) on standard drinking water with 550 mg/kg/day NAM from 6 months of age (pre-elevated IOP) Note that in addition to treating glaucomatous neurodegeneration interventionally, NAM also protects against glaucomatous neurodegeneration prophylactically.
Figure 12A:
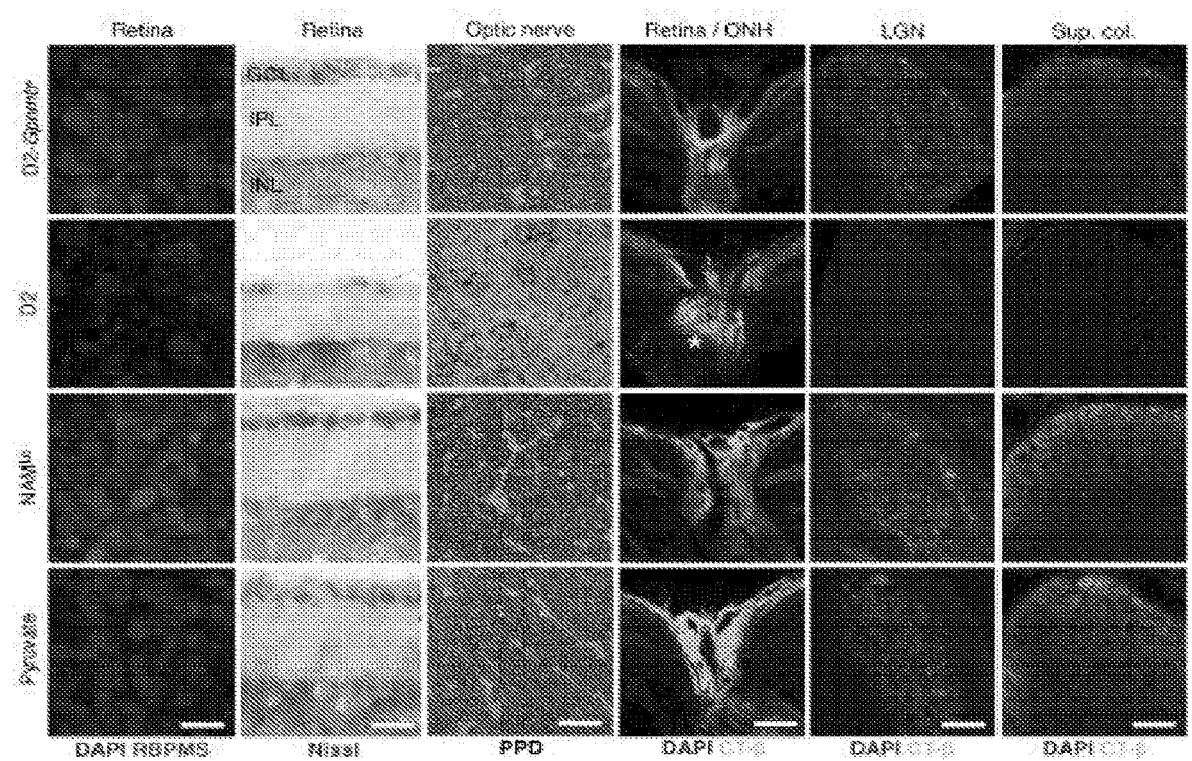
FIG. 12A shows that NAM and pyruvate protects from RGC soma loss (n=8/group), retinal NFL and IPL thinning (n=9/group), optic nerve degeneration (n>50/group), and loss of anterograde axoplasmic transport (n=20/group). Corresponding markers and color keys are beneath each column. Scale bars: RBPMS=20 μm, Nissl=20 μm, PPD=20 μm, CT-β=100 μm (retina), 200 μm (LGN, Sup, Col.), ONH=optic nerve head, LGN=lateral geniculate nucleus, Sup. Col.=superior colliculus. White asterisk denotes loss of axonal transport at the site of the ONH.
Figure 12B:
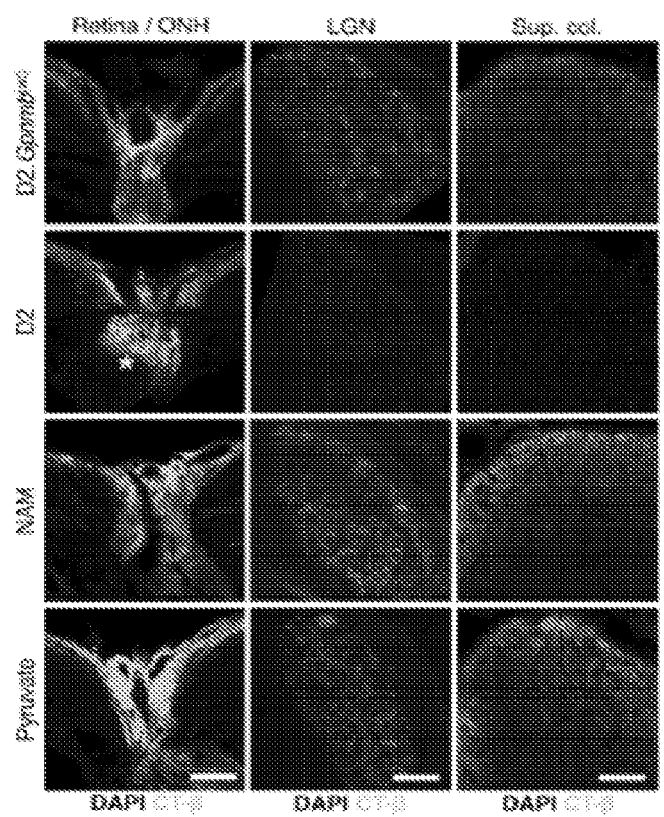
FIG. 12B shows recovery of axonal transport in NAM and pyruvate treated D2 mice. Loss of axonal transport is a prominent feature in glaucoma and can be used as a metric of neuronal health. Using a fluorescently labeled cholera toxin (Ct-B; green) axonal transport from the eye portion of the retinal ganglion cell to the terminal (brain) end of the cell can be visualized. Top row: D2.Gpnmb$^{(wt)}$ mice have normal, complete axonal transport from the retina to visual centers in the brain (LGN; lateral geniculate nucleus, Sup. col.; superior colliculus). Second row: D2 mice have incomplete axonal transport halting within the optic nerve (white asterisk). There is no labeling present in the visual centers of the brain. Third and forth rows: NAM treatment (third row) or pyruvate treatment (forth row) prevent axonal transport loss.
Figure 13A:
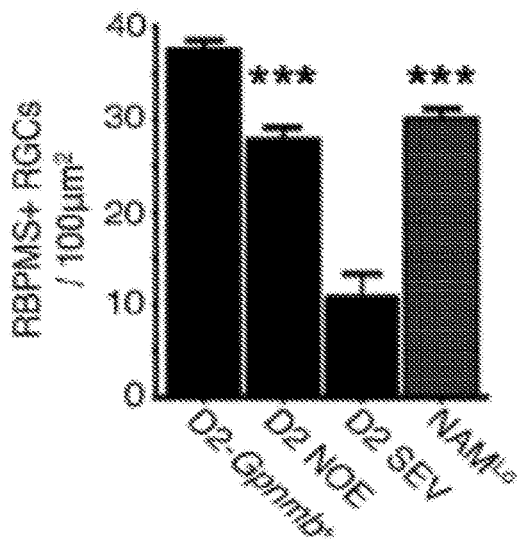
FIG. 13A shows that NAM protects from RGC soma loss (n=8/group, the density drop between D2 and D2-Gpnmb$^+$ is due to pressure induced stretching). ***=P<0.001.
Figure 13B:
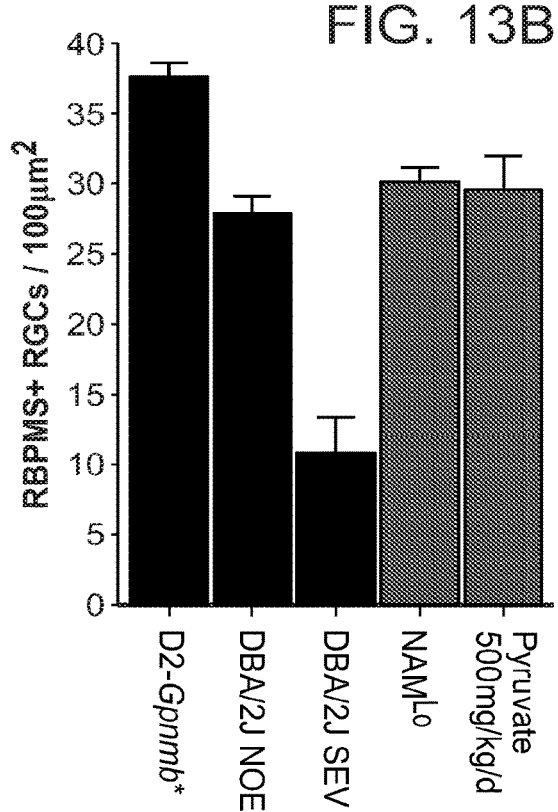
FIG. 13B shows NAM$^{Lo}$ (550 mg/kg/day) and pyruvate (500 mg/kg/day) prevent RGC soma loss (using a specific marker of RGCs; RBMPS).
Figure 14:
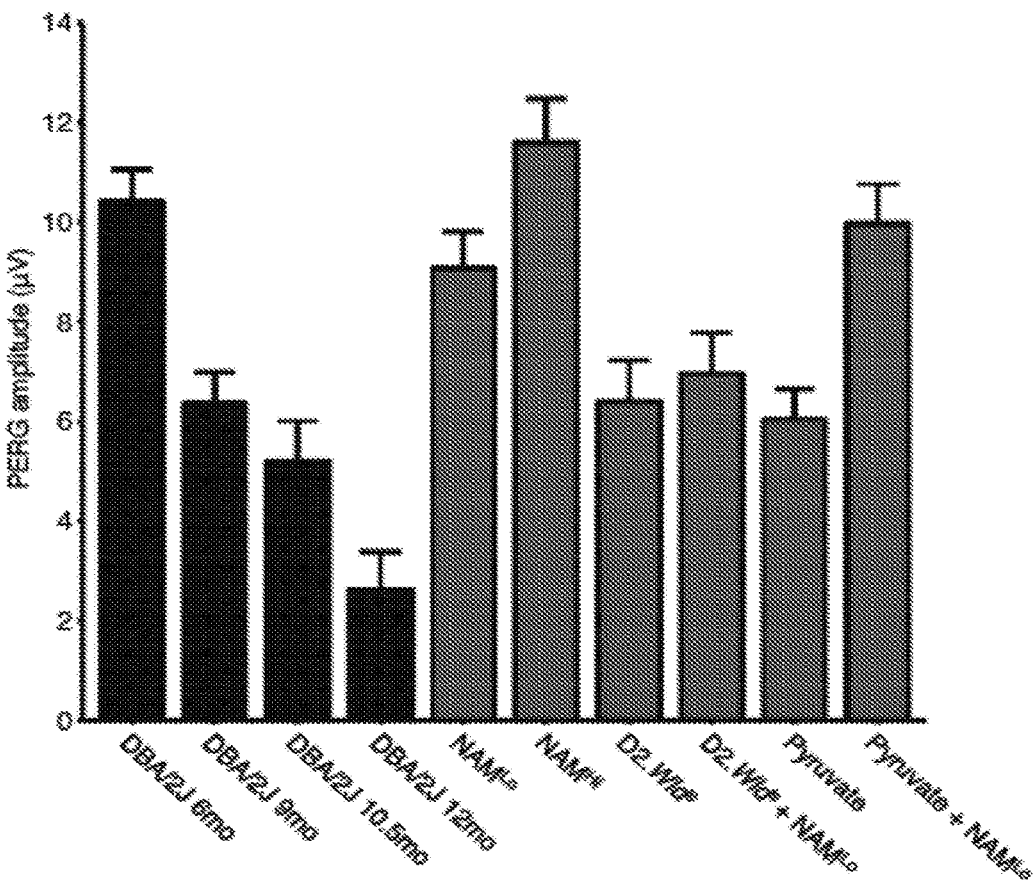
FIG. 14 shows that NAM (NAM$^{Lo}$ and NAM$^{Hi}$), pyruvate (500 mg/kg/day), Wld$^S$, and combinations thereof all protect D2 mice from early visual function loss based on visual function testing using PERG (pattern electroretinography) amplitude (n>20/group). PERG is a very sensitive and early measure of glaucoma, thus NAM or pyruvate treatment prevents even the very early stages of glaucoma. The combination of NAM$^{Lo}$+pyruvate, and the combination of NAM$^{Lo}$+Wld$^S$, both show additional recovery of PERG amplitude, NAM$^{Lo}$=550 mg/kg/day. NAM$^{Hi}$=2,000 mg/kg/day.

NAM at 550 mg/kg/d in mice demonstrates a clear neuroprotective effect (as IOP was not altered), the increased dose of 2000 mg/kg/d lessens the degree of IOP elevation (FIGS. 10A and 10B). This indicates that NAM protects against age-related pathogenic processes in additional cell types to RGCs.

The present data indicate that NAM protects against both IOP elevation and neural vulnerability, and therefore has dual benefits and great clinical potential in the treatment of human glaucoma. Even at the lower 550 mg/kg/d dose in which IOP is not altered, IOP lowering treatments (such as surgery or eye-drops) could be combined with NAM supplementation to provide greater protection against neurodegeneration.

Example 6 NAM is Effective in Two Models of RGC Death for Glaucomatous Insults

Glaucoma is a complex disease involving multiple insults. It has broad etiologies in which RGC compartments (e.g., soma, axon, dendrite) may be differently affected. Mechanical axon damage and local inflammation represent two important contributors to RGC degeneration during glaucoma.

To assess the effectiveness of NAM treatment in different contexts, we tested NAM efficacy in two models of RGC death. The first glaucomatous insult model involves the use of a tissue culture model of axotomy, and the second glaucomatous insult model relates to the use of intravitreal injections of soluble murine TNFα which drives local inflammation and is implicated in glaucoma.

Figure 23A:
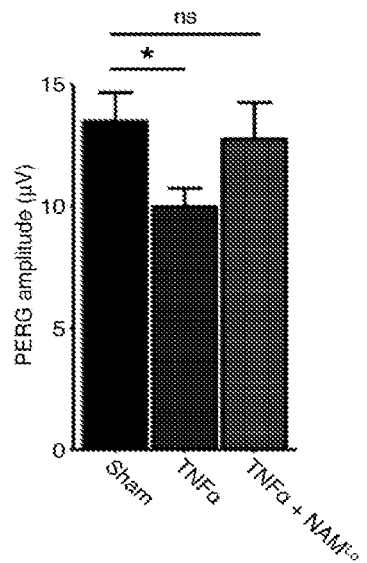
FIGS. 23A-23C show that NAM (NAM$^{Lo}$=550 mg/kg/day) prevents PERG (FIG. 23A) and soma loss (FIGS. 23B and 23C) in TNFα injected eyes at 12-week post-TNFα administration (n=20/group). *=P<0.05. ns=not statistically significant, Scale bar=20 μm.
Figure 23B:
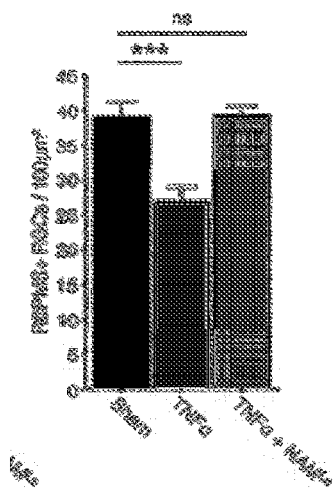
Figure 23C:
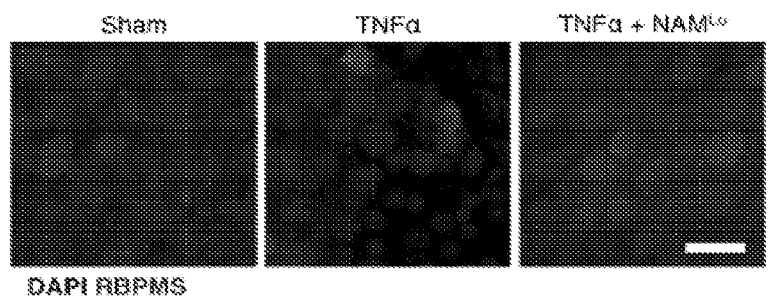

NAM robustly protected cultured retinas from RGC somal degeneration (FIGS. 22A and 22B), NAM also protected against a loss of PERG amplitude and cell loss in TNFα injected eyes (FIGS. 23A-23C).

Given these protections against severe acute insults, and commonalities between glaucoma and other neurodegenerative diseases, NAM could have broad implications for treating glaucoma and other age-related neurodegenerative diseases.

Example 7 Nmnat1Gene Therapy, Alleviates Glaucoma in D2 Mice

Figure 25:
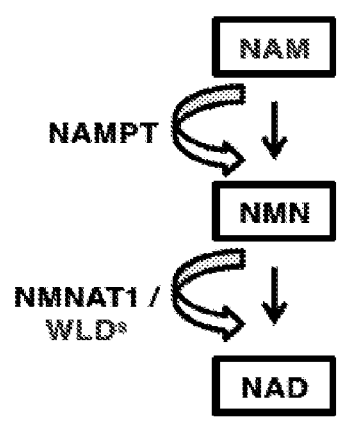
FIG. 25 shows the NAD recycling pathway with NAM and NMNAT1/WLD$^S$.

In this study, we demonstrate that overexpression of Nmnat1, a key enzyme in NAD⁺ production (FIG. 25), supports NAD⁺ producing cellular machinery.

We injected D2 mice eyes once at 5.5-month with AAV2.2 vector containing the Nmnat1 gene and the GFP reporter, under a CMV promoter expressed as a single transcript. Mice were anaesthetised, and injected intravitreally (i.e. behind the limbus, at a 45-60 degree angle into the vitreal chamber, avoiding the lens and central retina) with 1.5 µL of viral vector (3×10⁸ U/mL). Both eyes were injected. Immediately following injection hydrating eye drops were topically administered and mice were allowed to wake under a heat lamp. Eyes were clinically examined at multiple time points following injection to confirm absence of damage to the eye, Visual function assessment (by PERG) was performed prior to, and following, infection, confirming no adverse effects of the initial injection and viral transfection.

Nmnat1 expression (as assessed by GFP expression) was detectable at least as of the first week after AAV2.2 injection, and was robust in RGCs 2 weeks after injection (expressed in >83% of RGCs), and remained robust through to the end stage time point (12-month). The vast majority of RGCs were transduced and expressed virally delivered gene products as evidenced by GFP fluorescence in RGC cell somas in the retina and their terminal points in the brain, including the lateral geniculate nucleus (LGN) and superior collicuis (sup. col).

Figure 24A:
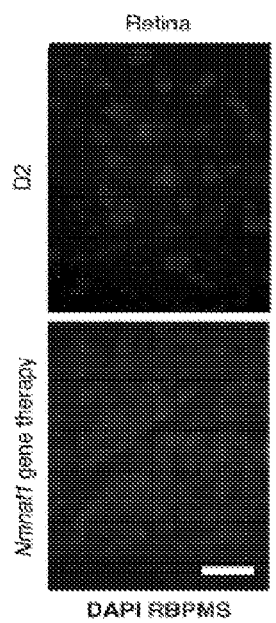
FIGS. 24A and 24B show that gene therapy robustly protects from glaucomatous neurodegeneration. D2 eyes were intravitreally injected at 5.5-month with AAV2.2 viral vector carrying a plasm id to overexpress murine Nmnat1 under a CMV promoter.
Figure 24B:
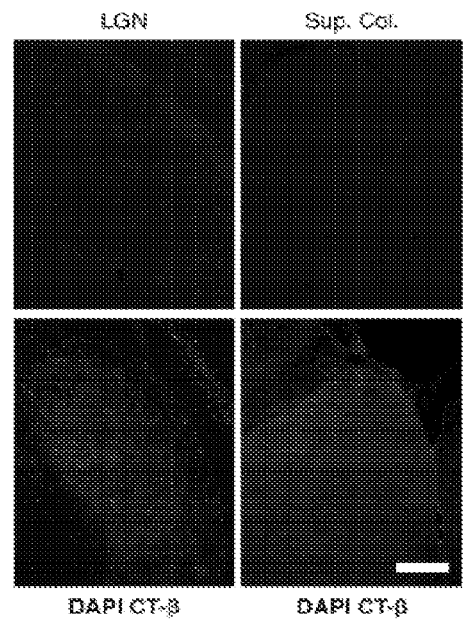
Figure 24C:
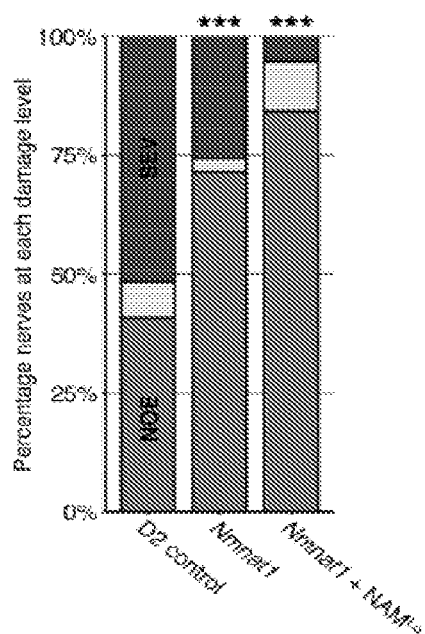
FIGS. 24C and 24D show that Nmnat1 gene therapy also protects D2 eyes with elevated IOP against optic nerve degeneration (n>40/group) (FIG. 24C), soma loss (n=8/group) (FIG. 24D, top panel), and PERG amplitude (n>20/group) (FIG. 24D, bottom panel). Addition of NAM (NAM$^{Lo}$=550 mg/kg/day) in drinking water afforded additional protection against optic nerve degeneration (Nmnat1 compared to Nmnat1+NAM$^{Lo}$=P<0.001, Fisher's exact test) (FIG. 24C). P<0.01, *=P<0.001.
Figure 24D:
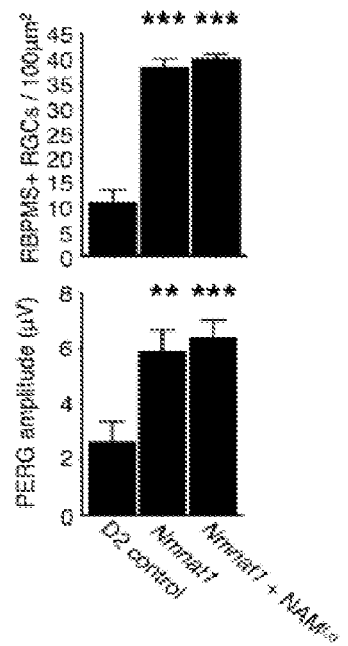

Overexpression of Nmnat1 was sufficient to prevent axon and soma loss (FIGS. 24A-24C, and FIG. 24D, upper panel) and to preserve axoplasmic transport and electrical activity in RGCs (PERG) (FIG. 24B and FIG. 24D—lower panel). Glaucomatous nerve damage was absent in >70% of treated eyes. This potent protection encourages the use of similar gene therapy strategies to prevent human glaucoma.

Example 8 Combination Therapy Using Nmnat1 Gene Therapy and NAM

In this study, we examined the effects of combinational therapy of Nmnat1 and NAM ($NAM^{Lo}$) by combining the experiments detailed in Example 4 and Example 7, Briefly, mice underwent gene therapy as above, following a 1 week viral shedding period mice were returned to our usual colony and administered NAM 550 mg/kg/d in normal drinking water.

This combination afforded significant additional protection with 84% of eyes having no detectable glaucomatous damage at 12 months of age. This represents a ~4-fold decrease in the risk of developing IOP induced glaucomatous neurodegeneration compared to untreated D2 controls. Increasing doses of NAM in combination with gene therapy is even more protective.

Example 9 $Wld^S$ Alleviates Glaucoma in D2 Mice

The Wallerian degeneration slow allele ($Wld^S$) has been show to partially protect in D2 glaucoma. The $WLD^S$ protein is a modified NMNAT1 protein (an enzyme which converts NMS to NAD). Cells containing the mutant protein $WLD^S$ show increased enzymatic activity, converting NMN to NAD either quicker or more efficiently.

In this experiment, we demonstrated that NAM and $Wld^S$ combination better protects against glaucoma than $Wld^S$ alone, in D2 mice bearing the $Wld^S$ mutation. Mice administered NAM and carrying the $Wld^S$ mutation show profound protection from glaucomatous damage (~95% no glaucoma).

The experiment was run essentially the same as in Example 4, except that D2 mice with the Wallerian degeneration slow allele ($Wld^S$) were used. The results were also shown in FIG. 11B. It is evident that either $Wld^S$ alone or NAM alone protects against D2 glaucoma, but the combination of $Wld^S$ and NAM is significantly better than $Wld^S$ alone.

Specifically, NAM alone is about 70% protective in glaucoma. Meanwhile, NAM+$Wld^S$ is ~95% protective in glaucoma. Both NAM and NAM+$Wld^S$ protect all portions of the cell and optic nerve (data not shown). Thus, while NAM and $Wld^S$ are partially protective individually, the combination exhibited a significant synergistic effect (i.e., from ~70% protection to ~95%).

While not wishing to be bound by any particular theory, it is believed at increasing Nmnat expression by using the $Wld^S$ mutation allows more NAM to be converted to NADt, and the combination protects against neurodegeneration in glaucoma synergistically.

Consistent with this theory, in DBA/2J mice, there is an age and disease related decrease in cellular levels of NADt and other TCA/Krebs Cycle components (such as pyruvate, FIG. 5D). Thus the cellular levels of NADt (NAD⁺/NADH) was determined in treated animals.

We found that levels of NADt (NAD⁺/NADH) were restored in NAM treated mice as well as in $Wld^S$ mice. When $Wld^S$ mice is further treated with NAM, the restoration of NADt level is synergistic in NAM+$Wld^S$ treated mice. (See FIG. 5E).

The result of this example is consistent with that in Example 8.

NADt (NAD⁺/NADH) levels are thought to change in aging and neurodegenerative diseases. The data provided herein demonstrates that administration/supplementation of NAM, NAM derivatives, and/or NMNAT enzyme may be protective in a large range of aging and disease phenotypes.

Example 10 Pyruvate Alleviates/Prevents Glaucoma in D2 Mice

This example demonstrates that nicotinamide (Vitamin B3) and/or in combination with pyruvate (a simple metabolite of glucose) robustly protect DBA/2J mice from vision loss, loss of axonal transport, retina and optic nerve damage. Gene expression experiments demonstrate that mice treated with nicotinamide are more closely molecularly matched to young control mice, rather than age-matched non-glaucomatous mice. The data suggests that nicotinamide may be working in part through an age-dependent mechanism, delaying age dependent increases in susceptibility to glaucoma. The magnitude of protection that NAM provides is completely unexpected and surprising.

Pyruvate is an important simple alpha-keto acid involved in metabolism where it is produced from glucose. Pyruvate is converted into acetyl-coenzyme A, the main input for the Kreb's cycle (citric acid cycle). During normoxia (normal conditions) pyruvate increases NADH levels.

Pyruvate levels decrease in the retina with age, sensitizing retinal neurons to glaucomatous damage from high intraocular pressure (FIG. 5D). Mice administered pyruvate in normal drinking water had increased levels of pyruvate in the retina (FIG. 5D). Mice administered pyruvate in normal drinking water were resistant to optic nerve axon degeneration, cell loss and visual dysfunction (as assessed by PERG) in glaucoma (FIGS. 11B, 12B, 13B, and 14).

The findings above showed increased potency in mice both administered NAM and pyruvate, demonstrating a synergistic effect between NAM- and pyruvate-treatment to prevent neuronal degeneration.

Example 11 PQQ Prevents Nuclear Diameter Shrinkage and Decrease in Cell Density

Additional neuroprotective agents were also tested to determine their roles in neurodegenerative diseases.

Figure 26A:
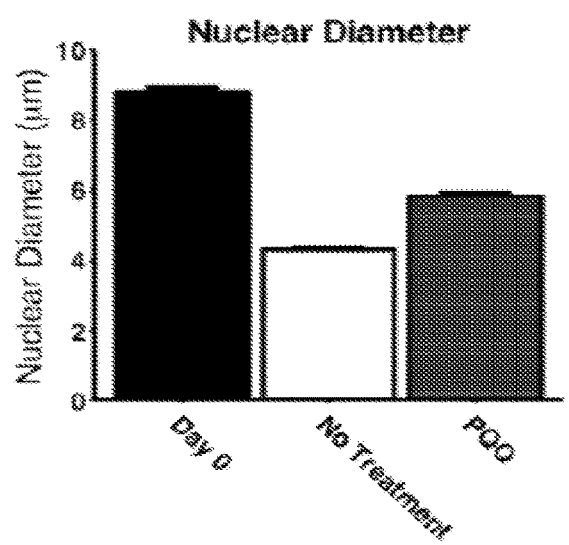
FIGS. 26A and 26B show that PQQ administration prevents nuclear diameter shrinkage (FIG. 26A), and a decrease in cell density (FIG. 26B), in axotomized retinas treated with PQQ.
Figure 26B:
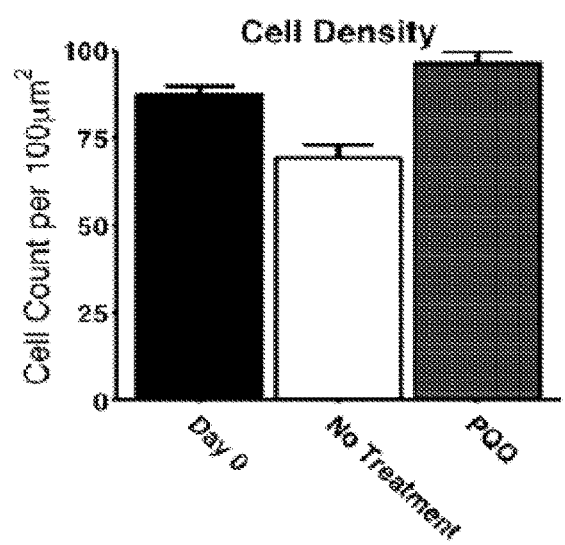
Figure 27A:
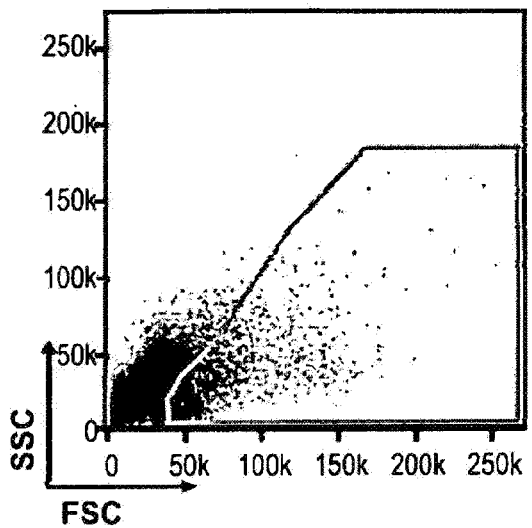
FIGS. 27A-27E show FACS sorting RGCs. Retinal samples were stained with an antibody cocktail (see Materials and Methods).
Figure 27B:
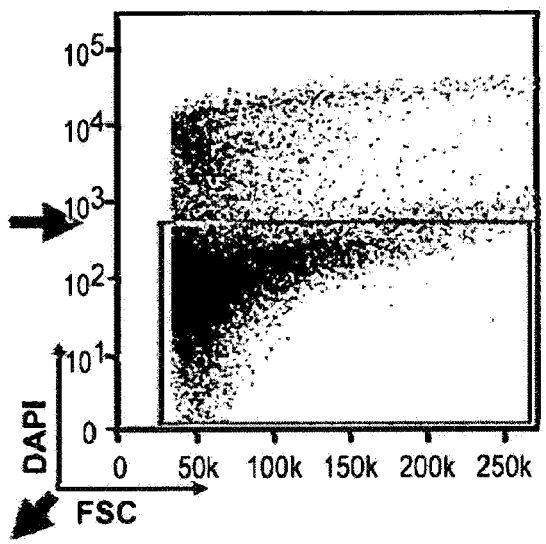
Figure 27C:
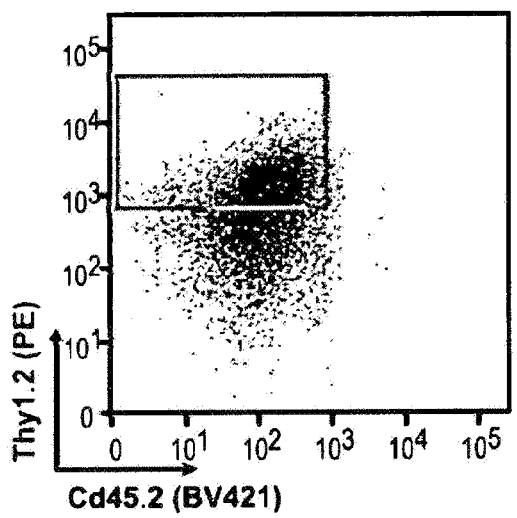
Figure 27D:
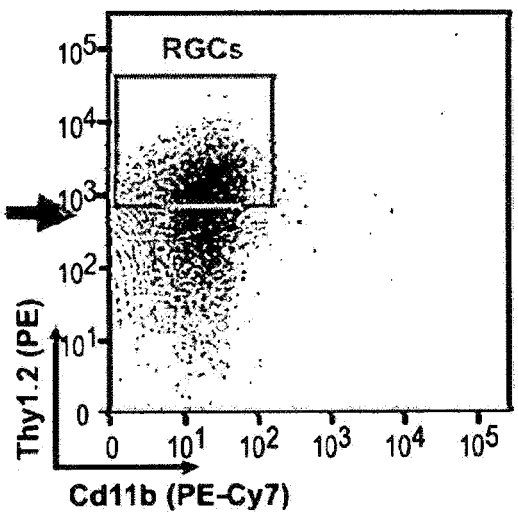
Figure 27E:
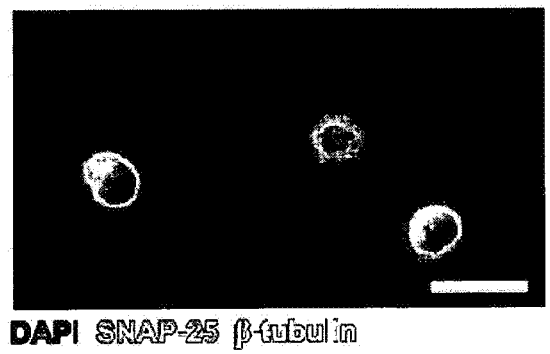

In one experiment, similar experiments were set up to determine the neuroprotective function of pyrroloquinoline quinone (PQQ). PQQ is an important redox cofactor, similar to nicotinamide. PQQ promotes mitochondrial biogenesis, and its neuroprotective function is thought to depend on its functions as an antioxidant. FIG. 26 shows that PQQ is protective in retina tissue culture.

Example 12 Glutathione Levels in the Retina Decrease with Age

N-acetylcysteine (N-acetyl-L-cysteine or NAC) is a precursor to L-cysteine, a precursor to glutathione, a potent biological antioxidant, and a major redox buffer in neurons. Data in FIG. 5B shows that glutathione levels in the retina decrease with age.

NADPH (produced from NAD) is required for GSH synthesis from GSSG. Thus, NAD and GSH levels are intrinsically linked.

MATERIALS AND METHODS

1. Mouse Strains, Breeding and Husbandry

Mice were housed in a 14-hr light/10-hr dark cycle with food and water available ad libitum as previously reported (Howell et al., *Journal of Clinical Investigation* 121, 1429-1444, 2011). All breeding and experimental procedures were undertaken in accordance with the Association for research for Vision and Ophthalmology Statement for the Use of Animals in Ophthalmic Research. The Institutional Biosafety Committee and the Animal Care and Use Committee at The Jackson Laboratory approved this study.

C57BL/6J (B6), DBA/2J (D2), and DBA/2j-Gpnmb$^{R150X}$ (D2-Gpnmb$^+$) strains were utilized and have been described in detail elsewhere (Anderson et al., *Nature Genetics* 30, 81-85, 2002). D2-Gpnmb$^+$ mice do not develop high IOP and thus do not develop glaucomatous neurodegeneration (Libby et al., *Vis Neurosci* 22, 637-648, 2005). They are a genetically matched control for DBA/2J mice.

For aged glaucoma experiments mice were administered NAM in food and/or water starting at 6-month (prophylactic, prior to IOP elevation in almost all eyes) or 9-month (when the majority of eyes have high IOP and molecular changes, but no detectable neurodegeneration) (Howell et al., *Journal of Clinical Investigation* 121, 1429-1444, 2011). These molecular changes are prior to PERG defects and loss of anterograde axoplasmic transport. Low dose NAM (NAM$^{Lo}$, 550 mg/kg/d, PanReac AppliChem) was dissolved in regular acid drinking water (350 mL) and changed once per week. For high-dose NAM (NAM$^{Hi}$, 2000 mg/kg/d), NAM was available in both water (550 mg/kg/d) and food (1450 mg/kg/d) and was changed once per week. NAM food was prepared in a previously published, custom Western diet for palatability (LabDiet) (Graham et al., *Sci Rep* 6, 21568, 2016). Control mice received the same diet with no added NAM. This diet has no effects on the ocular health of the mice.

2. FAC sorting of RGCs

Prior to cell collection, all surfaces and volumes were cleaned with 70% ethanol and RNaseZap (ThermoFisher Scientific) solution followed by dH$_2$O. Mice were euthanized, eyes enucleated and placed immediately into ice-cold HBSS. Retinas were dissected from the eyes (4- or 9-month of age, no axon degeneration confirmed by PPD staining, data not shown) in HBSS on ice and placed directly into 100 µL, of a custom HBSS (Gibco), dispase (5 U/mL) (Stemcell Technologies), DNase 1 (2000 U/mL) (Worthington Biochemical) and SUPERase (1 U/µL) (ThermoFisher Scientific) solution. All retinas were from eyes that had no glaucomatous axon degeneration by PPD staining and analysis (see optic nerve assessment below). Retinas were incubated for 20 mins at 37° C. and shaken at 350 RPM in an Eppendorf Thermomixer R followed by gentle trituration using a 200 µL pipette. Samples were blocked in 2% BSA, SUPERase (1 U/µL) in HBSS, and stained with conjugated antibodies against Cd11b, Cd11c, Cd34, Cd45.2, GFAP, Thy1.2 as well as DAPI. This cocktail allowed other retina cell types to be accurately removed during FACS.

FACS was performed on a FACSAria (BD Biosciences). Thy1.2$^+$ (and negative for all other markers) RGCs were sorted into 300 µL buffer RLT+1% β-ME, vortexed and frozen at −80° C. until further processing.

3. RNA-Sequencing

RAC sorted RGC samples were defrosted on ice and homogenized by syringe in RLT Buffer (total volume 300 µL). Total RNA was isolated using RNeasy micro kits according to manufacturer's protocols (Qiagen) including the optional DNase treatment step, and quality was assessed using an Agilent 2100 Bioanalyzer. The concentration was determined using Ribogreen Assay (Invitrogen). Amplified dscDNA libraries were created using a Nugen Ovation RNA-seq System V. The SPIA dscDNA was sheared to 300 bp in length using a Diogenode Disruptor. Quality control was performed using an Agilent 2100 Bioanalyzer and a DNA 1000 chip assay.

Library size produced was analyzed using qPCR using the Library Quantitation kit/Illumina GA/ABI Prism (Kapa Biosystems). Libraries were barcoded, pooled, and sequenced 6 samples per lane on a HiSeq 2500 sequencer (illumina) giving a depth of 30-35 million reads per sample.

4. Differential Gene Expression and Pathway Analysis

Samples were subjected to quality control analysis by a custom quality control python script. Reads with 70% of their bases having a base quality score ≥30 were retained for further analysis. Read alignment was performed using TopHat v 2.0.7 (Kim et al., *Genome Biol* 14, R36, 2013) and expression estimation was performed using HTSeq (Anders et al., *Bioinformatics* 31, 166-169, 2015) with supplied annotations and default parameters against the DBA/2J mouse genome (build-mm10). Bamtools v 1.0.2 (Barnett el al., *Bioinformatics* 27, 1691-1692, 2011) were used to calculate the mapping statistics.

Differential gene expression analysis between groups was performed using edgeR v 3.10.5 (Robinson et al., *Bioinformatics* 26, 139-140, 2010) following, batch correction using RUVSeq, the removal of outlier samples and lowly expressed genes by removing genes with less than five reads in more than two samples. Normalization was performed using the trimmed mean of M values (TMM).

Unsupervised HC was performed in R (1-cor, Spearman's rho). A total of 72 samples across all groups successfully amplified and sequenced and following HC pipelines 9 samples were removed as outliers. Adjustment for multiple testing was performed using false discovery rate (FDR). Genes were considered to he significantly differentially expression at an FDR <0.05.

To study age-related changes, comparisons were made between 4-month and 9-month D2-Gpnmb$^+$ samples and NAM$^{Lo}$ samples. For pathway analysis, QIAGEN's Ingenuity Pathway Analysis (IPA, Qiagen) was used for network generation across genes that are significantly differentially expressed. Lists of significantly differentially expressed genes were uploaded to IPA and mapped to the Mus musculus Entrez gene symbols using the IPA knowledge base. These objects will then be overlaid onto a canonical pathways developed from information contained in the IPA Knowledge Base. IPA's inbuilt network scoring algorithm will be used to rank the networks generated.

5. Metabolic Phenotyping

For GSH/GSSO and NAD$^+$/NADH quantification retinas were dissociated (as above) and compounds measured following the manufacturer's instructions (GSH/GSSG, Cayman Chemical; NAD$^+$/NADH, Biovision). Results were calculated according to the standard curve generated by using standards from the kits. Final metabolite concentrations for each samples were normalized to total protein concentration measured by Bradford assay.

6. Whole Retina Explant Culture

Mice were euthanized, eyes enucleated and placed immediately into ice-cold HBSS. Retinas were dissected from the eyes in HBSS on ice, flat-mounted with the ganglion cell layer up on a cell culture insert (Millipore), and submerged in tissue culture media containing Neurobasal-A, 1% penicillin-streptomycin (10000 U/mL), 1% glutamine (100×), 1% N-2 (100×) and 1% B-27 (50×) (all ThermoFisher Scientific).

For drug treated retinas tissue culture media was made as above and supplemented with one of the following compounds (all Sigma unless otherwise): β-NAD, NAM (Pan-Reac AppliChem), β-NMN. Retinas were incubated in 6-well plates at 37° C. and 4% $CO_2$ for 5 days before being fixed in 4% PFA and stained with DAPI. (For untreated "Day 0" controls, retinas were dissected and placed straight into 4% PFA.) Retinas were imaged on a Zeiss AxioObserver.

7. Soluble Murine TNF α Injections

To induce delayed retinal ganglion cell degeneration, soluble murine TNFα (1 ng/μL) was intravitrally injected as previously described (Nakazawa et al., *J Neurosci* 26, 12633-12641, 2006). Ten week old B6 mice were pre-treated with NAM for 2 weeks prior to TNFα injections and PERG was performed at 8, 10 and 12 weeks of age. Mice we sacrificed at 12-week and RGC counts performed.

8. Clinical Phenotyping

IOP elevation in D2 mice is subsequent to a pigment dispersing iris disease. In all experiments, the progression of the iris disease and intraocular pressure in mutant or drug-treated mice was compared to control D2 mice as previously described (John et al., *Invest Ophthalmol Vis Sci* 39, 951-962, 1998). In each experiment, iris disease and intraocular pressure were assessed.

Iris disease was assessed at two-month intervals starting at 6 months of age until experiment completion.

Intraocular pressure was measured at 45-day intervals beginning at 8.5-9 month until experiment completion.

9. Pattern Electroretinography (PERG)

PERG was recorded subcutaneously from the snout as previously reported. Briefly: patterned stimuli (gratings of 0.05 cycles/degree, 100% contrast) generated on LED panels were presented at each eye separately with slight different frequencies around 1 Hz. Waveforms were retrieved using an asynchronous averaging method (Chou et al., *Invest Ophthalmol Vis Sci* 55, 2469-2475, 2014).

Mice were anaesthetized using ketamine/xylazine (Savinova et al., *BMC Genet* 2, 12, 2001) and body temperature maintained at 37° C. on a feedback-controlled heated stage monitored by rectal thermometer.

10. Optic Nerve Assessment and Determination of Glaucomatous Damage

The processing of optic nerves and staining with para-phenylenediamine (PPD) was as published (Smith et al., Systematic evaluation of the mouse eye. *Anatomy, pathology and biomethods*. CRC Press, Boca Raton, 2002). PPD stains the myelin sheath of all axons but darkly stains the axoplasm of only damaged axons. It is well established to provide a very sensitive measure of optic nerve damage (Smith et al., Systematic evaluation of the mouse eye. *Anatomy, pathology and biomethods*. CRC Press, Boca Raton, 2002).

Briefly, intracranial portions of optic nerves were fixed in 4% PFA at RT for 48 hrs, processed and embedded in plastic. A segment of optic nerve from within a region up to 1 mm from the posterior surface of the sclera was sectioned (1 μm thick sections) and stained with PPD. Typically 30-50 sections are taken from each nerve.

Multiple sections of each nerve were considered when determining damage level. Optic nerves were analyzed and determined to have one of 3 damage levels:
(1) No or early damage (NOE) less than 5% axons damaged and no gliosis. This level of damage is seen in age and sex matched non-glaucomatous mice and is not due to glaucoma. Although none of these eyes exhibit glaucomatous nerve damage, this damage level is called no or early glaucoma as some of these eyes have early molecular changes that precede neurodegeneration. These molecular changes can be detected by gene expression studies (Howel (el al., *Journal of Clinical Investigation* 121, 1429-1444, 2011). Eyes with these early molecular changes but no degeneration are considered to have early glaucoma when discussing metabolic, mitochondrial and gene expression changes herein.

(2) Moderate damage (MOD)—average of 30% axon loss and early gliosis.
(3) Severe (SEV)→50% axonal loss and damage with prominent gliosis.

11. Anterograde Axon Transport

Mice were anaesthetized using ketamine/xylazine and intravitreally injected with 2 µL AF488 or AF594 cholera toxin subunit B (1 mg/mL in PBS) (ThermoFisher Scientific). After 72 hrs mice were anaesthetized and euthanized via 4% PFA cardiac perfusion. Brains and eyes were post-fixed in 4% PFA fir an additional 24 hrs, cryoprotected in 30% sucrose in PBS overnight (ON), OCT cryoembedded and sectioned at 20 µm. AF488 was visualized using a Zeiss AxioObserver or Zeiss AxioImager.

12. Histology

For immunofluorescence staining, mice were euthanized by cervical dislocation, their eyes enucleated and placed in 4% PFA ON. Retinas were dissected and flat-mounted onto slides, permeabilized with 0.1% Triton-X for 15 mins, blocked with 2% BSA in PBS and stained ON at RT in primary antibody (see below for list of antibodies).

After primary antibody incubation, retinas were washed 5 times in PBS, stained for 4 hrs at RT with secondary antibody. Slides were then washed a further 5 times with PBS, stained with DAPI for 15 mins, mounted with fluoromount, coverslipped and sealed with nail-polish.

For retinal sections, eyes were cryoprotected in 30% sucrose ON, frozen in OCT and cryosectioned at 18 µm. Slides were warmed to room temperature and the procedure above was followed. Retinas were imaged on a Zeiss AxioObserver for low resolution counts. Retinal sections were imaged on a Leica SP8 far higher resolution images.

For Nissl staining, frozen sections were warmed to room temperature, placed in 1:1 alcohol:chloroform ON, and rehydrated through serial alcohol gradient. Slides were washed once in distilled water and stained for 15 mins in 0.1% cresyl violet in distilled water before being differentiated in 95% alcohol, dehydrated in 100% alcohol and cleared in xylene. Slides were prepared as above. Nissl stained retinal sections were imaged using a Nikon Eclipse E200.

For Oil Red O staining, slides were warmed to room temperature, washed quickly in 60% isopropanol, incubated at RT in Oil Red O and Haematoxylin for 15 mins, washed in 60% isopropanol again, mounted and coverslipped. Oil Red O stained retinal sections were imaged using a Nikon Eclipse E200.

13. Western Blotting

Mice were euthanized by cervical dislocation, eyes enucleated and placed immediately into ice-cold HBSS. Retinas were dissected from the eyes in HBSS, placed directly in to RIPA buffer and homogenized. Protein extracts separated by SDS-PAGE in precast gels (Bio-Rad) and transferred onto PVDF membranes using an iBlot 2 (ThermoFisher Scientific). Membranes were blocked in 5% milk or 5% BSA in 0.1% PBS-Tween and antibody incubations were performed in blocking solution. Antibody staining was detected using ECL. Protein concentration was assessed by Bradford assay and normalized to a housekeeping protein using densitometry.

14. Electron Microscopy

Mice were euthanized, eyes enucleated, and then fixed ON in Smith-Ruda (0.8% PFA and 1.2% gluteraldehyde in 0.1 M phosphate buffer). The cornea and lens were dissected off and the remaining posterior eye-cup (containing the retina and ONH) were post-fixed in 2% aqueous osmium tetroxide and dehydrated in ethyl alcohol. Samples were then infiltrated and flat-mounted in Embed 812/Araldite resin (Electron Microscopy Sciences) to allow en face sections. Blocks were polymerized at 60° C. for 48 hrs and 90 nm microtome sections were cut (Leica UC6, Leica) onto 300 mesh copper grids. Grids were stained with 1% aqueous uranyl acetate/Reynold's lead citrate and were viewed on a JEOL JEM 1230 TEM. Images were collected on an AMT 2K camera.

15. Gene Therapy

For virally delivered gene therapy, mice were anaesthetized (as above), and intravitreally injected with 1.5 µL ($3.1 \times 10^{10}$ gc/mL) AAV2.2 murine Nmnat1 under a CMV promoter with a GFP reporter (referred to as Nmnat1 in main text; Vector Biolabs #ADV-265880). Mice were injected at 5.5-month of age in a BSL2 laboratory and moved to our regular mouse colony after 2 weeks.

For Nmnat1 mice undergoing additional NAM treatment, mice were given 550 mg/kg/d NAM in normal drinking water from 6-month of age. Mice were euthanized at 12-month.

16. Antibodies

Antibodies used in the examples above are listed below. IF: immunofluorescent. WB: Western Blot

| Antibody | Use | Concentration | Manufacturer | Catalogue # |
|---|---|---|---|---|
| CYCS | WB | 1:1000 | Abcam | ab90529 |
| EIF2 | WB | 1:1000 | Cell Signaling | 97225 |
| H2AX | IF | 1:500 | Millipore | 05-636 |
| HIF1A | IF | 1:500 | Novus Biologicals | NB100-105 |
| PARP | IF | 1:500 | BD Pharmingen | 556362 |
| RBPMS | IF | 1:500 | Novus Biologicals | NBP2-20112 |
| SNAP-25 | IF | 1:250 | Abcam | ab24737 |

17. Statistical Analysis

The sample size (number of eyes, n) is shown in each figure legend. Graphing and statistical analysis was performed in R. Student's t test was used for pairwise analysis in quantitative plots and error bars refer to standard error of the mean unless otherwise stated.

All cited references are incorporated by reference. While specific embodiments of the present invention have been described in the foregoing, it will be appreciated by those skilled in the art that many equivalents, modifications, substitutions, and variations may be made thereto without departing from the spirit and scope of the invention as defined in the appended claims.

The invention claimed is:
1. A method of reducing axonal degeneration of a retinal ganglion cell and treating glaucoma in a subject in need thereof, comprising the step of orally administering to the subject a therapeutically effective amount of nicotinamide (NAM) and pyruvate wherein the subject is a mammal and administered between 1 and 5 g/day of NAM and between 1 and 5 g/day of pyruvate, wherein axonal degeneration in a retinal ganglion cell is reduced.

2. The method of claim 1, wherein the subject is also administered one or more compounds selected from the group consisting of nicotinamide mononucleotide (NMN), pyrroloquinoline quinone (PQQ), nicotinamide adenine dinucleotide (NAD) and nicotinamide ribose (NR).

3. The method of claim 1, wherein the NAM is present in a therapeutically effective amount to reduce intraocular pressure.

4. The method of claim 1, wherein the NAM and pyruvate are present in therapeutically effective amounts to reduce neurodegeneration in a retinal ganglion cell or to reduce intraocular pressure.

5. The method of claim 1, wherein the subject is a human subject.

6. The method of claim 1, the method further comprises the step of administering a gene composition, wherein said gene composition comprises a polynucleotide encoding NMNAT1.

7. The method of claim 6, wherein the polynucleotide is in a viral vector.

8. The method of claim 7, wherein the viral vector is an adeno-associated virus (AAV) vector, an adenoviral vector, a lentiviral vector, or a retroviral vector.

9. The method of claim 7, wherein the viral vector is an AAV vector.

10. The method of claim 7, wherein the viral vector is a lentiviral vector.

11. The method of claim 6, wherein the gene composition is administered intravitreally or intraocularly.

12. The method of claim 6, wherein the gene composition is administered intravitreally.

13. The method of claim 1, further comprising administering to the subject an additional therapeutic agent.

14. The method of claim 13, wherein the additional therapeutic agent is a beta blocker, a nonselective adrenergic agonist, a selective a-2 adrenergic agonist, a carbonic anhydrase inhibitor, a prostaglandin analog, a para-sympathomimetic agonist, a carbachol or a combination thereof.

15. The method of claim 13, wherein the additional therapeutic agent is timoiol, levobunolol, metipranolol carteolol, betaxolol, epinephrine, apraclonidine, brirnonidine, acetazolamide, methazolamide, dorzolamide, brinzolamide, latanoprost, travaprost, bimataprost, pilocarpine, echothiophate iodide, carbachol, or a combination thereof.

16. A method of preventing glaucoma in a subject in need thereof, comprising the step of orally administering to the subject a pharmaceutical composition containing a therapeutically effective amount of nicotinamide (NAM) and pyruvate to reduce axonal degeneration in a retinal ganglion cell and prevent glaucoma, wherein the subject is a mammal and is administered between 1 and 5 g/day of NAM and between 1 and 5 g/day of pyruvate.

17. A method of improving visual function in a subject in need thereof, comprising the step of orally administering to the subject a pharmaceutical composition containing a therapeutically effective amount of nicotinamide (NAM) and pyruvate to reduce axonal degeneration in a retinal ganglion cell and improve visual function, wherein the subject is a mammal and is administered between 1 and 5 g/day of NAM and 10 between 1 and 5 g/day of pyruvate.

18. The method of claim 16, wherein the subject is a human subject.

19. The method of claim 17, wherein the subject is a human subject.

* * * * *